United States Patent
Joung et al.

(10) Patent No.: US 12,241,096 B2
(45) Date of Patent: *Mar. 4, 2025

(54) ENGINEERED CRISPR-Cas9 NUCLEASES WITH ALTERED PAM SPECIFICITY

(71) Applicant: The General Hospital Corporation, Boston, MA (US)

(72) Inventors: J. Keith Joung, Winchester, MA (US); Benjamin Kleinstiver, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/174,294

(22) Filed: Feb. 24, 2023

(65) Prior Publication Data

US 2023/0407277 A1    Dec. 21, 2023

Related U.S. Application Data

(63) Continuation of application No. 17/674,558, filed on Feb. 17, 2022, now Pat. No. 11,624,058, which is a continuation of application No. 16/109,657, filed on Aug. 22, 2018, now Pat. No. 11,286,468.

(60) Provisional application No. 62/641,687, filed on Mar. 12, 2018, provisional application No. 62/549,303, filed on Aug. 23, 2017.

(51) Int. Cl.
| | |
|---|---|
| C12N 9/22 | (2006.01) |
| C12N 9/02 | (2006.01) |
| C12N 9/10 | (2006.01) |
| C12N 9/78 | (2006.01) |
| C12N 9/80 | (2006.01) |
| C12N 15/11 | (2006.01) |
| C12N 15/90 | (2006.01) |
| A61K 38/00 | (2006.01) |

(52) U.S. Cl.
CPC ............ *C12N 9/22* (2013.01); *C12N 9/0071* (2013.01); *C12N 9/1007* (2013.01); *C12N 9/1029* (2013.01); *C12N 9/78* (2013.01); *C12N 9/80* (2013.01); *C12N 15/11* (2013.01); *C12N 15/907* (2013.01); *A61K 38/00* (2013.01); *C07K 2319/71* (2013.01); *C07K 2319/80* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 7,803,550 | B2 | 9/2010 | Makarov et al. |
| 8,071,312 | B2 | 12/2011 | Makarov et al. |
| 8,399,199 | B2 | 3/2013 | Makarov et al. |
| 8,420,319 | B2 | 4/2013 | Mikawa |
| 8,697,359 | B1 | 4/2014 | Zhang |
| 8,728,737 | B2 | 5/2014 | Makarov et al. |
| 9,163,284 | B2 | 10/2015 | Iliu |
| 9,322,006 | B2 | 4/2016 | Liu et al. |
| 9,322,037 | B2 | 4/2016 | Liu et al. |
| 9,512,446 | B1 | 12/2016 | Joung et al. |
| 9,752,132 | B2 | 9/2017 | Joung et al. |
| 9,822,407 | B2 | 11/2017 | Joung |
| 9,850,484 | B2 | 12/2017 | Joung |
| 9,926,546 | B2 | 3/2018 | Joung et al. |
| 9,988,674 | B2 | 6/2018 | Joung |
| 10,000,772 | B2 * | 6/2018 | Doudna ................. C12Q 1/686 |
| 10,093,910 | B2 | 10/2018 | Joung et al. |
| 10,266,850 | B2 | 4/2019 | Doudna et al. |
| 10,501,794 | B2 | 12/2019 | Joung |
| 10,526,591 | B2 | 1/2020 | Joung et al. |
| 10,633,642 | B2 | 4/2020 | Joung et al. |
| 2006/0292611 | A1 | 12/2006 | Berka et al. |
| 2009/0082295 | A1 | 3/2009 | Jungneli et al. |
| 2010/0076057 | A1 | 3/2010 | Sontheimer et al. |
| 2010/0317722 | A1 | 12/2010 | Lavon |
| 2011/0060493 | A1 | 3/2011 | Miura et al. |
| 2011/0189776 | A1 | 8/2011 | Terns et al. |
| 2011/0207221 | A1 | 8/2011 | Cost et al. |
| 2011/0223638 | A1 | 9/2011 | Wiedenheft et al. |
| 2011/0281736 | A1 | 11/2011 | Drmanac et al. |
| 2011/0287545 | A1 | 11/2011 | Cost |
| 2013/0130248 | A1 | 5/2013 | Haurwitz et al. |
| 2013/0137605 | A1 | 5/2013 | Shendure et al. |
| 2013/0143204 | A1 | 6/2013 | Von Kalle |
| 2013/0303461 | A1 | 11/2013 | Iafrate et al. |
| 2013/0309668 | A1 | 11/2013 | Makarov et al. |

(Continued)

FOREIGN PATENT DOCUMENTS

| | | |
|---|---|---|
| CA | 3069296 | 1/2019 |
| CN | 104854241 | 8/2015 |

(Continued)

OTHER PUBLICATIONS

Kleinstiver et al. Engineered CRISPR-Cas9 nucleases with altered PAM specificities 2015. Nature Letters. vol. 523, pp. 481-497 (Year: 2015).*
U.S. Appl. No. 61/652,086, Jinek et al., filed May 25, 2012.
Abudayyeh et al., "A Cytosine Deaminase for Programmable Single-base RNA Editing," Science, Jul. 26, 2019, 365(6451):382-386, 9 pages.

(Continued)

*Primary Examiner* — Celine X Qian
*Assistant Examiner* — Tiffany Nicole Grooms
(74) *Attorney, Agent, or Firm* — Fish & Richardson P.C.

(57) ABSTRACT

Engineered CRISPR-Cas9 nucleases with altered and improved PAM specificities and their use in genomic engineering, epigenomic engineering, and genome targeting.

25 Claims, 11 Drawing Sheets

Specification includes a Sequence Listing.

(56) References Cited

U.S. PATENT DOCUMENTS

| | | |
|---|---|---|
| 2014/0024542 A1 | 1/2014 | Richards |
| 2014/0068797 A1 | 3/2014 | Doudna et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234289 A1 | 8/2014 | Liu et al. |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sastry-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0357530 A1 | 12/2014 | Zhang et al. |
| 2014/0377868 A1 | 12/2014 | Joung et al. |
| 2015/0024500 A1 | 1/2015 | Yu et al. |
| 2015/0031134 A1 | 1/2015 | Zhang et al. |
| 2015/0045546 A1 | 2/2015 | Siksnys et al. |
| 2015/0050699 A1 | 2/2015 | Siksnys et al. |
| 2015/0071899 A1 | 3/2015 | Liu et al. |
| 2015/0044191 A1 | 5/2015 | Liu et al. |
| 2016/0208243 A1 | 7/2016 | Zhang et al. |
| 2016/0304950 A1 | 10/2016 | Joung |
| 2017/0058271 A1 | 3/2017 | Joung et al. |
| 2017/0073747 A1 | 3/2017 | Joung |
| 2017/0081650 A1 | 3/2017 | Joung et al. |
| 2017/0088833 A1 | 3/2017 | Joung |
| 2017/0198344 A1 | 7/2017 | Vaisvila et al. |
| 2017/0233756 A1 | 8/2017 | Begemann et al. |
| 2018/0073012 A1 | 3/2018 | Liu |
| 2018/0087104 A1 | 3/2018 | Joung |
| 2018/0100148 A1 | 4/2018 | Vakulskas et al. |
| 2018/0216088 A1 | 8/2018 | Joung et al. |
| 2018/0245071 A1 | 8/2018 | Joung |
| 2018/0265920 A1 | 9/2018 | Joung |
| 2018/0282714 A1 | 10/2018 | Joung et al. |
| 2018/0320201 A1 | 11/2018 | Vakulskas et al. |
| 2019/0071657 A1 | 3/2019 | Joung et al. |
| 2019/0106687 A1 | 4/2019 | Joung |
| 2019/0177710 A1* | 6/2019 | Lee ................... C12N 15/11 |
| 2019/0382775 A1 | 12/2019 | Tan et al. |
| 2020/0010889 A1 | 1/2020 | Joung et al. |
| 2020/0131536 A1 | 4/2020 | Kim |
| 2020/0140835 A1 | 5/2020 | Joung et al. |
| 2020/0149024 A1 | 5/2020 | Joung et al. |
| 2020/0199665 A1 | 6/2020 | Joung |
| 2020/0239930 A1 | 7/2020 | Joung et al. |
| 2020/0277586 A1* | 9/2020 | Nureki .................. C12N 9/22 |
| 2021/0071248 A1 | 3/2021 | Joung et al. |
| 2021/0261932 A1 | 8/2021 | Kleinstiver et al. |
| 2021/0284978 A1 | 9/2021 | Kleinstiver et al. |
| 2021/0355465 A1 | 11/2021 | Joung et al. |

FOREIGN PATENT DOCUMENTS

| | | |
|---|---|---|
| CN | 105543195 | 5/2016 |
| CN | 106062197 | 10/2016 |
| EP | 3530737 | 8/2019 |
| JP | 2015-521468 | 7/2015 |
| JP | 2018-530536 | 10/2018 |
| WO | WO 2008/108989 | 9/2008 |
| WO | WO 2010/054108 | 5/2010 |
| WO | WO 2011/086118 | 7/2011 |
| WO | WO 2011/100058 | 8/2011 |
| WO | WO 2012/065143 | 5/2012 |
| WO | WO 2012/164565 | 12/2012 |
| WO | WO 2013/078470 | 5/2013 |
| WO | WO 2013/098244 | 7/2013 |
| WO | WO 2013/176772 | 11/2013 |
| WO | WO 2013/191775 | 12/2013 |
| WO | WO 2014/018080 | 1/2014 |
| WO | WO 2014/071070 | 5/2014 |
| WO | WO 2014/071361 | 5/2014 |
| WO | WO 2014/093701 | 6/2014 |
| WO | WO 2014/124284 | 8/2014 |
| WO | WO 2014/144288 | 9/2014 |
| WO | WO 2014/144592 | 9/2014 |
| WO | WO 2014/152432 | 9/2014 |
| WO | WO 2014/191521 | 12/2014 |
| WO | WO 2014/204724 | 12/2014 |
| WO | WO 2014/204725 | 12/2014 |
| WO | WO 2015/089364 | 6/2015 |
| WO | WO 2015/089473 | 6/2015 |
| WO | WO 2015/089486 | 6/2015 |
| WO | WO 2015/117040 | 8/2015 |
| WO | WO 2015/200378 | 12/2015 |
| WO | WO 2016/115179 | 7/2016 |
| WO | WO 2016/115355 | 7/2016 |
| WO | WO 2016/141224 | 9/2016 |
| WO | WO 2016/205613 | 12/2016 |
| WO | WO 2017/015015 | 1/2017 |
| WO | WO 2017/040348 | 3/2017 |
| WO | WO 2017/059313 | 4/2017 |
| WO | WO 2017/070633 | 4/2017 |
| WO | WO-2017070633 A2 * | 4/2017 ............. A61P 31/18 |
| WO | WO 2017/079593 | 5/2017 |
| WO | WO 2017/081288 | 5/2017 |
| WO | WO 2017/184768 | 10/2017 |
| WO | WO 2018/052247 | 3/2018 |
| WO | WO 2018/119359 | 6/2018 |
| WO | WO 2018/218166 | 11/2018 |
| WO | WO 2018/218188 | 11/2018 |
| WO | WO 2019/009682 | 1/2019 |
| WO | WO 2019/040650 | 2/2019 |
| WO | WO 2019/075197 | 4/2019 |
| WO | WO 2019/092042 | 5/2019 |
| WO | WO 2019/217943 | 11/2019 |
| WO | WO 2020/041751 | 2/2020 |
| WO | WO 2021/042047 | 3/2021 |

OTHER PUBLICATIONS

Al-Attar et al., "Clustered Regularly Interspaced Short Palindromic Repeats (CRISPRs): The Hallmark of an Ingenious Antiviral Defense Mechanism in Prokaryotes," Biol Chem., 2011, 392(4):277-289.

Anders et al., "4un3: Crystal structure of Cas9 bound to PAM-containing DNA target," RCSB Protein Data Bank, May 25, 2014, retrieved on May 6, 2016, retrieved from URL <http://www.rcsb.org/pdb/explore/explore.do?structureId=4U>, 3 pages.

Anders et al., "Structural basis of PAM-dependent target DNA recognition by the Cas9 endonuclease," Nature, 2014, 513:569-573, 16 pages.

Anders et al., "Structural Plasticity of PAM Recognition by Engineered Variants of the RNA-Guided Endonuclease Cas9," Molecular Cell, Mar. 17, 2016, 61(6):895-902.

(56) References Cited

OTHER PUBLICATIONS

AU Office Action in Australian Application No. 2015280069, dated Nov. 6, 2020, 6 pages.
AU Office Action in Australian Appln. No. 2016226077, dated May 21, 2021, 5 pages.
Aynaud et al., "Human Tribbles 3 protects nuclear DNA from cytidine deamination by APOBEC3A." Journal of Biological Chemistry, Nov. 2012, 287(46):39182-39192.
Balemans et al., "Increased bone density in sclerosteosis is due to the deficiency of a novel secreted protein (SOST)," Hum Mol Genet., 2001, 10(5):537-543.
Barrangou & May, "Unraveling the potential of CRISPR-Cas9 for gene therapy," Expert Opin. Biol. Ther., 2014, 15:311-314.
Belanger et al., "Deamination intensity profiling of human APOBEC3 protein activity along the near full-length genomes of HIV-1 and MoMLV by HyperHRM analysis," Virology, Jan. 2014, 448:168-175.
Berg et al., "Section 7.1. Homologs are Descended from a Common Ancestor," in Biochemistry, W.H. Freeman, pub. 2002, [retrieved on Jan. 30, 2017]. Retrieved from the Internet: URL <https://www.ncbi.nlm.nih.gov/books/NBK22355/>. 1 page.
Bikard et al., "Programmable repression and activation of bacterial gene expression using an engineered CRISPR-Cas system," Nucleic Acids Res., 2013, 41(15):7429-7437.
Bisaria et al., "Lessons from Enzyme Kinetics Reveal Specificity Principles for RNA-Guided Nucleases in RNA Interference and CRISPR-Based Genome Editing," Cell Syst., Jan. 2017, 4(1):21-29.
Bolukbasi et al., "Creating and evaluating accurate CRISPR-Cas9 scalpels for genomic surgery," Nat Meth, Jan. 2016, 13: 41-50.
Briggs et al., "Removal of deaminated cytosines and detection of in vivo methylation in ancient DNA," Nucleic Acids Research, Apr. 2010, 38(6):e87, 12 pages.
Cameron et al., "Mapping the genomic landscape of CRISPR-Cas9 cleavage," Nature Methods, 2017, 10 pages.
Canela et al., "DNA Breaks and End Resection Measured Genomewide by End Sequencing," Molecular Cell, 2016, 63: 1-14.
Canver et al., "BCL11A enhancer dissection by Cas9-mediated in situ saturating mutagenesis," Nature., 2015, 527(7577), 192-7, 23 pages.
Carroll, "A CRISPR Approach to Gene Targeting," Molecular Therapy, Sep. 2012, 20:(9)1658-1660.
Casini et al., "A highly specific SpCas9 variant is identified by in vivo screening in yeast," Nat. Biotechnol., 2018, 36(3):265-271, 11 pages.
Cencic et al., "Protospacer Adjacent Motif (PAM)-Distal Sequences Engage CRISPR Cas9 DNA Target Cleavage," Oct. 2014, PLOS One, 9(10):e109213, 13 pages.
Chavez et al., "Highly-efficient Cas9-mediated transcriptional programming," Nat. Meth., Apr. 2015, 12(4):326-328.
Chen & Zhao, "A highly sensitive selection method for directed evolution of homing endonucleases," Nucleic Acids Res., 2005, 33(18):e154, 7 pages.
Chen et al., "Enhanced proofreading governs CRISPR-Cas9 targeting accuracy," Nature, Oct. 2017, 550(7676):407-410, 22 pages.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232, 3 pages.
Choi & Meyerson, "Targeted genomic rearrangements using CRISPR/Cas technology," Nat Commun., Apr. 24, 2014, 5:3728, 9 pages.
Chu et al., "Rationally Designed Base Editors for Precise Editing of the Sickle Cell Disease Mutation," The CRISPR Journal, Apr. 20, 2021, 4(2):169-177.
Chylinski et al., "The tracrRNA and Cas9 families of type II CRISPR-Cas immunity systems," RNA Biol., May 2013, 10:726-737.
Clement et al., "CRISPResso2 provides accurate and rapid genome editing sequence analysis," Nature Biotechnology, Feb. 2019, 37:224-226, 3 pages.
CN Office Action in Chinese Appln. No. 201580045542, dated Jul. 14, 2020, 29 pages (with English translation).
CN Office Action in Chinese Appln. No. 201580045542.3, dated Feb. 3, 2020, 19 pages (with English translation).
CN Office Action in Chinese Appln. No. 201580045542.3, dated Jul. 22, 2019, 25 pages (with English translation).
CN Office Action in Chinese Appln. No. 201680024041.1, dated Jul. 6, 2020, 19 pages (with English translation).
CN Office Action in Chinese Appln. No. 201680024041.1, dated Mar. 18, 2021, 11 pages (with English translation).
CN Office Action in Chinese Appln. No. 201680063266.8, dated Dec. 11, 2020, 15 pages (with English translation).
Cong et al., "Multiplex genome engineering using CRISPR/Cas systems," Science, 2013, 339:819-823 (Author Manuscript).
Courtney et al., "CRISPR/Cas9 DNA cleavage at SNP-derived PAM enables both in vitro and in vivo KRT12 mutation-specific targeting," Gene Ther., 2016, 23(1):108-12.
Cox et al., "Congenital insensitivity to pain: novel SCN9A missense and in-frame deletion mutations," Hum Mutat., 2010, 31:E1670-86.
Cox et al., "Therapeutic genome editing: prospects and challenges," Nat Med, 2015, 21: 121-131.
Cradick et al., "CRISPR/Cas9 systems targeting beta-globin and CCR5 genes have substantial off-target activity," Nucleic Acids Res., 2013, 41(20):9584-92.
Crosetto et al., "Nucleotide-resolution DNA double-strand break mapping by next-generation sequencing," Apr. 2013, Nat Methods 10(4): 361-365.
Dagdas et al., "A Conformational Checkpoint Between DNA Binding and Cleavage by CRISPR-Cas9," Science Advances, Aug. 2017, 3(8): eaao0027.
Deltcheva et al., "CRISPR RNA maturation by trans-encoded small RNA and host factor RNase III," Nature, 2011, 471(7340):602-607 (Author Manuscript).
Deveau et al., "Phage response to CRISPR-encoded resistance in *Streptococcus thermophilus*," J Bacteriol., 2008, 190(4):1390-400.
Dicarlo et al., "Genome engineering in *Saccharomyces cerevisiae* using CRISPR-Cas systems," Nucleic Acids Res, 2013, 1-8.
Ding et al., "Enhanced efficiency of human pluripotent stem cell genome editing through replacing TALENs with CRISPRs," Cell Stem Cell., Apr. 2013, 12(4):393-4 (Author Manuscript).
Doench et al., "Optimized sgRNA design to maximize activity and minimize off-target effects of CRISPR-Cas9," Nature Biotechnology, Jan. 18, 2016, 34:184-191, 12 pages.
Dong et al., "The crystal structure of Cpf1 in complex with CRISPR RNA," Nature, 2016, 532(7600):522-526, 16 pages.
Doudna & Charpentier, "The new frontier of genome engineering with CRISPR-Cas9," Science, Nov. 2014, 346(6213):1258096, 10 pages.
Doyon et al., "Directed evolution and substrate specificity profile of homing endonuclease I-Scel," J. Am. Chem. Soc., 2006, 128:2477-2484.
Duan et al., "Genome-wide identification of CRISPR/Cas9 off-targets in human genome," Cell Res, 2014, 24(8):1009-1012, 4 pages.
Elliott et al., "Gene Conversion Tracts from Double-Strand Break Repair in Mammalian Cells, " Mol Cell Biol., 1998, 18:93-101.
EP Extended European Search Report in European Appln. No. 15812186.3, dated Oct. 19, 2017, 7 pages.
EP Extended European Search Report in European Appln. No. 16759521.4, dated Jul. 31, 2018, 10 pages.
EP Extended European Search Report in European Appln. No. 16842722.7, dated Jun. 7, 2019, 11 pages.
EP Extended European Search Report in European Appln. No. 16845183.9, dated Jan. 18, 2019, 11 pages.
EP Extended European Search Report in European Appln. No. 16852752.1, dated Feb. 20, 2019, 11 pages.
EP Extended European Search Report in European Appln. No. 18848977.7, dated Aug. 27, 2021, 8 pages.
EP Extended European Search Report in European Appln. No. 20216630.2, dated Jun. 21, 2021, 8 pages.

(56) References Cited

OTHER PUBLICATIONS

EP Office Action in European Appln. No. 15812186.3, dated Aug. 28, 2019, 4 pages.
EP Office Action in European Appln. No. 15812186.3, dated Jun. 15, 2018, 4 pages.
EP Office Action in European Appln. No. 16759521.4, dated Jan. 3, 2020, 4 pages.
EP Office Action in European Appln. No. 16842722, dated Sep. 30, 2020, 4 pages.
EP Office Action in European Appln. No. 16842722.7, dated Mar. 5, 2020, 5 pages.
EP Office action in European Appln. No. 16845183, dated Jun. 9, 2020, 7 pages.
EP Office Action in European Appln. No. 16852752.1, dated Jan. 29, 2020, 4 pages.
EP Office Action in European Appln. No. 16852752.1, dated Nov. 3, 2020, 5 pages.
EP Partial Supplementary Search Report in European Appln. No. 16842722.7, dated Mar. 7, 2019, 12 pages.
Esvelt et al., "Orthogonal Cas9 proteins for RNA-guided gene regulation and editing," Nat. Methods, 2013, 10:1116-1121.
Findlay et al., "Saturation editing of genomic regions by multiplex homology-directed repair," Nature, 2014, 513:120-3.
Flannick et al., "Loss-of-function mutations in SLC30A8 protect against type 2 diabetes," Nat Genet., 2014, 46:357-63.
Fonfara et al., "Phylogeny of Cas9 determines functional exchangeability of dual-RNA and Cas9 among orthologous type II CRISPR-Cas systems." Nucleic Acids Res., 2014, 42(4): 2577-2590.
Frock et al., "Genome-wide detection of DNA double-stranded breaks induced by engineered nucleases," Nat Biotechnol, Feb. 2015, 33: 179-186.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat. Biotechnol, Mar. 2014, 32(3):279-284, 8 pages.
Gabriel et al., "An unbiased genome-wide analysis of zinc-finger nuclease specificity," Nat Biotechnol., 2011, 29:816-823.
Gagnon et al., "Efficient mutagenesis by Cas9 protein-mediated oligonucleotide insertion and large-scale assessment of single-guide RNAs," PLoS One, 2014, 9, e98186.
Gaj et al., "ZFN, TALEN and CRISPR/Cas-based methods for genome engineering," Trends Biotechnol,, Jul. 2013, 31(7):397-405.
Gao et al., "Engineered Cpf1 variants with altered PAM specificities," Nat Biotechnol., 2017, 35:789-792, 6 pages.
Gasiunas et al., "Cas9-crRNA ribonucleoprotein complex mediates specific DNA cleavage for adaptive immunity in bacteria," Proc Natl Acad Sci USA, 2012, 109(39):E2579-E2586.
Gaudelli et al., "Programmable base editing of A•T to G•C in genomic DNA without DNA cleavage," Nature, Nov. 23, 2017, 551:464-471.
Gehrke et al., "An APOBEC3A-Cas9 base editor with minimized bystander and off-target activities," Nature Biotechnology, Nov. 2018, 36(10):977-982, 8 pages.
GenBank Accession No. AKS40380.1, "Cas9 [Synthetic plasmid pFC330], " Aug. 2, 2015, 2 pages.
GenBank Accession No. EOS46485.1, "The Genome Sequence of Lachnospiraceae bacterium COE1," May 29, 2013, 2 pages.
GenBank Accession No. NP_472073, "hypothetical protein lin2744 [listeria innocua Clip11262]," Dec. 17, 2014, 2 pages.
GenBank Accession No. WP_010922251.1, "type II CRISPR RNA-guided endonuclease Cas9 [*Streptococcus pyogenes*]," Oct. 7, 2015, 2 pages.
Ghezraoui et al., "Chromosomal translocations in human cells are generated by canonical nonhomologous end-joining," Mol Cell, Sep. 18, 2014, 55: 829-842.
Gnirke et al., "Solution hybrid selection with ultra-long oligonucleotides for massively parallel targeted sequencing," Nature Biotechnology, 2009, 27: 182-189.
Gori et al., "Delivery and Specificity of CRISPR-Cas9 Genome Editing Technologies for Human Gene Therapy," Hum Gene Ther, 2015, 26: 443-451.
Gostissa et al., "IgH class switching exploits a general property of two DNA breaks to be joined in cis over long chromosomal distances," Proc Natl Acad Sci, Feb. 18, 2014, 111(7): 2644-2649.
Grünewald et al., "CRISPR DNA Base Editors with Reduced RNA Off-Target and Self-Editing Activities," Nature Biotechnology, Sep. 2, 2019, 37(9):1041-1048, 10 pages.
Grünewald et al., "Transcriptome-wide off-target RNA editing induced by CRISPR-guided DNA base editors," Nature, May 16, 2019, 569(7756):433-437, 18 pages.
Guilinger et al., "Broad specificity profiling of TALENs results in engineered nucleases with improved DNA-cleavage specificity," Nat. Meth., Apr. 2014, 11(4):429-435.
Guilinger et al., "Fusion of Catalytically Inactive Cas9 to FokI Nuclease Improves the Specificity of Genome Modification," Nat Biotechnol., Apr. 2014, 32:577-582, 7 pages.
Guo et al., "Structural insights into a high fidelity variant of SpCas9," Cell Res., 2019, 29:183-192, 10 pages.
Hale et al., "Essential Features and Rational Design of CRISPR RNAs That Function With the Cas RAMP Module Complex to Cleave RNAs," Mol Cell., Feb. 2012, 45(3):292-302.
Harper et al., "Protective alleles and modifier variants in human health and disease," Nat Rev Genetics, 2015, 16:689-701, 13 pages.
Heigwer et al., "E-CRISP: fast CRISPR target site identification," Nat Methods, Feb. 2014, 11: 122-123.
Heler et al., "Cas9 specifies functional viral targets during CRISPR-Cas adaptation," Nature, 2015, 519:199-202, 16 pages.
Hirano et al., "Structural Basis for the Altered PAM Specificities of Engineered CRISPR-Cas9," Mol Cell, Mar. 2017, 61:886-94.
Holtz et al., "APOBEC3G cytosine deamination hotspots are defined by both sequence context and single-stranded DNA secondary structure," Nucleic Acids Research, Jul. 2013, 41(12):6139-6148.
Horvath et al., "Diversity, activity, and evolution of CRISPR loci in *Streptococcus thermophilus*," J. Bacteriol., Feb. 2008, 190:1401-1412.
Hou et al., "Efficient genome engineering in human pluripotent stem cells using Cas9 from Neisseria meningitidis," Proc. Natl. Acad. Sci. USA, Sep. 2013, 110(39):15644-15649.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Hu et al., "Evolved Cas9 variants with broad PAM compatibility and high DNA specificity," Nature, 2018, 556:57-63.
Hwang et al., "Efficient In Vivo Genome Editing Using RNA-Guided Nucleases," Nat Biotechnol., 2013, 31:227-229 (Author Manuscript).
IL Office Action In Israeli Appln. No. 249555, dated Dec. 16, 2019, 6 pages (with English translation).
IL Office Action In Israeli Appln. No. 257955, dated May 1, 2020, 6 pages (with English translation).
IN Office Action in Indian Application No. 201617043121, dated Dec. 8, 2020, 6 pages.
Ishino et al., "Identification of a mismatch-specific endonuclease in hyperthermophilic Archaea," Nucleic Acids Res., Apr. 2016, 44(7):2977-2986.
Iyer et al., "Prediction of novel families of enzymes involved in oxidative and other complex modifications of bases in nucleic acids," Cell Cycle, 2009, 8(11):1698-710.
Jiang et al., "A Cas9-guide RNA complex preorganized for target DNA recognition," Science, Jun. 2015, 348(6242):1477-1481.
Jiang et al., "Characterization of *Escherichia coli* Endonuclease VIII," J. Biol. Chem, 1997, 272:32230-32239.
Jiang et al., "CRISPR-assisted editing of bacterial genomes," Nat Biotechnol., 2013, 31:233-239 (Author Manuscript).
Jiang et al., "Structures of a CRISPR-Cas9 R-loop complex primed for DNA cleavage," Science, Feb. 2016, 351(6275):867-871.

(56) References Cited

OTHER PUBLICATIONS

Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 endonucleases reveal RNA-mediated conformational activation," Science, Mar. 2014, 343(6176):1247997, 13 pages.
JP Office Action in Japanese Appln. No. 2016-575174, dated Jul. 9, 2019, 12 pages (with English translation).
JP Office Action in Japanese Appln. No. 2016-575174, dated May 12, 2020, 6 pages (with English translation).
JP Office Action in Japanese Appln. No. 2017-546196, dated Feb. 25, 2020, 10 pages (with English translation).
JP Office Action in Japanese Appln. No. 2018-513347, dated Sep. 15, 2020, 11 pages (with English translation).
JP Office Action in Japanese Appln. No. 2018-516489, dated Jul. 21, 2020, 8 pages (with English translation).
Kan et al., "Mechanisms of precise genome editing using oligonucleotide donors," Genome Res., 2017, 27:1099-1111.
Karvelis et al., "Rapid characterization of CRISPR-Cas9 protospacer adjacent motif sequence elements," Genome Biol., 2015, 16:253, 13 pages.
Keegan et al., "ADAR RNA editing below the backbone," RNA, Sep. 2017, 23(9):1317-1328.
Kim et al., "Deep learning improves prediction of CRISPR-Cpf1 guide RNA activity," Nature Biotechnology, Jan. 29, 2018, 36:239-241, 6 pages.
Kim et al., "Digenome-seq: genome-wide profiling of CRISPR-Cas9 off-target effects in human cells," Nat Meth, Mar. 2015, 12: 237-243.
Kim et al., "Genome-wide target specificities of CRISPR RNA-guided programmable deaminases," Nat. Biotech., May 2017, 35(5):475-480.
Kim et al., "Genome-wide target specificities of CRISPR-Cas9 nucleases revealed by multiplex Digenome-seq," Genome Res, 2016, 26: 406-415.
Kim et al., "Genome-wide target specificity of CRISPR RNA-guided adenine base editors," Nature Biotechnology, Apr. 2019, 37(4):430-435.
Kim et al., "Increasing the genome-targeting scope and precision of base editing with engineered Cas9-cytidine deaminase fusions," Nat Biotechnol., Apr. 2017, 35(4):371-376.
Kim et al., "SpCas9 activity prediction by DeepSpCas9, a deep learning-based model with high generalization performance," Science Advances, Nov. 6, 2019, 5(11):eaax9249, 9 pages.
Kleinstiver et al., "A unified genetic, computational and experimental framework identifies functionally relevant residues of the homing endonuclease I-BmoI," Nucleic Acids Res., 2010, 38(7):2411-2427.
Kleinstiver et al., "Broadening the targeting range of Staphylococcus aureus CRISPR-Cas9 by modifying PAM recognition," Nature Biotechnology, Dec. 2015, 33(12):1293-1298.
Kleinstiver et al., "Engineered CRISPR-Cas12a variants with increased activities and improved targeting ranges for gene, epigenetic and base editing," Nat Biotechnol., Feb. 11, 2019, 37:276-282.
Kleinstiver et al., "Engineered CRISPR-Cas9 nucleases with altered PAM specificities," Nature, Jul. 2015, 523(7561):481-485.
Kleinstiver et al., "High-fidelity CRISPR-Cas9 nucleases with no detectable genome-wide off-target effects," Nature, Jan. 2016, 529:490-495, 17 pages.
Kleinstiver et al., "Supplementary Materials: Engineered CRISPR-Cas9 nucleases with altered PAM specificities," Nature, Jul. 2015, 523(7561):481-497, 289 pages.
Koblan et al., "Improving cytidine and adenine base editors by expression optimization and ancestral reconstruction," Nat Biotechnol., Oct. 2018, 36:843-846.
Komor et al., "Improved base excision repair inhibition and bacteriophage Mu Gam protein yields C:G-to-T:A base editors with higher efficiency and product purity," Sci. Adv., Aug. 2017, 3:eaao4774, 9 pages.
Komor et al., "CRISPR-Based Technologies for the Manipulation of Eukaryotic Genomes," Cell, Jan. 12, 2017, 168(1-2):20-36.
Komor et al., "Programmable editing of a target base in genomic DNA without double-stranded DNA cleavage," Nature, May 2016, 533(7603):420-424.
Kuraoka, "Diversity of Endonuclease V: From DNA Repair to RNA Editing" Biomolecules, Dec. 2015, 5(4):2194-2206.
Kuscu et al., "Genome-wide analysis reveals characteristics of off-target sites bound by the Cas9 endonuclease," Nat Biotechnol, Jul. 2014, 32 (7): 677-683.
Lazzarotto et al., "Defining CRISP-Cas9 genome-wide nuclease activities with CIRCLE-seq," Nature Protocols, Oct. 2018, 13: 2615-2642.
Liang et al., "Genome-wide profiling of adenine base editor specificity by Endo V-seq," Nature Communications, Jan. 2019, 10(1):67, 9 pages.
Liang et al., "Off-target effects of cytidine base editor and adenine base editor: What can we do?," Journal of Genetics and Genomics, 2019, 46:509-512.
Lin et al., "CRISPR/Cas9 systems have off-target activity with insertions or deletions between target DNA and guide RNA sequences," Nucleic Acids Res., 2014, 42:7473-7485.
Lindahl et al., "DNA N-glycosidases: properties of uracil-DNA glycosidase from Escherichia coli," J. Biol. Chem., May 1977, 252:3286-3294.
Lindahl, "DNA repair enzymes," Annu. Rev. Biochem, 1982, 51:61-64.
Makarova et al., "Evolution and classification of the CRISPR-Cas systems," Nat. Rev. Microbiol., 2011, 9(6):467-77.
Mali et al., "Cas9 as a versatile tool for engineering biology," Nature Methods, 2013, 10(10):957-963.
Mali et al., "CAS9 transcriptional activators for target specificity screening and paired nickases for cooperative genome engineering," Nat Biotechnol, Sep. 2013, 31(9): 833-838.
Mali et al., "RNA-guided human genome engineering via Cas9," Science, Feb. 2013, 339:823-826 (Author Manuscript).
Marx et al., "Gene editing: how to stay on-target with CRISPR," Nat Methods, 2014, 11:1021-1026.
McShan et al., "Genome sequence of a nephritogenic and highly transformable M49 strain of Streptococcus pyogenes," J. Bacteriol., 2008, 190:7773-7785.
Melamede et al., "Isolation and characterization of endonuclease VIII from Escherichia coli," Biochemistry, Feb. 1994, 33:1255-1264.
Miller et al. "A Tale nuclease architecture for efficient genome editing," Nat. Biotech., Feb. 2011, 29(2):143-150.
Mojica et al., "Short motif sequences determine the targets of the prokaryotic CRISPR defence system," Microbiology, Jan. 2009, 155:733-740.
Mullis and Faloona, "Specific synthesis of DNA in vitro via a polymerase-catalyzed chain reaction," Methods in Enzymology, 1987, 155: 335-350.
Nhm.ac.uk [online], "Blunting of DNA," Nov. 11, 2012, retrieved on Apr. 14, 2020, retrieved from URL <https://www.nhm.ac.uk/content/dam/nhmwww/our-science/dpts-facilities-staff/Coreresearchlabs/blunting-of-dna_aug12.pdf>, 1 page.
Nishida et al., "Targeted nucleotide editing using hybrid prokaryotic and vertebrate adaptive immune systems," Science, Sep. 2016, 53(6305), 14 pages.
Nishimasu et al., "Crystal structure of Cas9 in complex with guide RNA and target DNA," Cell, 2014, 156:935-949.
Nishimasu et al., "Engineered CRISPR-Cas9 nuclease with expanded targeting space," Science, Sep. 21, 2018, 361(6408):1259-1262.
Ochman et al., "Genetic Applications of an Inverse Polymerase Chain Reaction," Genetics, Nov. 1998, 120:621-623.
Office Action in Australian Appln. No. 2018320865, dated Nov. 25, 2022, 4 pages.
Office Action in Chinese Appln. No. 201880068905.9, dated Dec. 30, 2022, 22 pages (with English translation).

(56) References Cited

OTHER PUBLICATIONS

Office Action in Japanese Appln. No. 2020-511253, dated Apr. 4, 2023, 15 pages (with English translation).

Office Action in Japanese Appln. No. 2020-511253, dated Aug. 2, 2022, 19 pages (with English translation).

Oliphant et al., "Defining the sequence specificity of DNA-binding proteins by selecting binding sites from random-sequence oligonucleotides: analysis of yeast GCN4 protein," Mol. Cell. Biol., Jul. 1989, 9(7):2944-2949.

Orlando et al., "Zinc-finger nuclease-driven targeted integration into mammalian genomes using donors with limited chromosomal homology," Nucleic Acids Res, 2010, 38(15): e152.

Osborn et al., "TALEN-based gene correction for epidermolysis bullosa," Mol Ther, 2013, 21: 1151-1159.

Pattanayak et al., "High-throughput profiling of off-target DNA cleavage reveals RNA-programmed Cas9 nuclease specificity," Nat Biotechnol., 2013, 31:839-843 (Author Manuscript).

Pattanayak et al., "Revealing off-target cleavage specificities of zinc-finger nucleases by in vitro selection," Nat. Meth., 2011, 8(9):765-770.

PCT International Preliminary Report on Patentability in International Appln. No. PCT/US2016/020756, dated Sep. 14, 2017, 8 pages.

PCT International Preliminary Report on Patentability in International Appln. No. PCT/US2016/049147, dated Mar. 6, 2018, 8 pages.

PCT International Preliminary Report on Patentability in International Appln. No. PCT/US2016/051097, dated Mar. 13, 2018, 10 pages.

PCT International Preliminary Report on Patentability in International Appln. No. PCT/US2016/054912, dated Apr. 12, 2018, 10 pages.

PCT International Preliminary Report on Patentability in International Appln. No. PCT/US2018/036293, dated Dec. 10, 2019, 8 pages.

PCT International Preliminary Report on Patentability in International Appln. No. PCT/US2018/047577, dated Feb. 25, 2020, 8 pages.

PCT International Preliminary Report on Patentability in International Appln. No. PCT/US2018/055406, dated Apr. 14, 2020, 8 pages.

PCT International Search Report and Written Opinion in International Appln. No. PCT/US2015/037269, dated Oct. 15, 2015, 26 pages.

PCT International Search Report and Written Opinion in International Appln. No. PCT/US2016/020756, dated Jul. 26, 2016, 12 pages.

PCT International Search Report and Written Opinion in International Appln. No. PCT/US2016/049147, dated Dec. 23, 2016, 12 pages.

PCT International Search Report and Written Opinion in International Appln. No. PCT/US2016/051097, dated Jan. 24, 2017, 12 pages.

PCT International Search Report and Written Opinion in International Appln. No. PCT/US2016/054912, dated Jan. 24, 2017, 12 pages.

PCT International Search Report and Written Opinion in International Appln. No. PCT/US2017/043753, dated Dec. 28, 2017, 18 pages.

PCT International Search Report and Written Opinion in International Appln. No. PCT/US2018/028919, dated Oct. 1, 2018, 17 pages.

PCT International Search Report and Written Opinion in International Appln. No. PCT/US2018/036293, dated Nov. 8, 2018, 13 pages.

PCT International Search Report and Written Opinion in International Appln. No. PCT/US2018/055406, dated Jan. 17, 2019, 10 pages.

PCT International Search Report and Written Opinion in International Appln. No. PCT/US2019/027788, dated Aug. 5, 2019, 19 pages.

PCT International Search Report and Written Opinion in International Appln. No. PCT/US2021/014900, dated Jul. 21, 2021, 12 pages.

PCT International Search Report and Written Opinion in International Appln. No. PCT/US2021/014933, dated Jul. 20, 2021, 12 pages.

PCT Invitation to Pay Additional Fees in International Appln. No. PCT/US2016/049147, dated Oct. 31, 2016, 2 pages.

Perez et al., "Establishment of HIV-1 resistance in CD4+ T cells by genome editing using zinc-finger nucleases," Nat. Biotechnol., Jul. 2008, 26(7):808-816.

Perez-Pinera et al., "RNA-guided gene activation by CRISPR-Case9-based transcription factors," Nat Methods, 2013, 10(10):973-976.

Pinello et al., "Analyzing CRISPR genome-editing experiments with CRISPResso," Nat. Biotechnol., Jul. 2016, 34(7): 695-697.

Ran et al., "Double Nicking by RNA-Guided CRISPR Cas9 for Enhanced Genome Editing Specificity," Cell, 2013, 154(6):1380-1389.

Ran et al., "Genome engineering using the CRISPR-Cas9 system," Nature Protocols, 2013, 8(11):2281-2308.

Ran et al., "In vivo genome editing using *Staphylococcus aureus* Cas9," Nature, 2015, 520:186-191.

Rebhandl et al., "AID/APOBEC Deaminases and Cancer." Oncoscience, Apr. 2015, 2(4):320-333.

Rees et al., "Base editing: precision chemistry on the genome and transcriptome of living cells," Nat. Rev. Genet., Dec. 2018, 19(12):770-788.

Reyon et al., "FLASH assembly of TALENs for high-throughput genome editing," Nat. Biotechnol., May 2012, 30(5):460-465.

Rohland et al., "Cost-effective, high-throughput DNA sequencing libraries for multiplexed target capture," Genome Research, Jan. 2012, 22:939-946.

Rutkauskas et al., "Directional R-Loop Formation by the CRISPR-Cas Surveillance Complex Cascade Provides Efficient Off-Target Site Rejection," Cell Rep., Mar. 2015, 10(9):1534-1543.

Sander et al., "CRISPR-Cas systems for editing, regulating and targeting genomes," Nat Biotechnol., Apr. 2014, 32(4):347-55.

Sander et al., "In silico abstraction of zinc finger nuclease cleavage profiles reveals an expanded landscape of off-target sites," Nucleic Acids Res., 2013, 41:e181.

Sang, "Prospects for transgenesis in the chick," Mechanisms of Development, Sep. 2004, 121:1179-1186.

Sapranauskas et al., "The *Streptococcus thermophilus* CRISPR/Cas system provides immunity in *Escherichia coli*," Nucleic Acids Res., Aug. 2011, 39(21):9275-9282.

Savva et al., "The ADAR protein family," Genome Biol., Dec. 2012, 13(12):252, 10 pages.

Schaub and Keller, "RNA editing by adenosine deaminases generates RNA and protein diversity," Biochimie, Aug. 2002, 84(8):791-803.

Schmidt et al., "High-resolution insertion-site analysis by linear amplification-mediated PCR (LAM-PCR)," Nat Methods, Dec. 2007, 4(12): 1051-1057.

Schuelke et al., "Myostatin Mutation Associated with Gross Muscle Hypertrophy in a Child," New Engl J Med., 2004, 350:2682-2688.

Shah et al., "Protospacer recognition motifs," RNA Biol., Feb. 2013, 10(5):891-899.

Shen et al., "Generation of gene-modified mice via Cas9/RNA-mediated gene targeting," Cell Res., 2013, 23(5):720-723.

Shi et al., "Discovery of cancer drug targets by CRISPR-Cas9 screening of protein domains," Nat Biotechnol., 2015, 33:661-7.

Shinohara et al., "APOBEC3B can impair genomic stability by inducing base substitutions in genomic DNA in human cells." Scientific Reports, Nov. 2012, 2(806), 10 pages.

Slaymaker et al., "Rationally engineered Cas9 nucleases with improved specificity," Science, Jan. 2016, 351(6268):84-88.

Sloan et al., "Detecting rare mutations and DNA damage with sequencing-based methods," Trends in Biotechnology, Jul. 2018, 36(7):729-740.

(56) References Cited

OTHER PUBLICATIONS

Smith et al., "Whole-genome sequencing analysis reveals high specificity of CRISPR/Cas9 and TALEN-based genome editing in human iPSCs," Cell Stem Cell, Jul. 3, 2014, 15(1):12-13.
Spencer et al., "Deep mutational scanning of S. pyogenes Cas9 reveals important functional domains," Scientific Reports, Dec. 4, 2017, 7(16836), 14 pages.
Sternberg et al., "Conformational control of DNA target cleavage by CRISPR-Cas9" Nature, 2015, 527:110-113.
Sternberg et al., "DNA interrogation by the CRISPR RNA-guided endonuclease Cas9," Nature, Jan. 2014, 507(7490):62-67.
Suspène et al., "Erroneous Identification of APOBEC3-edited Chromosomal DNA in Cancer Genomics," British Journal of Cancer, May 2014, 110(10):2615-2622.
Suspène et al., "Extensive editing of both hepatitis B virus DNA strands by APOBEC3 cytidine deaminases in vitro and in vivo." Proceedings of the National Academy of Sciences of the United States of America, Jun. 2005, 102(23):8321-8326.
Suspène et al., "Recovery of APOBEC3-edited human immunodeficiency virus G→ A hypermutants by differential DNA denaturation PCR." Journal of General Virology, Jan. 2005, 86(1):125-129.
Suzuki et al., "In vivo genome editing via CRISPR/Cas9 mediated homology-independent targeted integration," Nature, 2016, 540:144-149.
Szczelkun et al., "Direct observation of R-loop formation by single RNA-guided Cas9 and Cascade effector complexes," Proc. Natl. Acad. Sci. USA., 111(27):9798-9803.
TG and HDL Working Group of the Exome Sequencing Project, National Heart, Lung, and Blood Institute, "Loss-of-function mutations in APOC3, triglycerides, and coronary disease," New Engl J Med., 2014, 371:22-31.
Thakore et al., "Highly specific epigenome editing by CRISPR-Cas9 repressors for silencing of distal regulatory elements," Nat. Meth., Dec. 2015, 12(12):1143-1149.
The Myocardial Infarction Genetics Consortium Investigators, "Inactivating mutations in NPCIL1 and protection from coronary heart disease," New Engl J Med., 2014, 371:2072-82.
thermofisher.com [online], "PCR Methods-Top Ten Strategies," 2017, [retrieved on Feb. 1, 2017], Retrieved from the Internet: URL<https://www.thermofisher.com/us/en/home/life-science/cloning/cloning-learningcenter/invitrogen-school-of-molecular-biology/pcr-education/pcr-reagents-enzymes/pcr-methods.html>. 10 pages.
Tsai & Joung., "Defining and improving the genome-wide specificities of CRISPR-Cas9 nucleases," Nat. Rev. Genet., 2016, 17(5):300-312.
Tsai et al., "CIRCLE-seq: a highly sensitive in vitro screen for genome-wide CRISPR-Cas9 nuclease off-targets," Nature Methods, May 2017, 14: 607-614.
Tsai et al., "Dimeric CRISPR RNA-guided FokI nucleases for highly specific genome editing," Nat. Biotechnol., 2014, 32(6):569-576.
Tsai et al., "GUIDE-Seq enables genome-wide profiling of off-target cleavage by CRISPR-Cas nucleases," Nat Biotechnol, Feb. 2015, 33:187-197.
Tsai et al., "What's changed with genome editing?," Cell Stem Cell, Jul. 2014, 15(1):3-4.
UniProt Database Accession No. U5ULJ7, "Full=Csn1 family CRISPR-associated protein," Jan. 22, 2014, 1 page.

Vakulskas et al., "A high-fidelity Cas9 mutant delivered as a ribonucleoprotein complex enables efficient gene editing in human haematopoietic stem and progenitor cells," Nature Medicine, Aug. 2018, 24(8):1216-1224.
Veres et al., "Low incidence of off-target mutations in individual CRISPR-Cas9 and TALEN targeted human stem cell clones detected by whole-genome sequencing," Cell Stem Cell, Jul. 3, 2014, 15: 27-30.
Vierstra et al., "Functional footprinting of regulatory DNA," Nat. Methods, Oct. 2015, 12(10):927-30.
Walton et al., "Unconstrained genome targeting with near-PAMless engineered CRISPR-Cas9 variants," Science, Apr. 17, 2020, 368:290-296, 7 pages.
Wang et al., Regenerative medicine: targeted genome editing in vivo. Cell Research, Jan. 2015, 25: 271-272.
Wiedenheft et al., "RNA-guided genetic silencing systems in bacteria and archaea," Nature, 2012, 482:331-338.
Wolf et al., "tadA, an essential tRNA-specific adenosine deaminase from *Escherichia coli*," EMBO J., Jul. 2002, 21(14):3841-3851.
Wright et al., "Rational design of a split-Cas9 enzyme complex," Proc. Natl. Acad. Sci. USA., Mar. 2015, 112(10):2984-2989.
Wu et al., "Evolution of Inosine-Specific Endonuclease V from Bacterial DNase to Eukaryotic RNase," Molecular Cell, Oct. 2019, 76(1):44-56.
Wu et al., "Genome-wide binding of the CRISPR endonuclease Cas9 in mammalian cells," Nat Biotechnol. Jul. 2014, 32(7):670-6.
Yang et al. "Engineering and optimising deaminase fusions for genome editing" Nature Communications, Nov. 2016, 7(1):1-12.
Yang et al., "Targeted and genome-wide sequencing reveal single nucleotide variations impacting specificity of Cas9 in human stem cells," Nature Communications, Nov. 2014, 5: 5507.
Zentner & Henikoff., "Epigenome editing made easy," Nat. Biotech., Jun. 2015, 33(6):606-607.
Zetsche et al., "Cpf1 Is a Single RNA-Guided Endonuclease of a Class 2 CRISPR-Cas System," Cell, 2015, 163:759-771.
Zhang et al., "Comparison of non-canonical PAMS for CRISPR/Cas9-mediated DNA cleavage in human cells," Sci Rep, Jun. 2014, 4:5405, 5 pages.
Zhang et al., "Processing-Independent CRISPR RNAs Limit Natural Transformation in Neisseria meningitidis," Mol Cell, May 2013, 50(4):488-503.
Zheng et al., "Anchored multiplex PCR for targeted next-generation sequencing," Nat Med, Nov. 10, 2014, 20(12): 1479-1484.
Lee et al., "Directed evolution of CRISPR-Cas9 to increase its specificity," Nat Commun., Aug. 2018, 9(1):3048, 10 pages.
Xu et al., "SpRY greatly expands the genome editing scope in rice with highly flexible PAM recognition," Genome Biol., Jan. 2021, 22(1):6, 15 pages.
Li et al., "Advances in detecting and reducing off-target effects generated by CRISPR-mediated genome editing," Journal of Genetics and Genomics, Nov. 2019, 46(11):513-521.
Office Action in Japanese Appln. No. 2020-511253, dated Dec. 19, 2023, 6 pages (with English translation).
Nishimasu et al., "Supplemental Information: Crystal Structure of *Staphylococcus aureus* Cas9," Cell, 2015, 11 pages.
Office Action in Chinese Appln. No. 201880068905.9, dated Jul. 22, 2023, 11 pages (with English translation).
Office Action in Chinese Appln. No. 201880068905.9, dated Oct. 26, 2023, 9 pages (with English translation).
Notice of Allowance in Australian Appln. No. 2018320865, dated Sep. 1, 2023, 4 pages.
Nishimasu et al., "Crystal Structure of *Staphylococcus aureus* Cas9," Cell, 2015, 162:1113-1126.

\* cited by examiner

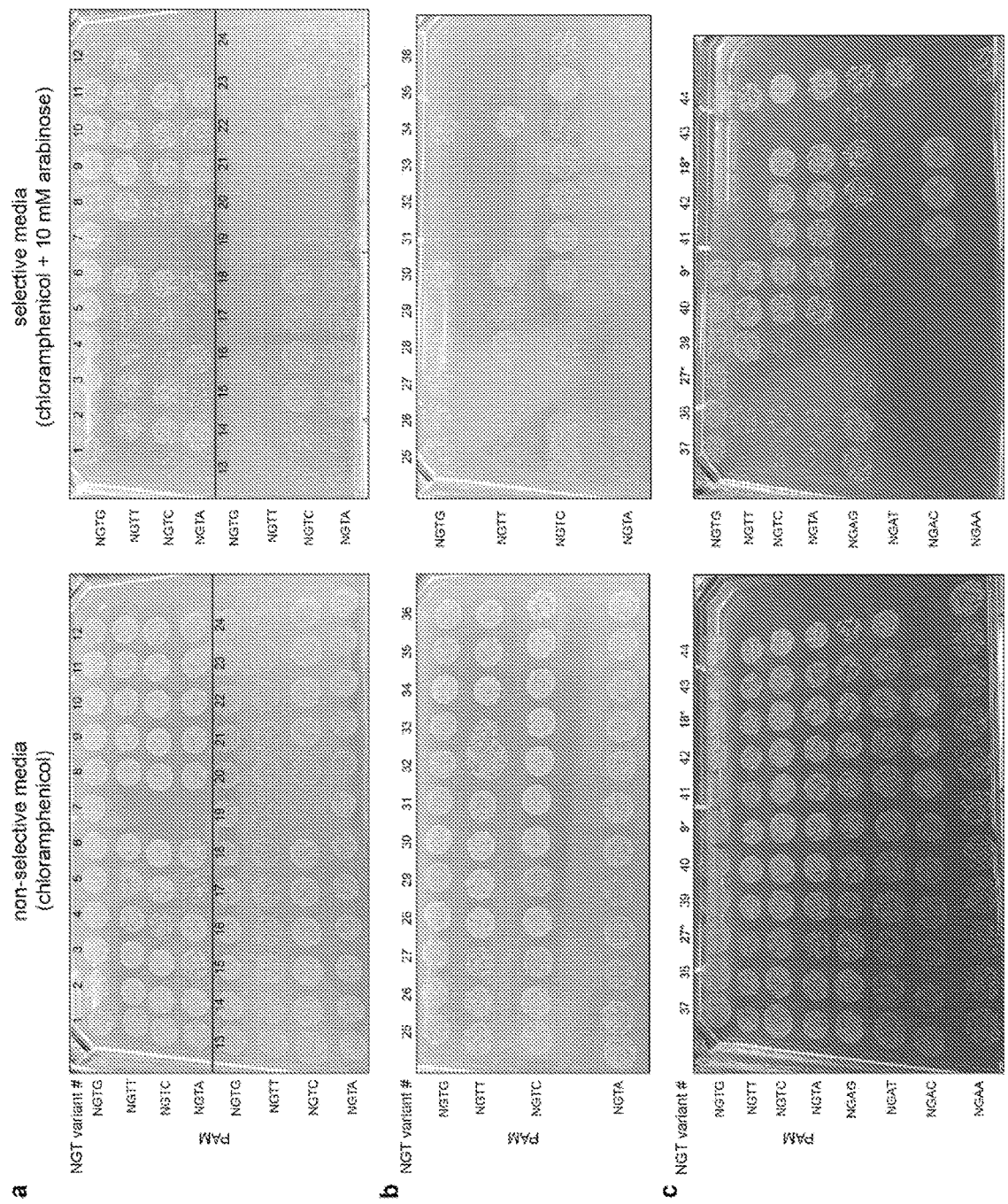
FIGs. 2A-C

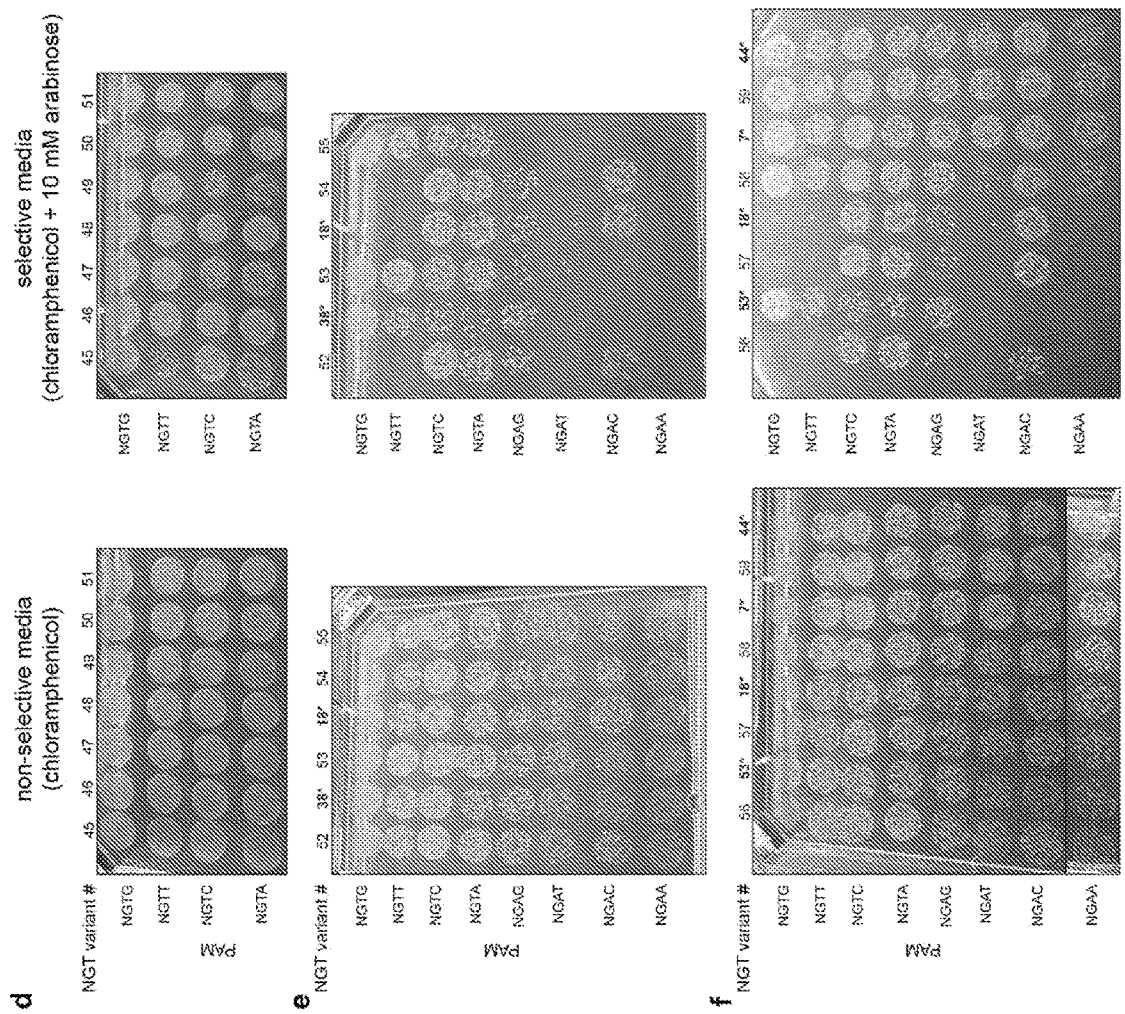
FIGs. 2D-F

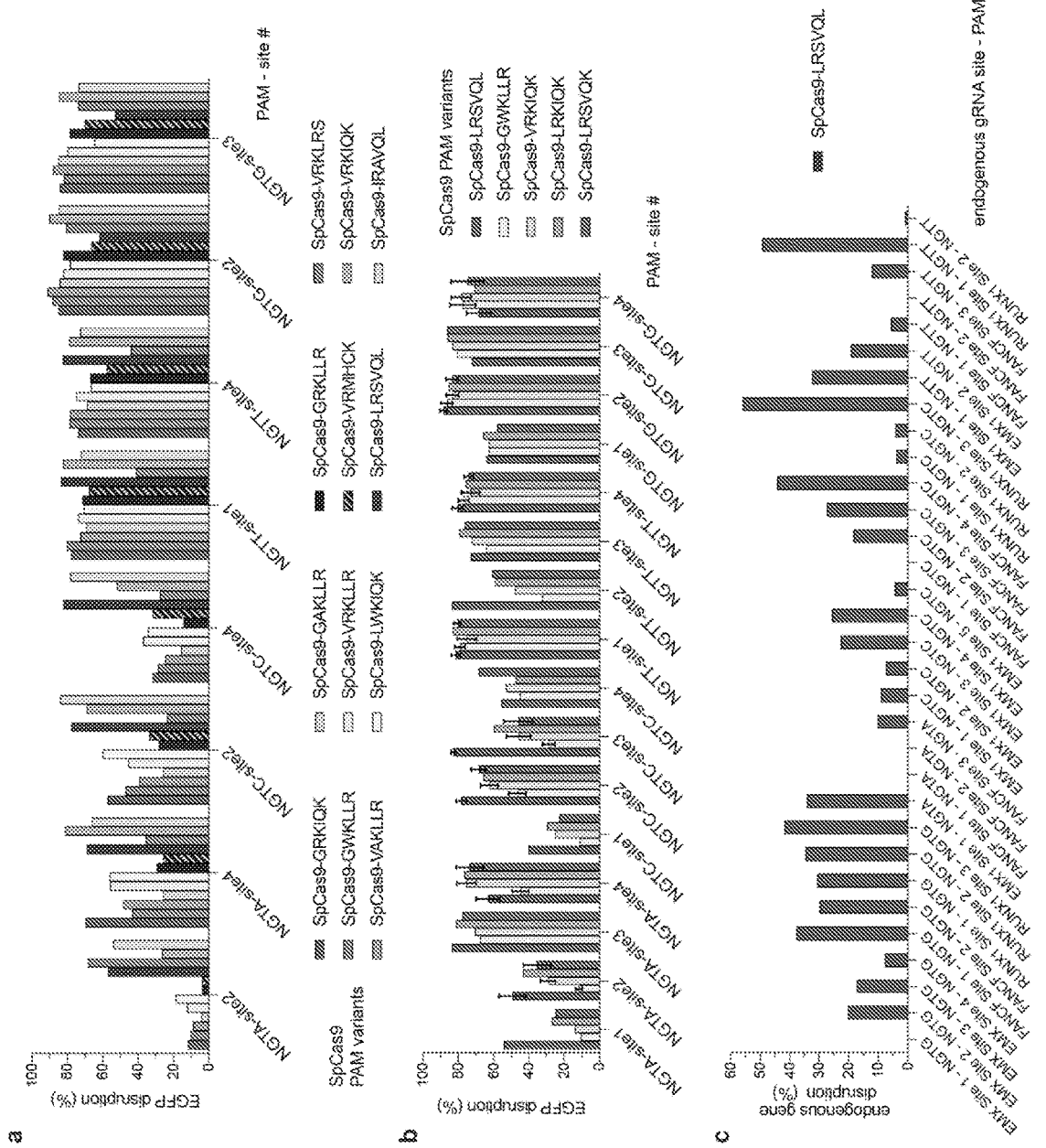
FIGs. 3A-C

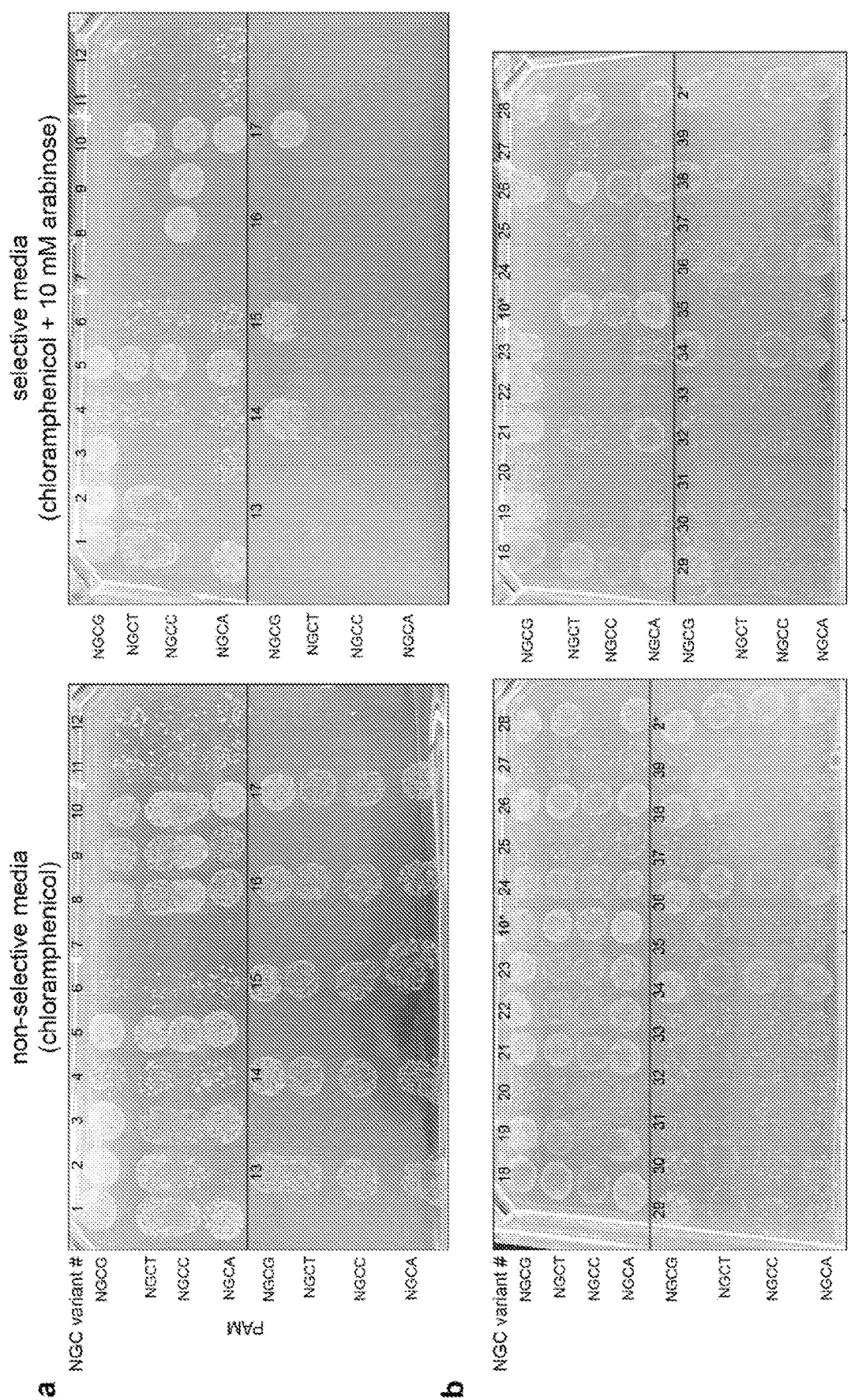
FIGs. 4A-B

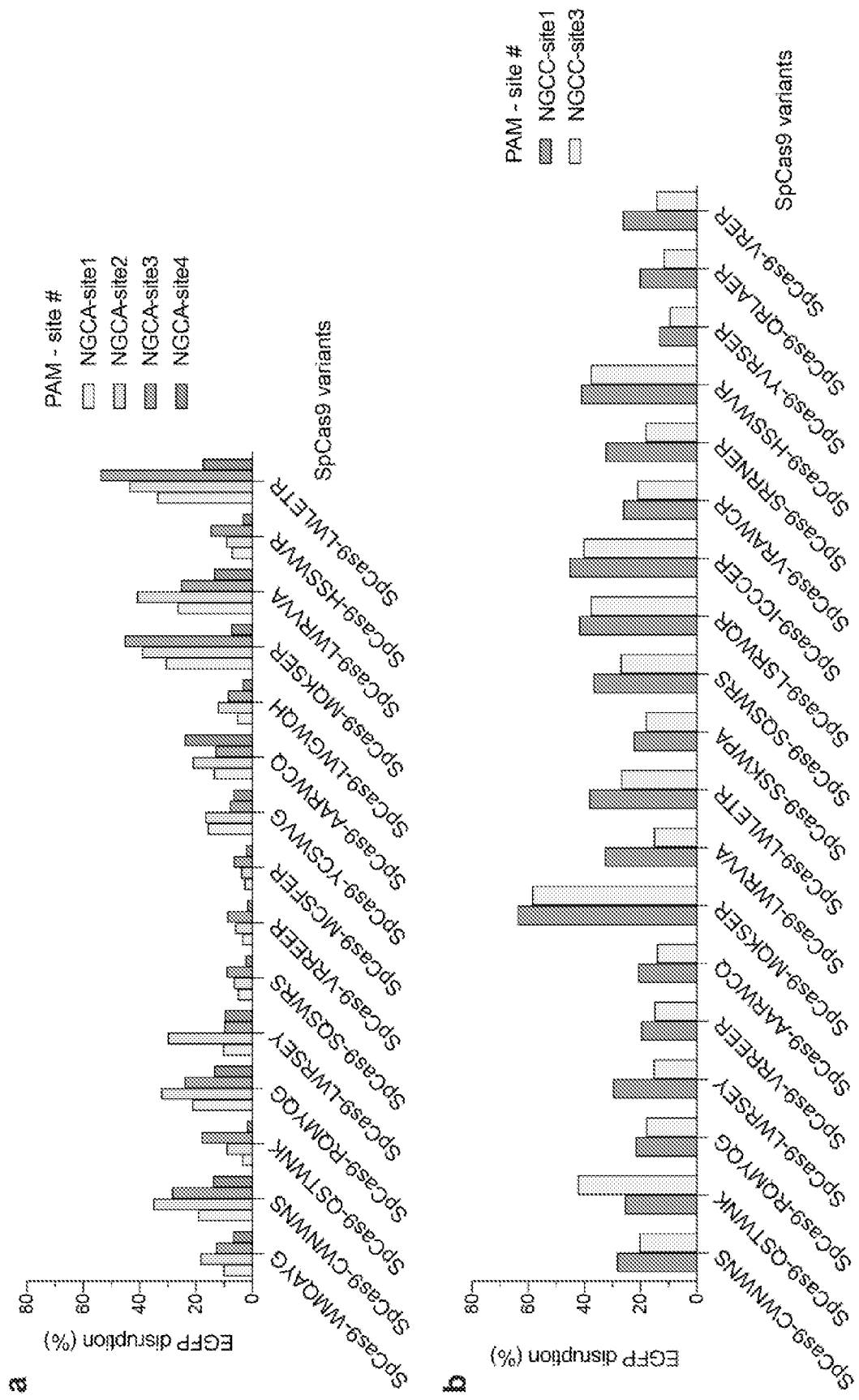
FIGs. 5A-B

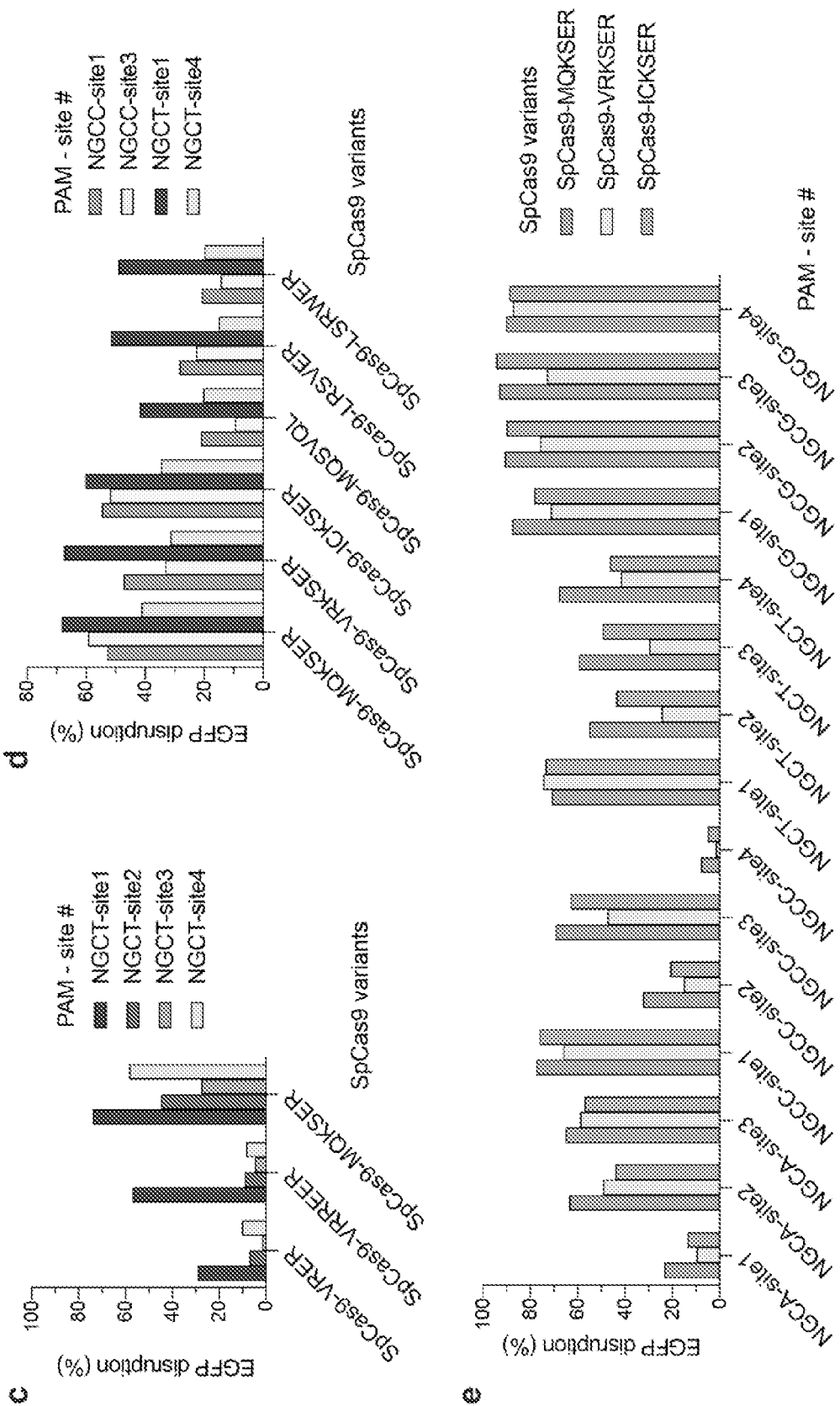
FIGs. 5C-E

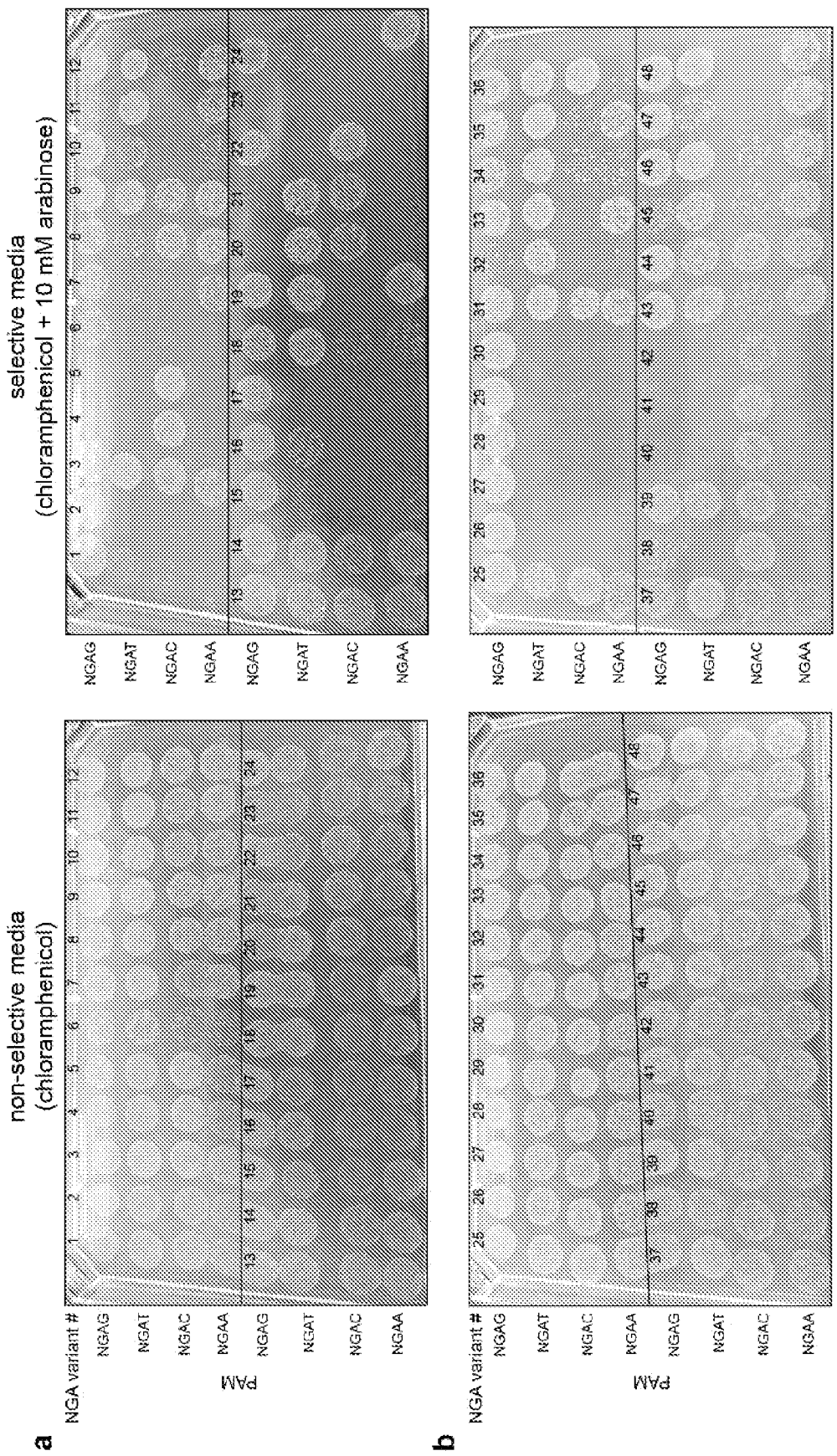
FIGs. 6A-B

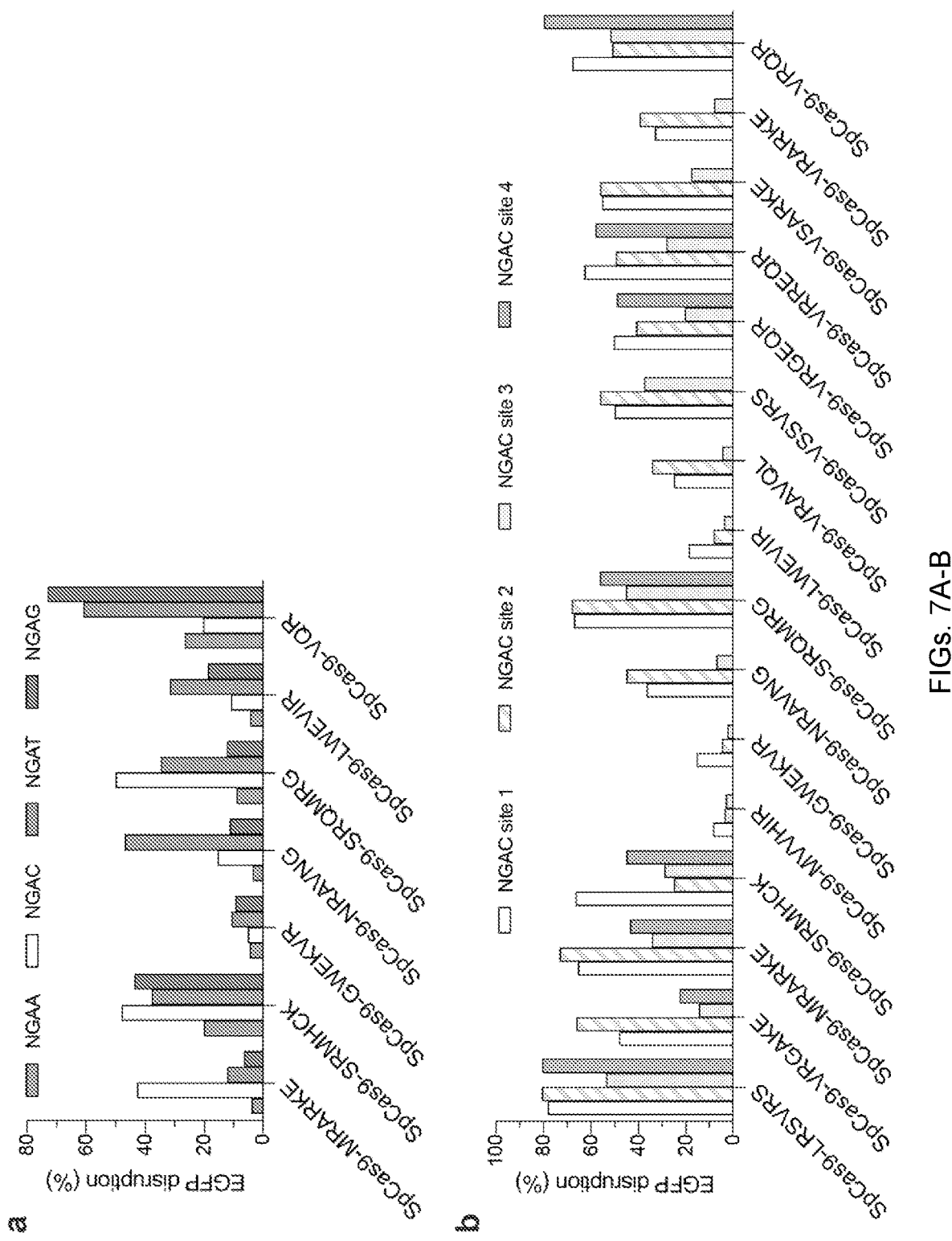
FIGs. 7A-B

SEQUENCE LISTING

```
Sequence total quantity: 11
SEQ ID NO: 1              moltype = AA  length = 1368
FEATURE                   Location/Qualifiers
source                    1..1368
                          mol_type = protein
                          organism = Streptococcus pyogenes
SEQUENCE: 1
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD                1368

SEQ ID NO: 2              moltype = AA  length = 4
FEATURE                   Location/Qualifiers
REGION                    1..4
                          note = Linker
source                    1..4
                          mol_type = protein
                          organism = synthetic construct
SEQUENCE: 2
GGGS                                                                   4

SEQ ID NO: 3              moltype = AA  length = 5
FEATURE                   Location/Qualifiers
REGION                    1..5
                          note = Linker
```

```
source                    1..5
                          mol_type = protein
                          organism = synthetic construct
SEQUENCE: 3
GGGGS                                                                    5

SEQ ID NO: 4              moltype = DNA  length = 20
FEATURE                   Location/Qualifiers
misc_feature              1..20
                          note = forward primer targeted to EMX1 in U2OS human cells
source                    1..20
                          mol_type = other DNA
                          organism = synthetic construct
SEQUENCE: 4
ggagcagctg gtcagagggg                                                   20

SEQ ID NO: 5              moltype = DNA  length = 22
FEATURE                   Location/Qualifiers
misc_feature              1..22
                          note = reverse primer targeted to EMX1 in U2OS human cells
source                    1..22
                          mol_type = other DNA
                          organism = synthetic construct
SEQUENCE: 5
ccatagggaa gggggacact gg                                                22

SEQ ID NO: 6              moltype = DNA  length = 20
FEATURE                   Location/Qualifiers
misc_feature              1..20
                          note = forward primer targeted to FANCF in U2OS human cells
source                    1..20
                          mol_type = other DNA
                          organism = synthetic construct
SEQUENCE: 6
gggccgggaa agagttgctg                                                   20

SEQ ID NO: 7              moltype = DNA  length = 22
FEATURE                   Location/Qualifiers
misc_feature              1..22
                          note = reverse primer targeted to FANCF in U2OS human cells
source                    1..22
                          mol_type = other DNA
                          organism = synthetic construct
SEQUENCE: 7
gccctacatc tgctctccct cc                                                22

SEQ ID NO: 8              moltype = DNA  length = 25
FEATURE                   Location/Qualifiers
misc_feature              1..25
                          note = forward primer targeted to RUNX1 in U2OS human cells
source                    1..25
                          mol_type = other DNA
                          organism = synthetic construct
SEQUENCE: 8
ccagcacaac ttactcgcac ttgac                                             25

SEQ ID NO: 9              moltype = DNA  length = 22
FEATURE                   Location/Qualifiers
misc_feature              1..22
                          note = reverse primer targeted to RUNX1 in U2OS human cells
source                    1..22
                          mol_type = other DNA
                          organism = synthetic construct
SEQUENCE: 9
catcaccaac ccacagccaa gg                                                22

SEQ ID NO: 10             moltype = DNA  length = 21
FEATURE                   Location/Qualifiers
misc_feature              1..21
                          note = forward primer targeted to VEGFA in U2OS human cells
source                    1..21
                          mol_type = other DNA
                          organism = synthetic construct
SEQUENCE: 10
gatgagggct ccagatggca c                                                 21

SEQ ID NO: 11             moltype = DNA  length = 23
FEATURE                   Location/Qualifiers
misc_feature              1..23
```

| | |
|---|---|
| source | note = reverse primer targeted to VEGFA in U2OS human cells<br>1..23<br>mol_type = other DNA<br>organism = synthetic construct |

SEQUENCE: 11
gaggagggag caggaaagtg agg                                              23

ENGINEERED CRISPR-Cas9 NUCLEASES WITH ALTERED PAM SPECIFICITY

CLAIM OF PRIORITY

This application is a continuation application of U.S. patent application Ser. No. 17/674,558, filed Feb. 17, 2022, which is a continuation of U.S. patent application Ser. No. 16/109,657, filed Aug. 22, 2018, now U.S. Pat. No. 11,286, 468, which claims the benefit of U.S. Provisional Patent Application Ser. No. 62/641,687, filed on Mar. 12, 2018, and 62/549,303, filed on Aug. 23, 2017. The entire contents of the foregoing are hereby incorporated by reference.

FEDERALLY SPONSORED RESEARCH OR DEVELOPMENT

This invention was made with Government support under Grant Nos. GM105378, GM107427, GM118158, and GM088040 awarded by the National Institutes of Health. The Government has certain rights in the invention.

SEQUENCE LISTING

This application contains a Sequence Listing that has been submitted electronically as an XML file named "40978-0030003.XML." The XML file, created on Feb. 23, 2023, is 16,086 bytes in size. The material in the XML file is hereby incorporated by reference in its entirety.

TECHNICAL FIELD

The invention relates, at least in part, to engineered Clustered Regularly Interspaced Short Palindromic Repeats (CRISPRs)/CRISPR-associated protein 9 (Cas9) nucleases with altered and improved Protospacer Adjacent Motif (PAM) specificities and their use in genomic engineering, epigenomic engineering, and genome targeting.

BACKGROUND

CRISPR-Cas9 nucleases enable efficient, customizable genome editing in a wide variety of organisms and cell types (Sander & Joung, Nat Biotechnol 32, 347-355 (2014); Hsu et al., Cell 157, 1262-1278 (2014); Doudna & Charpentier, Science 346, 1258096 (2014); Barrangou & May, Expert Opin Biol Ther 15, 311-314 (2015)). Target site recognition by Cas9 is directed by two short RNAs known as the crRNA and tracrRNA (Deltcheva et al., Nature 471, 602-607 (2011); Jinek et al., Science 337, 816-821 (2012)), which can be fused into a chimeric single guide RNA (sgRNA) (Jinek et al., Science 337, 816-821 (2012); Jinek et al., Elife 2, e00471 (2013); Mali et al., Science 339, 823-826 (2013); Cong et al., Science 339, 819-823 (2013)). The 5' end of the sgRNA (derived from the crRNA) can base pair with the target DNA site, thereby permitting straightforward re-programming of site-specific cleavage by the Cas9/sgRNA complex (Jinek et al., Science 337, 816-821 (2012)). However, Cas9 must also recognize a specific protospacer adjacent motif (PAM) that lies proximal to the DNA that base pairs with the sgRNA (Mojica et al., Microbiology 155, 733-740 (2009); Shah et al., RNA Biol 10, 891-899 (2013); Jinek et al., Science 337, 816-821 (2012); Sapranauskas et al, Nucleic Acids Res 39, 9275-9282 (2011); Horvath et al., J Bacteriol 190, 1401-1412 (2008)), a requirement that is needed to initiate sequence-specific recognition (Sternberg et al., Nature 507, 62-67 (2014)) but that can also constrain the targeting range of these nucleases for genome editing. The broadly used Streptococcus pyogenes Cas9 (SpCas9) recognizes a short NGG PAM (Jinek et al., Science 337, 816-821 (2012); Jiang et al., Nat Biotechnol 31, 233-239 (2013)), which occurs once in every 8 bps of random DNA sequence. By contrast, other Cas9 orthologues characterized to date can recognize longer PAMs (Horvath et al., J Bacteriol 190, 1401-1412 (2008); Fonfara et al., Nucleic Acids Res 42, 2577-2590 (2014); Esvelt et al., Nat Methods 10, 1116-1121 (2013); Ran et al., Nature 520, 186-191 (2015); Zhang et al., Mol Cell 50, 488-503 (2013)). For example, Staphylococcus aureus Cas9 (SaCas9), one of several smaller Cas9 orthologues that are better suited for viral delivery (Horvath et al., J Bacteriol 190, 1401-1412 (2008); Ran et al., Nature 520, 186-191 (2015); Zhang et al., Mol Cell 50, 488-503 (2013)), recognizes a longer NNGRRT PAM that is expected to occur once in every 32 bps of random DNA. Broadening the targeting range of Cas9 orthologues is important for various applications including the modification of small genetic elements (e.g., transcription factor binding sites (Canver et al. Nature. 527(7577):192-7 (2015); Vierstra et al., Nat Methods. 12(10):927-30 (2015)) or performing allele-specific alterations by positioning sequence differences within the PAM (Courtney, D. G. et al. Gene Ther. 23(1):108-12 (2015). We previously engineered variants of SpCas9 that could recognize sites with NGA and NGCG PAM sequences (Kleinstiver et al, Nature 2015; WO 2016141224), yet many alternative PAM sequences remain untargetable.

SUMMARY

As described herein, the commonly used Streptococcus pyogenes Cas9 (SpCas9) was engineered to recognize novel PAM sequences using structural information, bacterial selection-based directed evolution, and combinatorial design. These altered PAM specificity variants enable robust editing of reporter sites and endogenous gene sites in human cells that cannot be efficiently targeted by wild-type SpCas9. The present findings provide broadly useful SpCas9 variants, referred to collectively herein as "variants" or "the variants".

In a first aspect, the invention provides isolated Streptococcus pyogenes Cas9 (SpCas9) proteins with mutations at three, four, five, or all six of the following positions: D1135, 51136, G1218, E1219, R1335, and/or T1337, e.g., at two, three, four, five, or all of D1135, 51136, G1218, E1219, R1335, and/or T1337 (D1135X/S1136X/G1218X/E1219X/R1335X/T1337X, where X is any amino acid), e.g., comprising a sequence that is at least 80%, 90%, or 95% identical to the amino acid sequence of SEQ ID NO:1 with the indicated mutations. In some embodiments, the variant SpCas9 proteins comprise a set of mutations shown in Tables A, 1, 2, or 3, e.g., one of the following sets of mutations: LRSVQL, LRKIQK, LRSVQK, LWKIQK, VRKIQK, LWKIQK, IRAVQL, VRKLRS, GRKIQK, SWRVVV, SWKVLK, TAHFKV, MSGVKC, LRSVRS, SKTLRP, MWVHLN, TWSMRG, KRRCKV, VRAVQL, VSSVRS, VRSVRS, SRMHCK, GWKLLR, GWKOQK, VAKLLR, VAKIQK, VAKILR, GRKILR, VRKLLR, IRAVQL, VRKIQK, or VRMHCK variant (e.g., for NGTN PAMs); MQKSER, VRKSER, ICKSER, LRSVER, LWLETR, LSRWER, MQSVQL, VRREER, ICCCER, LSRWQR, LWRVVA, WMQAYG, LWRSEY, SQSWRS, LKAWRS, LWGWQH, MCSFER, LWMREQ, LWRVVA, HSSWVR, MWSEPT, GSNYQS, FMQWVN, YCSWVG, MCAWCG, FMQWVR, or SSKWPA variant (e.g., for NGCN PAMs); LRSVRS, SRQMRG, MRARKE, SRM- HCK, VRREQR, VRGEQR, LRLSAR, AWTEVTR, KWMMCG, VRGAKE, AWNFQV, LWTTLN, SRMHCK, CWCQCV, AEEQQR, GWEKVR, NRAVNG, LRSYLH, VRGNNR, VQDAQR, GWRQSK, AWLCLS, KWARVV, MWAARP, SRMHCK, VKMAKG, QRKTRE, LCRQQR, CWSHQR, SRTHTQ, LWEVIR, VSSVRS, VRSVRS, IRAVRS, SRSVRS, LWKIQK, or VRMHCK variant (e.g., for NGAN PAMs). In some embodiments, the mutations are not VSREER (also known as VRER) or VSREQR (also known as VRQR).

In some embodiments, the variant SpCas9 proteins comprise one or more mutations that decrease nuclease activity selected from the group consisting of mutations at D10, E762, D839, H983, or D986; and at H840 or N863. In some embodiments, the mutations are: (i) D10A or D10N, and (ii) H840A, H840N, or H840Y.

In some embodiments, the variant SpCas9 proteins comprise one or more mutations that increase specificity selected from the group consisting of mutations at N497, K526, R661, R691, N692, M694, Q695, H698, K810, K848, Q926, K1003, and/or R0160. In some embodiments, the mutations are: N692A, Q695A, Q926A, H698A, N497A, K526A, R661A, R691A, M694A, K810A, K848A, K1003A, R0160A, Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E; N692A/M694A/Q695A/H698A, N692A/M694A/Q695A/H698A/Q926A; N692A/M694A/Q695A/Q926A; N692A/M694A/H698A/Q926A; N692A/Q695A/H698A/Q926A; M694A/Q695A/H698A/Q926A; N692A/Q695A/H698A; N692A/M694A/Q695A; N692A/H698A/Q926A; N692A/M694A/Q926A; N692A/M694A/H698A; M694A/Q695A/H698A; M694A/Q695A/Q926A; Q695A/H698A/Q926A; G582A/V583A/E584A/D585A/N588A/Q926A; G582A/V583A/E584A/D585A/N588A; T657A/G658A/W659A/R661A/Q926A; T657A/G658A/W659A/R661A; F491A/M495A/T496A/N497A/Q926A; F491A/M495A/T496A/N497A; K918A/V922A/R925A/Q926A; or 918A/V922A/R925A; K855A; K810A/K1003A/R1060A; or K848A/K1003A/R1060A. In some embodiments, the proteins do not include mutations at K526 or R691.

Also provided herein are fusion proteins comprising the isolated variant SpCas9 proteins described herein fused to a heterologous functional domain, with an optional intervening linker, wherein the linker does not interfere with activity of the fusion protein. In some embodiments, the heterologous functional domain is a transcriptional activation domain. In some embodiments, the transcriptional activation domain is from VP64 or NF-κB p65. In some embodiments, the heterologous functional domain is a transcriptional silencer or transcriptional repression domain. In some embodiments, the transcriptional repression domain is a Krueppel-associated box (KRAB) domain, ERF repressor domain (ERD), or mSin3A interaction domain (SID). In some embodiments, the transcriptional silencer is Heterochromatin Protein 1 (HP1), e.g., HP1α or HP1β. In some embodiments, the heterologous functional domain is an enzyme that modifies the methylation state of DNA. In some embodiments, the enzyme that modifies the methylation state of DNA is a DNA methyltransferase (DNMT) or a TET protein. In some embodiments, the TET protein is TET1. In some embodiments, the heterologous functional domain is an enzyme that modifies a histone subunit. In some embodiments, the enzyme that modifies a histone subunit is a histone acetyltransferase (HAT), histone deacetylase (HDAC), histone methyltransferase (HMT), or histone demethylase.

In some embodiments, the heterologous functional domain is a base editor, e.g., a cytidine deaminase domain, e.g., from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, or APOBEC4; activation-induced cytidine deaminase (AID), e.g., activation induced cytidine deaminase (AICDA); cytosine deaminase 1 (CDA1) or CDA2; or cytosine deaminase acting on tRNA (CDAT). In some embodiments, the heterologous functional domain is a deaminase that modifies adenosine DNA bases, e.g., the deaminase is an adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA). In some embodiments, the heterologous functional domain is a biological tether. In some embodiments, the biological tether is MS2, Csy4 or lambda N protein. In some embodiments, the heterologous functional domain is FokI.

In some embodiments, the heterologous functional domain is an enzyme, domain, or peptide that inhibits or enhances endogenous DNA repair or base excision repair (BER) pathways, e.g., uracil DNA glycosylase inhibitor (UGI) that inhibits uracil DNA glycosylase (UDG, also known as uracil N-glycosylase, or UNG) mediated excision of uracil to initiate BER; or DNA end-binding proteins such as Gam from the bacteriophage Mu.

Also provided herein are isolated nucleic acids encoding the variant SpCas9 proteins described herein, as well as vectors comprising the isolated nucleic acids, optionally operably linked to one or more regulatory domains for expressing the variant SpCas9 proteins described herein. Also provided herein are host cells, e.g., mammalian host cells, comprising the nucleic acids described herein, and optionally expressing the variant SpCas9 proteins described herein. Also provided herein are ribonucleoprotein (RNP) complexes that include a variant spCas9 protein as described herein and a guide RNA that targets a sequence having a PAM sequence targeted by the variant protein.

Also provided herein are methods of altering the genome of a cell, by expressing in the cell an isolated variant SpCas9 protein described herein, and a guide RNA having a region complementary to a selected portion of the genome of the cell.

Also provided herein are methods for altering, e.g., selectively altering, the genome of a cell by expressing in the cell the variant proteins, and a guide RNA having a region complementary to a selected portion of the genome of the cell.

Also provided are methods for altering, e.g., selectively altering, the genome of a cell by contacting the cell with a protein variant described herein, and a guide RNA having a region complementary to a selected portion of the genome of the cell.

In some embodiments, the isolated protein or fusion protein comprises one or more of a nuclear localization sequence, cell penetrating peptide sequence, and/or affinity tag.

In some embodiments of the methods described herein, the cell is a stem cell, e.g., an embryonic stem cell, mesenchymal stem cell, or induced pluripotent stem cell; is in a living animal; or is in an embryo, e.g., a mammalian, insect, or fish (e.g., zebrafish) embryo or embryonic cell.

Further, provided herein are methods, e.g., in vitro methods, for altering a double stranded DNA (dsDNA) molecule. The methods include contacting the dsDNA molecule with one or more of the variant proteins described herein, and a guide RNA having a region complementary to a selected portion of the dsDNA molecule.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and FIGs, and from the claims.

DESCRIPTION OF DRAWINGS

FIGS. 2A-F. SpCas9 PAM variants obtained from bacterial selection that recognize sites with NGTN PAMs. (A-F) Plasmids encoding SpCas9 variants from initial screens against positive selection plasmids carrying NGTG, NGTT, NGTC, or NGTA PAM sequences were re-screened in the bacterial screen assay to assess activity on target sites with NGTN PAM sequences. For panels C, E, and F, variants were also screened against target sites with NGAG, NGAT, NGAC, and NGAA PAMs. Approximate activities of the variants on sites with the indicated PAMs were calculated by comparing the number of colonies on non-selective media (chloramphenicol only) to those on selective media (chloramphenicol+10 mM arabinose), and calculating the % survival (Table 1). Variants whose numbers have an asterisk indicate plasmids that were tested in prior assays (and shown in above panels of this figure), and the amino acid sequences of these variants can be found in Table 1.

FIGS. 3A-C. Activities of SpCas9 NGTN PAM variants in human cells. (A,B) Human cell EGFP-disruption assays to assess the activities of various SpCas9 variants (that were obtained through selections or rationally designed) against sites in EGFP that harbor NGTA, NGTC, NGTT, and NGTG PAMs. Error bars represent s.e.m. for n=2–7. (C) Endogenous gene disruption activity of one of the top performing SpCas9-NGTN PAM variants, the SpCas9-LRSVQL variant, against sites harboring NGTG, NGTA, NGTC, or NGTT PAMs. Gene disruption quantified by T7E1 assay.

FIGS. 4A-B. SpCas9 PAM variants obtained from bacterial selection that recognize sites with NGCN PAMs. (A-B) Plasmids encoding SpCas9 variants from initial screens against positive selection plasmids carrying NGCG, NGCT, NGCC, or NGCA PAM sequences were re-screened in the bacterial screen assay to assess activity on target sites with NGCN PAM sequences. Approximate activities of the variants on sites with the indicated PAMs were calculated by comparing the number of colonies on non-selective media (chloramphenicol only) to those on selective media (chloramphenicol+10 mM arabinose), and calculating the % survival (Table 2). Variants whose numbers have an asterisk indicate plasmids that were tested in prior assays (and shown in above panels of this figure), and the amino acid sequences of these variants can be found in Table 2.

FIGS. 5A-E. Activities of SpCas9 NGCN PAM variants in human cells. (A-E) Human cell EGFP-disruption assays to assess the activities of various SpCas9 variants (that were obtained through selections or rationally designed) against sites in EGFP that harbor NGCA, NGCC, NGCT, and NGCG PAMs. Activities on sites bearing (A) NGCA PAM sites, (B) NGCC PAM sites, (C) NGCT PAM sites, (D) NGCC and NGCT PAM sites, and (E) various NGCN PAM sites.

FIGS. 6A-B. SpCas9 PAM variants obtained from bacterial selection that recognize sites with NGAN PAMs. (A-B) Plasmids encoding SpCas9 variants from initial screens against positive selection plasmids carrying NGAG, NGAT, NGAC, or NGAA PAM sequences were re-screened in the bacterial screen assay to assess activity on target sites with NGAN PAM sequences. Approximate activities of the variants on sites with the indicated PAMs were calculated by comparing the number of colonies on non-selective media (chloramphenicol only) to those on selective media (chloramphenicol+10 mM arabinose), and calculating the % survival (Table 3). The amino acid sequences of these variants can be found in Table 3.

FIGS. 7A-B. Activities of SpCas9 NGAN PAM variants in human cells. (A-B) Human cell EGFP-disruption assays to assess the activities of various SpCas9 variants (that were obtained through selections or rationally designed) on sites in EGFP that harbor (A) NGAA, NGAC, NGAT, and NGAG PAMs, or (B) various NGAC PAMs.

Table 1: Selection results and activity in bacteria of variants on sites harboring NGTN PAMs Table 2: Selection results and activity in bacteria of variants on sites harboring NGCN PAMs Table 3: Selection results and activity in bacteria of variants on sites harboring NGAN PAMs

DETAILED DESCRIPTION

Recognition of a protospacer adjacent motif (PAM) by *Streptococcus pyogenes* Cas9 (SpCas9) is the critical first step of target DNA recognition, enabling SpCas9 to bind and hydrolyze DNA. Although CRISPR-Cas9 nucleases are widely used for genome editing[1-4], the range of sequences that Cas9 can cleave is constrained by the need for a specific PAM in the target site[5, 6]. For example, SpCas9, the most robust and widely used Cas9 to date, primarily recognizes NGG PAMs. As a result, it can often be difficult to target double-stranded breaks (DSBs) with the precision that is necessary for various genome editing applications. In addition, imperfect PAM recognition by Cas9 can lead to the creation of unwanted off-target mutations[7, 8]. Cas9 derivatives with purposefully altered and/or improved PAM specificities would address these limitations.

Crystal structures reveal that wild-type SpCas9 utilizes two arginine amino acid side chains (R1333 and R1335) to make base specific contacts to the guanines of the canonical NGG PAM sequence. However, to alter PAM recognition and improve the targeting range of SpCas9, we and others have shown that simply mutating either one or both of these arginines does not confer a switch in PAM preference (Anders et al, Nature 2014; Kleinstiver et al, Nature 2015; WO 2016141224). We previously undertook a selection approach to evolve variants of SpCas9 that could target NGA and NGCG PAM sequences (Kleinstiver et al, Nature 2015; WO 2016141224); however, many alternative PAM sequences remain untargetable.

Figure 1A:
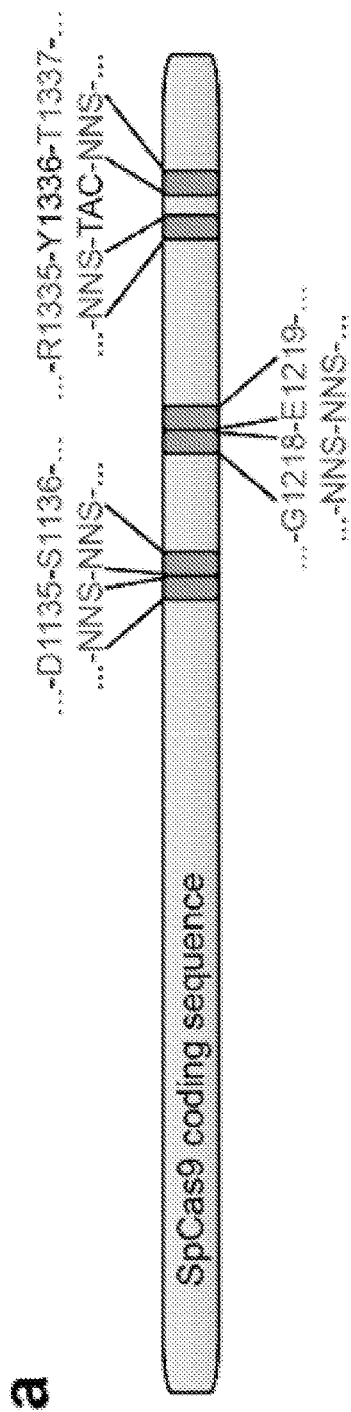
FIGS. 1A-B. Generation and screening of SpCas9 PAM variant libraries. (a) To generate a library of SpCas9 variants with diverse amino acid combinations at six positions important for PAM recognition, degenerate oligo libraries were cloned into three regions of the SpCas9 coding sequence to randomize the six codons highlighted in red. (b) Schematic of the bacterial selection assay, where SpCas9 variants and an sgRNA are expressed from one plasmid, and a second plasmid encodes an inducible toxic gene and a customizable target site. Both plasmids are co-transformed into bacteria, and only cells that harbor an SpCas9 PAM variant that can recognize the PAM encoded in the target site of the toxic plasmid can survive on media that induces expression of the toxic gene (selective media contains 10 mM arabinose).
Figure 1B:
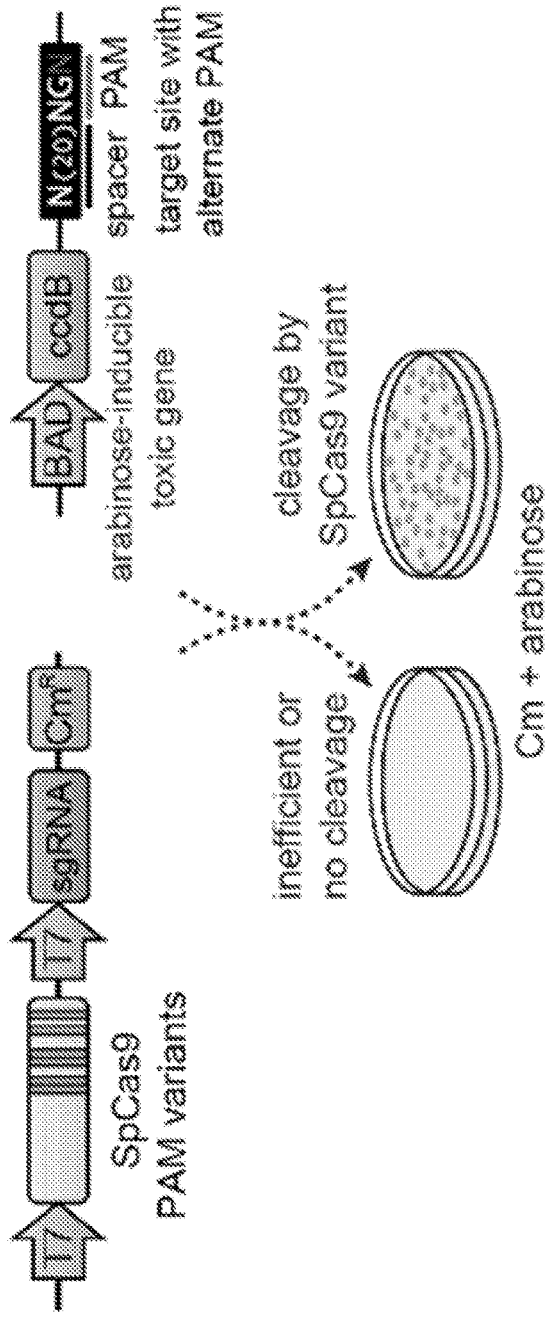

To further expand the utility of SpCas9 by enabling targeting of currently inaccessible PAM sequences, we conceived of an alternative strategy to select for SpCas9 variants capable of recognizing novel PAM sequences. Having established previously that certain positions within the SpCas9 coding sequence are important for PAM recognition (Kleinstiver et al., Nature 2015; WO 2016141224), we conducted a focused saturation mutagenesis approach where we randomized six amino acids within three separate regions of the PAM interacting domain to generate a library of SpCas9 variants with diverse codon usage at these positions: D1135/51136, G1218/E1219, and R1335/T1337. To do so, we sequentially cloned randomized oligonucleotide cassettes encoding NNS nucleotide triplets (where N is any nucleotide and S is G or C) at the codons of SpCas9 that contain encode these six amino acids (FIG. 1A). The resulting library of SpCas9 variants was then subjected to selection using our bacterial positive selection assay as previously described (Kleinstiver et al., Nature 2015) to identify variants that can cleave target sites harboring various NGNN PAM sequences (FIG. 1B). Briefly, bacteria can only survive selective conditions (plating on 10 mM arabinose, which induces transcription of the ccdB toxic gene) if an expressed SpCas9 variant can recognize the target site (PAM and spacer sequence) encoded in the positive selection plasmid. Strong PAM recognition will lead to hydrolysis of the selection plasmid, preventing induction of ccdB expression and thereby allowing bacterial growth. Thus, while screening SpCas9 libraries, colonies that grow on media containing 10 mM arabinose are expected to encode an SpCas9 PAM variant that can target a site bearing an alternate PAM of interest (FIG. 1B).

Engineered Cas9 Variants with Altered PAM Specificities

The SpCas9 variants engineered in this study greatly increase the range of target sites accessible by wild-type SpCas9, further enhancing the opportunities to use the CRISPR-Cas9 platform to practice efficient HDR, to target NHEJ-mediated indels to small genetic elements, and to exploit the requirement for a PAM to distinguish between two different alleles in the same cell. The selection and rational design of variants that can now target formerly inaccessible NGTN and NGCH (where H is A, C, or T) PAM containing sites, and variants that can improve activity against NGAC, improve the prospects for accurate and high-resolution genome-editing. The altered PAM specificity SpCas9 variants can efficiently disrupt endogenous gene sites that are not currently targetable by SpCas9 in both bacterial and human cells, suggesting that they will work in a variety of different cell types and organisms.

All of the SpCas9 variants described herein can be rapidly incorporated into existing and widely used vectors, e.g., by simple site-directed mutagenesis, and because they require only a small number of mutations contained within the PAM-interacting domain, the variants should also work with other previously described improvements to the SpCas9 platform (e.g., truncated sgRNAs (Tsai et al., *Nat Biotechnol* 33, 187-197 (2015); Fu et al., *Nat Biotechnol* 32, 279-284 (2014)), nickase mutations (Mali et al., *Nat Biotechnol* 31, 833-838 (2013); Ran et al., *Cell* 154, 1380-1389 (2013)), dimeric FokI-dCas9 fusions (Guilinger et al., *Nat Biotechnol* 32, 577-582 (2014); Tsai et al., *Nat Biotechnol* 32, 569-576 (2014)); and high-fidelity variants (Kleinstiver et al. *Nature* 2016).

SpCas9 Variants with Altered PAM Specificity

Thus, provided herein are SpCas9 variants. The SpCas9 wild type sequence is as follows:

```
                                    (SEQ ID NO: 1)
         10         20         30         40
MDKKYSIGLD IGTNSVGWAV ITDEYKVPSK KFKVLGNTDR 50         60         70         80
HSIKKNLIGA LLFDSGETAE ATRLKRTARR RYTRRKNRIC 90        100        110        120
YLQEIFSNEM AKVDDSFFHR LEESFLVEED KKHERHPIFG 130        140        150        160
NIVDEVAYHE KYPTIYHLRK KLVDSTDKAD LRLIYLALAH 170        180        190        200
MIKFRGHFLI EGDLNPDNSD VDKLFIQLVQ TYNQLFEENP 210        220        230        240
INASGVDAKA ILSARLSKSR RLENLIAQLP GEKKNGLFGN 250        260        270        280
LIALSLGLTP NFKSNFDLAE DAKLQLSKDT YDDDLDNLLA 290        300        310        320
QIGDQYADLF LAAKNLSDAI LLSDILRVNT EITKAPLSAS 330        340        350        360
MIKRYDEHHQ DLTLLKALVR QQLPEKYKEI FFDQSKNGYA 370        380        390        400
GYIDGGASQE EFYKFIKPIL EKMDGTEELL VKLNREDLLR 410        420        430        440
KQRTFDNGSI PHQIHLGELH AILRRQEDFY PFLKDNREKI
```

```
       450        460        470        480
EKILTFRIPY YVGPLARGNS RFAWMTRKSE ETITPWNFEE 490        500        510        520
VVDKGASAQS FIERMTNFDK NLPNEKVLPK HSLLYEYFTV 530        540        550        560
YNELTKVKYV TEGMRKPAFL SGEQKKAIVD LLFKTNRKVT 570        580        590        600
VKQLKEDYFK KIECFDSVEI SGVEDRFNAS LGTYHDLLKI 610        620        630        640
IKDKDFLDNE ENEDILEDIV LTLTLFEDRE MIEERLKTYA 650        660        670        680
HLFDDKVMKQ LKRRRYTGWG RLSRKLINGI RDKQSGKTIL 690        700        710        720
DFLKSDGFAN RNFMQLIHDD SLTFKEDIQK AQVSGQGDSL 730        740        750        760
HEHIANLAGS PAIKKGILQT VKVVDELVKV MGRHKPENIV 770        780        790        800
IEMARENQTT QKGQKNSRER MKRIEEGIKE LGSQILKEHP 810        820        830        840
VENTQLQNEK LYLYYLQNGR DMYVDQELDI NRLSDYDVDH 850        860        870        880
IVPQSFLKDD SIDNKVLTRS DKNRGKSDNV PSEEVVKKMK 890        900        910        920
NYWRQLLNAK LITQRKFDNL TKAERGGLSE LDKAGFIKRQ 930        940        950        960
LVETRQITKH VAQILDSRMN TKYDENDKLI REVKVITLKS 970        980        990       1000
KLVSDFRKDF QFYKVREINN YHHAHDAYLN AVVGTALIKK 1010       1020       1030       1040
YPKLESEFVY GDYKVYDVRK MIAKSEQEIG KATAKYFFYS 1050       1060       1070       1080
NIMNFFKTEI TLANGEIRKR PLIETNGETG EIVWDKGRDF 1090       1100       1110       1120
ATVRKVLSMP QVNIVKKTEV QTGGFSKESI LPKRNSDKLI 1130       1140       1150       1160
ARKKDWDPKK YGGFDSPTVA YSVLVVAKVE KGKSKKLKSV 1170       1180       1190       1200
KELLGITIME RSSFEKNPID FLEAKGYKEV KKDLIIKLPK 1210       1220       1230       1240
YSLFELENGR KRMLASAGEL QKGNELALPS KYVNFLYLAS 1250       1260       1270       1280
HYEKLKGSPE DNEQKQLFVE QHKHYLDEII EQISEFSKRV 1290       1300       1310       1320
ILADANLDKV LSAYNKHRDK PIREQAENII HLFTLTNLGA 1330       1340       1350       1360
PAAFKYFDTT IDRKRYTSTK EVLDATLIHQ SITGLYETRI

DLSQLGGD
```

The SpCas9 variants described herein can include mutations at one, two, three, four, five, or all six of the following positions: D1135, 51136, G1218, E1219, R1335, and/or T1337, e.g., D1135X/S1136X/G1218X/E1219X/R1335X/T1337X, where X is any amino acid (or at positions analogous thereto). In some embodiments, the SpCas9 variants are at least 80%, e.g., at least 85%, 90%, or 95% identical to the amino acid sequence of SEQ ID NO:1, e.g., have differences at up to 5%, 10%, 15%, or 20% of the residues of SEQ ID NO:1 replaced, e.g., with conservative mutations. In preferred embodiments, the variant retains desired activity of the parent, e.g., the nuclease activity (except where the parent is a nickase or a dead Cas9), and/or the ability to interact with a guide RNA and target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) *J Mol Biol* 147:195-7); "BestFit" (Smith and Waterman, *Advances in Applied Mathematics,* 482-489 (1981)) as incorporated into GeneMatcher Plus™, Schwarz and Dayhof (1979) *Atlas of Protein Sequence and Structure, Dayhof, M. O., Ed,* pp 353-358; BLAST program (Basic Local Alignment Search Tool; (Altschul, S. F., W. Gish, et al. (1990) *J Mol Biol* 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned using the BLAST algorithm and the default parameters.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In some embodiments, the SpCas9 variants include a set of mutations shown in Tables 1, 2, or 3, e.g., one of the following sets of mutations at D1135X/S1136X/G1218X/E1219X/R1335X/T1337X: SpCas9-LWKIQK, LWKIQK, IRAVQL, SWRVVV, SWKVLK, TAHFKV, MSGVKC, LRSVRS, SKTLRP, MWVHLN, TWSMRG, KRRCKV, VRAVQL, VSSVRS, VRSVRS, SRMHCK, GRKIQK, GWKLLR, GWKOQK, VAKLLR, VAKIQK, VAKILR, GRKILR, VRKLLR, LRSVQL, IRAVQL, VRKIQK, VRM-HCK, LRKIQK, LRSVQK, or VRKIQK variant (e.g., for NGTN PAMs); WMQAYG, MQKSER, LWRSEY, SQSWRS, LKAWRS, LWGWQH, MCSFER, LWMREQ, LWRVVA, HSSWVR, MWSEPT, GSNYQS, FMQWVN, YCSWVG, MCAWCG, LWLETR, FMQWVR, SSKWPA, LSRWQR, ICCCER, VRKSER, or ICKSER (e.g., for NGCN PAMs); or LRLSAR, AWTEVTR, KWMMCG, VRGAKE, MRARKE, AWNFQV, LWTTLN, SRMHCK, CWCQCV, AEEQQR, GWEKVR, NRAVNG, SRQMRG, LRSYLH, VRGNNR, VQDAQR, GWRQSK, AWLCLS, KWARVV, MWAARP, SRMHCK, VKMAKG, QRKTRE, LCRQQR, CWSHQR, SRTHTQ, LWEVIR, VSSVRS, VRSVRS, LRSVRS, IRAVRS, SRSVRS, LWKIQK, VRM-HCK, or SRMHCK (e.g., for NGAN PAMs). In some embodiments, the spCas9 variants include D1135L/S1136R/G1218S/E1219V/R1335X/T1337X, e.g., LRSVQL or LRSVRS. In some embodiments, the residue at D1135 is an L, G, I, V, M, or S. In some embodiments, the residue at S1136 is an R, Q, W, S, or C. In some embodiments, the residue at G1218 is an S, K, S, R, L, C, G, A, or Q. In some embodiments, the residue at E1219 is V, I, S, E, W, C, A, or R. In some embodiments, the residue at R1335 is an R, Q, E, V, T, or K. In some embodiments, the residue at T1337 is an S, K, L, R, A, E, T, or G. In some embodiments, the variants include one of the sets of mutations in Table A.

TABLE A

| NGTN PAM | NGCN PAM | NGAN PAM |
| --- | --- | --- |
| LRSVRS | MQKSER | VRGAKE |
| GRKIQK | LWRVVA | MRARKE |
| LRSVQL | LWLETR | SRQMRG |
| IRAVQL | LSRWQR | LRSVRS |
| LRKIQK | ICCCER | |
| LRSVQK | VRKSER | |
| VRKIQK | ICKSER | |

In some embodiments, the SpCas9 variants also include mutations at one of the following amino acid positions, which reduce or destroy the nuclease activity of the Cas9: D10, E762, D839, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)), or other residues, e.g., glutamine, asparagine, tyrosine, serine, or aspartate, e.g., E762Q, H983N, H983Y, D986N, N863D, N863S, or N863H (see WO 2014/152432). In some embodiments, the variant includes mutations at D10A or H840A (which creates a single-strand nickase), or mutations at D10A and H840A (which abrogates nuclease activity; this mutant is known as dead Cas9 or dCas9).

In some embodiments, the SpCas9 variants also include mutations at one or more amino acid positions that increase the specificity of the protein (i.e., reduce off-target effects). In some embodiments, the SpCas9 variants include one, two, three, four, five, six, seven, eight, nine, ten, eleven, twelve, or all thirteen mutations at the following residues: N497, K526, R661, R691, N692, M694, Q695, H698, K810, K848, Q926, K1003, and/or R0160. In some embodiments, the mutations are: N692A, Q695A, Q926A, H698A, N497A, K526A, R661A, R691A, M694A, K810A, K848A, K1003A, R0160A, Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E; N692A/M694A/Q695A/H698A, N692A/M694A/Q695A/H698A/Q926A; N692A/M694A/Q695A/Q926A; N692A/M694A/H698A/Q926A; N692A/Q695A/H698A/Q926A; M694A/Q695A/H698A/Q926A; N692A/Q695A/H698A; N692A/M694A/Q695A; N692A/H698A/Q926A; N692A/M694A/Q926A; N692A/M694A/H698A; M694A/Q695A/H698A; M694A/Q695A/Q926A; Q695A/H698A/Q926A; G582A/V583A/E584A/D585A/N588A/Q926A; G582A/V583A/E584A/D585A/N588A; T657A/G658A/W659A/R661A/Q926A; T657A/G658A/W659A/R661A; F491A/M495A/T496A/N497A/Q926A; F491A/M495A/T496A/N497A; K918A/V922A/R925A/Q926A; or 918A/V922A/R925A; K855A; K810A/K1003A/R1060A; or K848A/K1003A/R1060A. See, e.g., U.S. Pat. No. 9,512,446B1; Kleinstiver et al., Nature. 2016 Jan. 28; 529(7587): 490-5; Slaymaker et al., Science. 2016 Jan. 1; 351(6268): 84-8; Chen et al., Nature. 2017 Oct. 19; 550(7676):407-410; Tsai and Joung, Nature Reviews Genetics 17:300-312 (2016); Vakulskas et al., Nature Medicine 24:1216-1224 (2018); Casini et al., Nat Biotechnol. 2018 March; 36(3): 265-271. In some embodiments, the variants do not include mutations at K526 or R691.

In some embodiments, the SpCas9 variants include mutations at one, two, three, four, five, six or all seven of the following positions: L169A, Y450, N497, R661, Q695, Q926, and/or D1135E, e.g., in some embodiments, the variant SpCas9 proteins comprise mutations at one, two, three, or all four of the following: N497, R661, Q695, and Q926, e.g., one, two, three, or all four of the following mutations: N497A, R661A, Q695A, and Q926A. In some embodiments, the variant SpCas9 proteins comprise mutations at Q695 and/or Q926, and optionally one, two, three, four or all five of L169, Y450, N497, R661 and D1135E, e.g., including but not limited to Y450A/Q695A, L169A/Q695A, Q695A/Q926A, Q695A/D1135E, Q926A/D1135E, Y450A/D1135E, L169A/Y450A/Q695A, L169A/Q695A/Q926A, Y450A/Q695A/Q926A, R661A/Q695A/Q926A, N497A/Q695A/Q926A, Y450A/Q695A/D1135E, Y450A/Q926A/D1135E, Q695A/Q926A/D1135E, L169A/Y450A/Q695A/Q926A, L169A/R661A/Q695A/Q926A, Y450A/R661A/Q695A/Q926A, N497A/Q695A/Q926A/D1135E, R661A/Q695A/Q926A/D1135E, and Y450A/Q695A/Q926A/D1135E. See, e.g., Kleinstiver et al., Nature 529: 490-495 (2016); WO 2017/040348; U.S. Pat. No. 9,512, 446).

In some embodiments, the SpCas9 variants also include mutations at one, two, three, four, five, six, seven, or more of the following positions: F491, M495, T496, N497, G582, V583, E584, D585, N588, T657, G658, W659, R661, N692, M694, Q695, H698, K918, V922, and/or R925, and optionally at Q926, preferably comprising a sequence that is at least 80% identical to the amino acid sequence of SEQ ID NO:1 with mutations at one, two, three, four, five, six, seven, or more of the following positions: F491, M495, T496, N497, G582, V583, E584, D585, N588, T657, G658, W659, R661, N692, M694, Q695, H698, K918, V922, and/or R925, and optionally at Q926, and optionally one or more of a nuclear localization sequence, cell penetrating peptide sequence, and/or affinity tag.

In some embodiments, the proteins comprise mutations at one, two, three, or all four of the following: N692, M694, Q695, and H698; G582, V583, E584, D585, and N588; T657, G658, W659, and R661; F491, M495, T496, and N497; or K918, V922, R925, and Q926.

In some embodiments, the proteins comprise one, two, three, four, or all of the following mutations: N692A, M694A, Q695A, and H698A; G582A, V583A, E584A, D585A, and N588A; T657A, G658A, W659A, and R661A; F491A, M495A, T496A, and N497A; or K918A, V922A, R925A, and Q926A.

In some embodiments, the proteins comprise mutations: N692A/M694A/Q695A/H698A.

In some embodiments, the proteins comprise mutations: N692A/M694A/Q695A/H698A/Q926A; N692A/M694A/Q695A/Q926A; N692A/M694A/H698A/Q926A; N692A/Q695A/H698A/Q926A; M694A/Q695A/H698A/Q926A; N692A/Q695A/H698A; N692A/M694A/Q695A; N692A/H698A/Q926A; N692A/M694A/Q926A; N692A/M694A/H698A; M694A/Q695A/H698A; M694A/Q695A/Q926A; Q695A/H698A/Q926A; G582A/V583A/E584A/D585A/N588A/Q926A; G582A/V583A/E584A/D585A/N588A; T657A/G658A/W659A/R661A/Q926A; T657A/G658A/W659A/R661A; F491A/M495A/T496A/N497A/Q926A; F491A/M495A/T496A/N497A; K918A/V922A/R925A/Q926A; or 918A/V922A/R925A. See, e.g., Chen et al., "Enhanced proofreading governs CRISPR-Cas9 targeting accuracy," bioRxiv, doi.org/10.1101/160036 (Aug. 12, 2017).

In some embodiments, the variant proteins include mutations at one or more of R780, K810, R832, K848, K855, K968, R976, H982, K1003, K1014, K1047, and/or R1060, e.g., R780A, K810A, R832A, K848A, K855A, K968A, R976A, H982A, K1003A, K1014A, K1047A, and/or R1060A, e.g., K855A; K810A/K1003A/R1060A; (also referred to as eSpCas9 1.0); or K848A/K1003A/R1060A (also referred to as eSpCas9 1.1) (see Slaymaker et al., Science. 2016 Jan. 1; 351(6268):84-8).

Also provided herein are isolated nucleic acids encoding the SpCas9 variants, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The variants described herein can be used for altering the genome of a cell; the methods generally include expressing the variant proteins in the cells, along with a guide RNA having a region complementary to a selected portion of the genome of the cell. Methods for selectively altering the genome of a cell are known in the art, see, e.g., U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

The variant proteins described herein can be used in place of the SpCas9 proteins described in the foregoing references with guide RNAs that target sequences that have PAM sequences according to Tables 1, 2, or 3.

In addition, the variants described herein can be used in fusion proteins in place of the wild-type Cas9 or other Cas9 mutations (such as the dCas9 or Cas9 nickase described above) as known in the art, e.g., a fusion protein with a heterologous functional domains as described in WO 2014/124284. For example, the variants, preferably comprising one or more nuclease-reducing or killing mutation, can be fused on the N or C terminus of the Cas9 to a transcriptional activation domain or other heterologous functional domains (e.g., transcriptional repressors (e.g., KRAB, ERD, SID, and others, e.g., amino acids 473-530 of the ets2 repressor factor (ERF) repressor domain (ERD), amino acids 1-97 of the KRAB domain of KOX1, or amino acids 1-36 of the Mad mSIN3 interaction domain (SID); see Beerli et al., PNAS USA 95:14628-14633 (1998)) or silencers such as Heterochromatin Protein 1 (HP1, also known as swi6), e.g., HP1α or HP1β; proteins or peptides that could recruit long noncoding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)).

In some embodiments, the heterologous functional domain is a base editor, e.g., a deaminase that modifies cytosine DNA bases, e.g., a cytidine deaminase from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G, APOBEC3H, and APOBEC4 (see, e.g., Yang et al., J Genet Genomics. 2017 Sep. 20; 44(9):423-437); activation-induced cytidine deaminase (AID), e.g., activation induced cytidine deaminase (AICDA); cytosine deaminase 1 (CDA1) and CDA2; and cytosine deaminase acting on tRNA (CDAT). The following table provides exemplary sequences; other sequences can also be used.

| | GenBank Accession Nos. | |
|---|---|---|
| Deaminase | Nucleic Acid | Amino Acid |
| hAID/AICDA | NM_020661.3 isoform 1 | NP_065712.1 variant 1 |
| | NM_020661.3 isoform 2 | NP_065712.1 variant 2 |
| APOBEC1 | NM_001644.4 isoform a | NP_001635.2 variant 1 |
| | NM_005889.3 isoform b | NP_005880.2 variant 3 |
| APOBEC2 | NM_006789.3 | NP_006780.1 |
| APOBEC3A | NM_145699.3 isoform a | NP_663745.1 variant 1 |
| | NM_001270406.1 isoform b | NP_001257335.1 variant 2 |
| APOBEC3B | NM_004900.4 isoform a | NP_004891.4 variant 1 |
| | NM_001270411.1 isoform b | NP_001257340.1 variant 2 |
| APOBEC3C | NM_014508.2 | NP_055323.2 |
| APOBEC3D/E | NM_152426.3 | NP_689639.2 |
| APOBEC3F | NM_145298.5 isoform a | NP_660341.2 variant 1 |
| | NM_001006666.1 isoform b | NP_001006667.1 variant 2 |
| APOBEC3G | NM_021822.3 (isoform a) | NP_068594.1 (variant 1) |
| APOBEC3H | NM_001166003.2 | NP_001159475.2 (variant SV-200) |
| APOBEC4 | NM_203454.2 | NP_982279.1 |
| CDA1* | NM_127515.4 | NP_179547.1 |

*from Saccharomyces cerevisiae S288C

In some embodiments, the heterologous functional domain is a deaminase that modifies adenosine DNA bases, e.g., the deaminase is an adenosine deaminase 1 (ADA1), ADA2; adenosine deaminase acting on RNA 1 (ADAR1), ADAR2, ADAR3 (see, e.g., Savva et al., *Genome Biol.* 2012 Dec. 28; 13(12):252); adenosine deaminase acting on tRNA 1 (ADAT1), ADAT2, ADAT3 (see Keegan et al., *RNA.* 2017 September; 23(9):1317-1328 and Schaub and Keller, Biochimie. 2002 August; 84(8):791-803); and naturally occurring or engineered tRNA-specific adenosine deaminase (TadA) (see, e.g., Gaudelli et al., *Nature.* 2017 Nov. 23; 551(7681):464-471) (NP 417054.2 (*Escherichia coli* str. K-12 substr. MG1655); See, e.g., Wolf et al., *EMBO J.* 2002 Jul. 15; 21(14):3841-51). The following table provides exemplary sequences; other sequences can also be used.

| | GenBank Accession Nos. | |
|---|---|---|
| Deaminase | Nucleic Acid | Amino Acid |
| ADA (ADA1) | NM_000022.3 variant 1 | NP_000013.2 isoform 1 |
| ADA2 | NM_001282225.1 | NP_001269154.1 |
| ADAR | NM_001111.4 | NP_001102.2 |
| ADAR2 (ADARB1) | NM_001112.3 variant 1 | NP_001103.1 isoform 1 |
| ADAR3 (ADARB2) | NM_018702.3 | NP_061172.1 |
| ADAT1 | NM_012091.4 variant 1 | NP_036223.2 isoform 1 |
| ADAT2 | NM_182503.2 variant 1 | NP_872309.2 isoform 1 |
| ADAT3 | NM_138422.3 variant 1 | NP_612431.2 isoform 1 |

In some embodiments, the heterologous functional domain is an enzyme, domain, or peptide that inhibits or enhances endogenous DNA repair or base excision repair (BER) pathways, e.g., thymine DNA glycosylase (TDG; GenBank Acc Nos. NM_003211.4 (nucleic acid) and NP_003202.3 (protein)) or uracil DNA glycosylase (UDG, also known as uracil N-glycosylase, or UNG; GenBank Acc Nos. NM_003362.3 (nucleic acid) and NP_003353.1 (protein)) or uracil DNA glycosylase inhibitor (UGI) that inhibits UNG mediated excision of uracil to initiate BER (see, e.g., Mol et al., *Cell* 82, 701-708 (1995); Komor et al., *Nature.* 2016 May 19; 533(7603)); or DNA end-binding proteins such as Gam, which is a protein from the bacteriophage Mu that binds free DNA ends, inhibiting DNA repair enzymes and leading to more precise editing (less unintended base edits). See, e.g., Komor et al., *Sci Adv.* 2017 Aug. 30; 3(8):eaao4774.

See, e.g., Komor et al., *Nature.* 2016 May 19; 533(7603): 420-4; Nishida et al., *Science.* 2016 Sep. 16; 353(6305). pii: aaf8729; Rees et al., *Nat Commun.* 2017 Jun. 6; 8:15790; or Kim et al., *Nat Biotechnol.* 2017 April; 35(4):371-376) as are known in the art can also be used.

A number of sequences for domains that catalyze hydroxylation of methylated cytosines in DNA. Exemplary proteins include the Ten-Eleven-Translocation (TET) 1-3 family, enzymes that converts 5-methylcytosine (5-mC) to 5-hydroxymethylcytosine (5-hmC) in DNA.

Sequences for human TET1-3 are known in the art and are shown in the following table:

| | GenBank Accession Nos. | |
|---|---|---|
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., *Cell Cycle.* 2009 Jun. 1; 8(11):1698-710. Epub 2009 Jun. 27, for an alignment illustrating the key catalytic residues in all three Tet proteins, and the supplementary materials thereof for full length sequences (see, e.g., seq 2c); in some embodiments, the sequence includes amino acids 1418-2136 of Tet1 or the corresponding region in Tet2/3.

Other catalytic modules can be from the proteins identified in Iyer et al., 2009.

In some embodiments, the heterologous functional domain is a biological tether, and comprises all or part of (e.g., DNA binding domain from) the MS2 coat protein, endoribonuclease Csy4, or the lambda N protein. These proteins can be used to recruit RNA molecules containing a specific stem-loop structure to a locale specified by the dCas9 gRNA targeting sequences. For example, a dCas9 variant fused to MS2 coat protein, endoribonuclease Csy4, or lambda N can be used to recruit a long non-coding RNA (lncRNA) such as XIST or HOTAIR; see, e.g., Keryer-Bibens et al., *Biol. Cell* 100:125-138 (2008), that is linked to the Csy4, MS2 or lambda N binding sequence. Alternatively, the Csy4, MS2 or lambda N protein binding sequence can be linked to another protein, e.g., as described in Keryer-Bibens et al., supra, and the protein can be targeted to the dCas9 variant binding site using the methods and compositions described herein. In some embodiments, the Csy4 is catalytically inactive. In some embodiments, the Cas9 variant, preferably a dCas9 variant, is fused to FokI as described in WO 2014/204578.

In some embodiments, the fusion proteins include a linker between the dCas9 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:2) or GGGGS (SEQ ID NO:3), e.g., two, three, four, or more repeats of the GGGS (SEQ ID NO:2) or GGGGS (SEQ ID NO:3) unit. Other linker sequences can also be used.

Delivery and Expression Systems

To use the Cas9 variants described herein, it may be desirable to express them from a nucleic acid that encodes them. This can be performed in a variety of ways. For example, the nucleic acid encoding the Cas9 variant can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cas9 variant for production of the Cas9 variant. The nucleic acid encoding the Cas9 variant can also be cloned into an expression vector, for administration to a plant cell, animal cell, preferably a mammalian cell or a human cell, fungal cell, bacterial cell, or protozoan cell.

To obtain expression, a sequence encoding a Cas9 variant is typically subcloned into an expression vector that contains a promoter to direct transcription. Suitable bacterial and eukaryotic promoters are well known in the art and described, e.g., in Sambrook et al., *Molecular Cloning, A Laboratory Manual* (3d ed. 2001); Kriegler, Gene *Transfer and Expression: A Laboratory Manual* (1990); and *Current Protocols in Molecular Biology* (Ausubel et al., eds., 2010). Bacterial expression systems for expressing the engineered protein are available in, e.g., *E. coli*, *Bacillus* sp., and *Salmonella* (Palva et al., 1983, *Gene* 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cas9 variant is to be administered in vivo for gene regulation, either a constitutive or an inducible promoter can be used, depending on the particular use of the Cas9 variant. In addition, a preferred promoter for administration of the Cas9 variant can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, *Proc. Natl. Acad. Sci. USA*, 89:5547; Oligino et al., 1998, *Gene Ther.*, 5:491-496; Wang et al., 1997, *Gene Ther.*, 4:432-441; Neering et al., 1996, *Blood*, 88:1147-55; and Rendahl et al., 1998, *Nat. Biotechnol.*, 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cas9 variant, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cas9 variant, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMT010/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cas9 variants can include RNA Pol III promoters to drive expression of the guide RNAs, e.g., the H1, U6 or 7SK promoters. These human promoters allow for expression of Cas9 variants in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, *J. Biol. Chem.*, 264:17619-22; Guide to Protein Purification, in *Methods in Enzymology*, vol. 182 (Deutscher, ed., 1990)). Transformation of eukaryotic and prokaryotic cells are performed according to standard techniques (see, e.g., Morrison, 1977, *J. Bacteriol.* 132:349-351; Clark-Curtiss & Curtiss, *Methods in Enzymology* 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cas9 variant.

Alternatively, the methods can include delivering the Cas9 variant protein and guide RNA together, e.g., as a complex. For example, the Cas9 variant and gRNA can be can be overexpressed in a host cell and purified, then complexed with the guide RNA (e.g., in a test tube) to form a ribonucleoprotein (RNP), and delivered to cells. In some embodiments, the variant Cas9 can be expressed in and purified from bacteria through the use of bacterial Cas9 expression plasmids. For example, His-tagged variant Cas9 proteins can be expressed in bacterial cells and then purified using nickel affinity chromatography. The use of RNPs circumvents the necessity of delivering plasmid DNAs encoding the nuclease or the guide, or encoding the nuclease as an mRNA. RNP delivery may also improve specificity, presumably because the half-life of the RNP is shorter and there's no persistent expression of the nuclease and guide (as you'd get from a plasmid). The RNPs can be delivered to the cells in vivo or in vitro, e.g., using lipid-mediated transfection or electroporation. See, e.g., Liang et al. "Rapid and highly efficient mammalian cell engineering via Cas9 protein transfection." *Journal of biotechnology* 208 (2015): 44-53; Zuris, John A., et al. "Cationic lipid-mediated delivery of proteins enables efficient protein-based genome editing in vitro and in vivo." *Nature biotechnology* 33.1 (2015): 73-80; Kim et al. "Highly efficient RNA-guided genome editing in human cells via delivery of purified Cas9 ribonucleoproteins." *Genome research* 24.6 (2014): 1012-1019.

The present invention includes the vectors and cells comprising the vectors.

EXAMPLES

The invention is further described in the following examples, which do not limit the scope of the invention described in the claims.

Methods

The following materials and methods were used in Example 1.

Plasmids and Oligonucleotides

Sequences of oligonucleotides used to amplify endogenous human gene target sites for T7E1 assays are found in Table 4.

TABLE 4

| Primers used for T7E1 experiments | | SEQ ID NO: |
|---|---|---|
| sequence | description | |
| GGAGCAGCTG GTCAGAGGGG | forward primer targeted to EMX1 in U2OS human cells | 4 |
| CCATAGGGAA GGGGACACT GG | reverse primer targeted to EMX1 in U2OS human cells | 5 |
| GGGCCGGGAA AGAGTTGCTG | forward primer targeted to FANCF in U2OS human cells | 6 |
| GCCCTACATC TGCTCTCCCT CC | reverse primer targeted to FANCF in U2OS human cells | 7 |
| CCAGCACAAC TTACTCGCAC TTGAC | forward primer targeted to RUNX1 in U2OS human cells | 8 |
| CATCACCAAC CCACAGCCAA GG | reverse primer targeted to RUNX1 in U2OS human cells | 9 |

TABLE 4-continued

| Primers used for T7E1 experiments | | SEQ ID NO: |
|---|---|---|
| sequence | description | |
| GATGAGGGCT CCAGATGGCA C | forward primer targeted to VEGFA in U2OS human cells | 10 |
| GAGGAGGGAG CAGGAAAGTG AGG | reverse primer targeted to VEGFA in U2OS human cells | 11 |

Bacterial Cas9/sgRNA expression plasmids were constructed as previously described (Kleinstiver et al., Nature 2015) with two T7 promoters to separately express Cas9 and the sgRNA. Bacterial expression plasmids containing variable amino acids at positions D1135, 51136, G1218, E1219, R1335, and T1337 were generated by cloning oligonucleotides encoding randomized codons at these positions into the parental SpCas9 bacterial expression vectors (FIG. 1).

For expression in human cells, point mutations in SpCas9 were generated by isothermal assembly into a pCMV-T7-hSpCas9-NLS-3xFLAG vector (JDS246; sequences found here at addgene.org/43861/sequences/).

Plasmids for U6 expression of sgRNAs (into which desired spacer oligos can be cloned) were generated by cloning appropriate annealed oligos into BsmBI digested BPK1520.

Bacterial-Based Positive Selection Assay for Evolving SpCas9 Variants

Competent *E. coli* BW25141(λDE3)[23] containing a positive selection plasmid (with embedded target site) were transformed with Cas9/sgRNA-encoding plasmids. Following a 60 minute recovery in SOB media, transformations were plated on LB plates containing either chloramphenicol (non-selective) or chloramphenicol+10 mM arabinose (selective).

To select for SpCas9 variants that can cleave novel PAMs, plasmids encoding randomized D1135X/S1136X/G1218X/E1219X/R1335X/T1337X SpCas9 libraries were electroporated into *E. coli* BW25141(λDE3) cells that already harbored a positive selection plasmid that encodes a target site with a PAM of interest. Surviving colonies were grown overnight, miniprepped to extract the SpCas9-expression plasmid, and retransformed individually into *E. coli* BW25141(λDE3) cells containing a positive selection with the previously described PAM sequence to re-test linkage of the survival phenotype to those plasmids and thereby eliminate false positive clones. Generally ~300 clones were re-screened in follow-up experiments. The SpCas9 expression plasmids of bona fide surviving colonies in the secondary screen were sequenced to identify the amino acids at positions D1135, 51136, G1218, E1219, R1335, and/or T1337 that led to the alteration in specificity (see Tables 1-3). Mutations observed in the sequenced clones were chosen for further assessment based on their frequency in surviving clones, and (in some cases) activities in a human cell-based EGFP disruption assay.

Human Cell Culture and Transfection

U2OS cells and U2OS.EGFP cells harboring a single integrated copy of an EGFP-PEST reporter gene (Reyon, D. et al. FLASH assembly of TALENs for high-throughput genome editing. *Nat Biotechnol* 30, 460-465 (2012)) were cultured in Advanced DMEM medium (Life Technologies) with 10% FBS, penicillin/streptomycin, and 2 mM Gluta- MAX (Life Technologies) at 37° C. with 5% CO2. Cell line identities were validated by STR profiling (ATCC) and deep sequencing, and cells were tested bi-weekly for *mycoplasma* contamination. U2OS.EGFP culture medium was additionally supplemented with 400 μg/mL G418. Cells were co-transfected with 750 ng Cas9 plasmid and 250 ng sgRNA plasmid using the DN-100 program of a Lonza 4D-nucleofector following the manufacturer's instructions. Cas9 plasmid transfected together with an empty U6 promoter plasmid was used as a negative control for all human cell experiments.

Human Cell EGFP Disruption Assay

EGFP disruption experiments were performed as previously described (Fu, Y. et al. High-frequency off-target mutagenesis induced by CRISPR-Cas nucleases in human cells. *Nat Biotechnol* 31, 822-826 (2013); Reyon, D. et al. FLASH assembly of TALENs for high-throughput genome editing. *Nat Biotechnol* 30, 460-465 (2012)). Approximately 52 hours post-transfection, a Fortessa flow cytometer (BD Biosciences) was used to measure EGFP fluorescence in transfected U2OS.EGFP cells. Negative control transfections of Cas9 and empty U6 promoter plasmids were used to establish background EGFP loss at ~2.5% for all experiments.

T7E1 Assay

T7E1 assays were performed as previously described[15]. For U2OS human cells, genomic DNA was extracted from transfected cells ~72 hours post-transfection using the Agencourt DNAdvance Genomic DNA Isolation Kit (Beckman Coulter Genomics). Target loci from human cell genomic DNA were amplified using the primers listed in Table 4. Roughly 200 ng of purified PCR product was denatured, annealed, and digested with T7E1 (New England BioLabs). Mutagenesis frequencies were quantified using a Qiaxcel capillary electrophoresis instrument (Qlagen), as previously described[15].

Example 1

To further expand the utility of SpCas9 by enabling targeting of currently inaccessible PAM sequences, we conceived of an alternate strategy to select for SpCas9 variants capable of recognizing novel PAM sequences. Having established previously that certain positions within the SpCas9 coding sequence are important for PAM recognition (Kleinstiver et al., *Nature* 2015), we conducted a focused mutagenesis approach where we randomized the amino acids at six positions to generate a library of SpCas9 variants with diverse codon usage within three separate regions of the PAM interacting domain: D1135/S1136, G1218/E1219, and R1335/T1337. To do so, we sequentially cloned in randomized oligonucleotide cassettes encoding NNS nucleotide triplets (where N is any nucleotide and S is G or C) at the codons of SpCas9 that contain encode these six amino acids (FIG. 1A). The resulting library of SpCas9 variants was then screened in our bacterial positive selection assay as previously described (Kleinstiver et al., *Nature* 2015), against target sites that encode various NGNN PAM sequences (FIG. 1B). Briefly, bacteria can only survive selective conditions (plating on 10 mM arabinose, which induces transcription of the ccdB toxic gene) if SpCas9 can recognize the target site (PAM and spacer sequence) encoded in the positive selection plasmid. Strong PAM recognition will lead to hydrolysis of the selection plasmid, preventing induction of ccdB expression and allowing bacterial growth. Thus, while screening SpCas9 libraries, colonies that grow on media containing 10 mM arabinose are expected to encode an SpCas9 PAM variant that can target alternate PAMs (FIG. 1B).

We first screened the randomized D1135X/S1136X/G1218X/E1219X/R1335X/T1337X SpCas9 library (SpCas9-XXXXXX, where X is any amino acid) on positive selection plasmids that encode target sites with NGTG, NGTT, NGTC, and NGTA PAMs. For each different PAM selection, 48 surviving colonies from the arabinose selection were picked and grown overnight in chloramphenicol containing media to recover the nuclease encoding plasmid. To reduce false positive rate in the primary screen, all putative PAM variant plasmids were subsequently re-screened against positive selection plasmids encoding the target site and PAM against which they were originally screened (data not shown). A subset of bona fide variants with at least 50% survival in this re-screening assay were sequenced to identify the amino acids at residues 1135, 1136, 1218, 1219, 1335, 1337 (Table 1), and then these variants were screened more broadly against NGTG, NGTT, NGTC, and NGTA PAMs to assess activity against NGTN sites (FIGS. 2*a-b* and Table 1). Note: subsequent to this point, in bacterial assays SpCas9 variants will be described by their variant number (vNGTN- #) or in human assays by their 'amino acid name', where the amino acid name will be in the form SpCas9-XXXXXX with the six Xs representing the amino acids identities at positions 1135, 1136, 1218, 1219, 1335, and 1337 (found in Tables 1-3). Re-screening identified a few trends, where in some cases the variant had the highest activity on the NGTN PAM against which it was originally selected (ex. vNGTN-1, -3, -12, -27, -28, etc.), that some variants could target a combination of NGTN PAMs (ex. vNGTN-15, -31, -35, etc., that can target NGTC and NGTA), and some variants can target all NGTN PAMs (ex. vNGTN-9, -10, -30, etc.) (FIGS. 2A-B and Table 1). Based on these results, novel variants were rationally designed based on frequently occurring amino acids at positions 1135, 1136, 1218, 1219, 1335, and 1337 in the clones that performed well in the initial screens. These rationally designed NGTN variants were assessed in the bacterial screen against NGTG, NGTT, NGTC, and NGTA PAMs (FIGS. 2C-F), and in some cases also screened against NGAN PAMs (NGAG, NGAT, NGAC, NGAA; FIGS. 2C, 2E-F). Again a number of interesting variants were identified with properties consistent with the preferences above, but notably some additional variants were identified that could impart a preference on the 4$^{th}$ position of the PAM (ex., vNGTG-37 that could target NGTG or NGAG PAMs or vNGTG-18 and -41 on NGTC and NGAC PAMs, etc.), additional variants that can target all NGTN PAMs (ex. vNGTN-40, -46, -48, etc.), and variants that can target all or nearly all NGTN or NGAN PAMs (ex. vNGTN-7, -44, -59, etc.; FIGS. 2C-F and Table 1).

Having identified several variants that can target NGTN PAM sites in bacteria, we sought to determine whether these preferences would translate to bona fide activity in human cells. In in initial screen of twelve different NGTN PAM variants in our human U2OS EGFP-disruption assay, we identified variants that could robustly target NGTT and NGTG PAMs (ex. SpCas9-GRKIQK, -VAKLLR, -VRKLLR, etc.), and some that could modify all NGTN PAM sites (ex. SpCas9-LRSVQL, -IRAVQL, etc.) (FIG. 3A). Further screening of a subset of these variants and additional rationally designed variants in the human cell EGFP-disruption assay identified SpCas9-LRSVQL, -LRKIQK, -LRSVQK, and others as promising variants that can target NGTN PAM sequences (FIG. 3B). To more stringently characterize the activity of SpCas9-LRSVQL on NGTN PAM sequences in human cells, we examined the activity of this nuclease variant across 32 different endogenous sites across the EMX1, FANCF, and RUNX1 genes in human U2OS cells. This analysis revealed robust activity of SpCas9-LRSVQL on various endogenous sites bearing NGTG, NGTA, NGTC, and NGTT PAMs (FIG. 3C, demonstrating that our selected and rationally designed PAM variants can function efficiently across numerous loci not previously targetable with published SpCas9 variants.

We have previously described an SpCas9 variant that can effectively target NGCG PAM sites (Kleinstiver et al., *Nature*, 2015), called SpCas9-VRER (that encodes D1135V/ G1218R/R1335E/T1337R substitutions). While this variant enables targeting of previously inaccessible sites, it is restricted to activity on sites with an extended NGCG PAM. To expand the utility of SpCas9 PAM variants by potentially targeting all NGCN PAMs to now include NGCT, NGCC, and NGCA we performed similar selections to those described above, but screened the SpCas9-XXXXXX library against positive selection plasmids harboring a target site with either an NGCG, NGCT, NGCC, or NGCA PAM (FIGS. 4A-B and Table 2). Much like we observed with the NGTN selections, re-screening of NGCN variants identified cases where the variant had the highest activity on the NGCN PAM against which it was originally selected (ex. vNGCN-3, -8, -9, -17, etc.), that some variants could target a combination of NGCN PAMs (ex. vNGCN-10, etc., that can target NGCT, NGCC and NGCA), and some variants can target all NGCN PAMs (ex. vNGCN-1, -2, -5, -18, -26 etc.) (FIGS. 4A-B and Table 2). Various rationally generated NGCN variants were cloned based on observations of amino acid enrichment in SpCas9-XXXXXX selected clones, and tested in bacteria for activity against NGCN PAMs (FIGS. 4A-B, Table 2, and data not shown).

Next, we examined the activities of various NGCN selected SpCas9 PAM variants in our U2OS EGFP-disruption assay to determine whether their re-targeted PAM preferences and nuclease activities could be recapitulated in human cells (FIGS. 5A-D). We observed activity of numerous variants against NGCA PAMs (SpCas9-MQKSER, -LWRVVA, -LWLETR, etc.; FIG. 5A), NGCC PAMs (SpCas9-MQKSER, -LSRWQR, -ICCCER, etc.; FIG. 5A), NGCT PAMs (SpCas9-MQKSER; FIG. 5C), or NGCC and NGCT PAMs (SpCas9-MQKSER, -VRKSER, -ICKSER, etc.; FIG. 5C). Further testing of the SpCas9-MQKSER, -VRKSER, -ICKSER variants against 15 total NGCA, NGCC, NGCT, and NGCG sites revealed robust activity of each variant against all classes of NGCN PAMs (FIG. 5E). In some cases, these variants can outperform the published SpCas9-VRER (e.g., as shown in FIGS. 5B-C), though this was generally on PAMs that were previously shown to be ineffectively targeted by SpCas9-VRER. Collectively, these new variants expand SpCas9 targeting to NGCT, NGCC, and NGCA instead of the formerly accessible NGCG, with SpCas9-MQKSER and other variants having robust activity on all NGCN PAMs.

Additionally, we have also previously described SpCas9 variant that can effectively target NGAN PAM sites, called SpCas9-VQR (D1135V/R1335Q/T1337R; Kleinstiver et al., *Nature*, 2015), and SpCas9-VRQR (D1135V/G1218R/ R1335Q/T1337R; Kleinstiver and Pattanayak et al., *Nature*, 2016). However, these variants have a preference for subclasses of NGAN PAMs in the order of NGAG>NGAA=NGAT>NGAC, i.e., they have suboptimal activity against NGAC PAM sites. To potentially improve SpCas9 targeting of NGAN PAMs, we performed selections with the SpCas9-XXXXXX library as described above on positive selection plasmids encoding NGAG, NGAT, NGAC, and NGAA PAMs (FIGS. 6A-B and Table 3). Re-screening of NGAN variants revealed clones that had the highest activity on the NGAN PAM against which it was originally selected (ex. vNGAN-1, -2, -17, -26 through -30, etc. on NGAG, vNGAN-32 on NGAT, vNGAN-4, -5, -40, -41, etc. on NGAC, etc.), that some variants could target a combination of NGAN PAMs (ex. vNGAN-20, -21, etc., that can target NGAT and NGAC, or vNGAN-22 that can target NGAG and NGAC), and some variants can target all NGAN PAMs (ex. vNGAN-3, -13, -25, -31 etc.) (FIGS. 6A-B and Table 3).

Because numerous SpCas9-XXXXXX variants revealed strong NGAC PAM targeting in the bacterial screen, many variants were sub-cloned into our human expression vector to examine activity in our human cell U2OS EGFP-disruption assay. An initial screen of a subset of variants against single NGAA, NGAC, NGAT and NGAG PAM sites in EGFP revealed that certain variants could potentially outperform SpCas9-VQR at sites harboring NGAC PAMs (FIG. 7A). More extensive testing of variants from FIG. 7A and additional selected variants revealed that multiple SpCas9 variants had improved activity relative to SpCas9-VRQR on some or all four of the NGAC PAM sites examined in the EGFP disruption assay (FIG. 7B), including SpCas9-LRSVRS, -MRARKE, -SRQMRG, and others.

Figure 8:
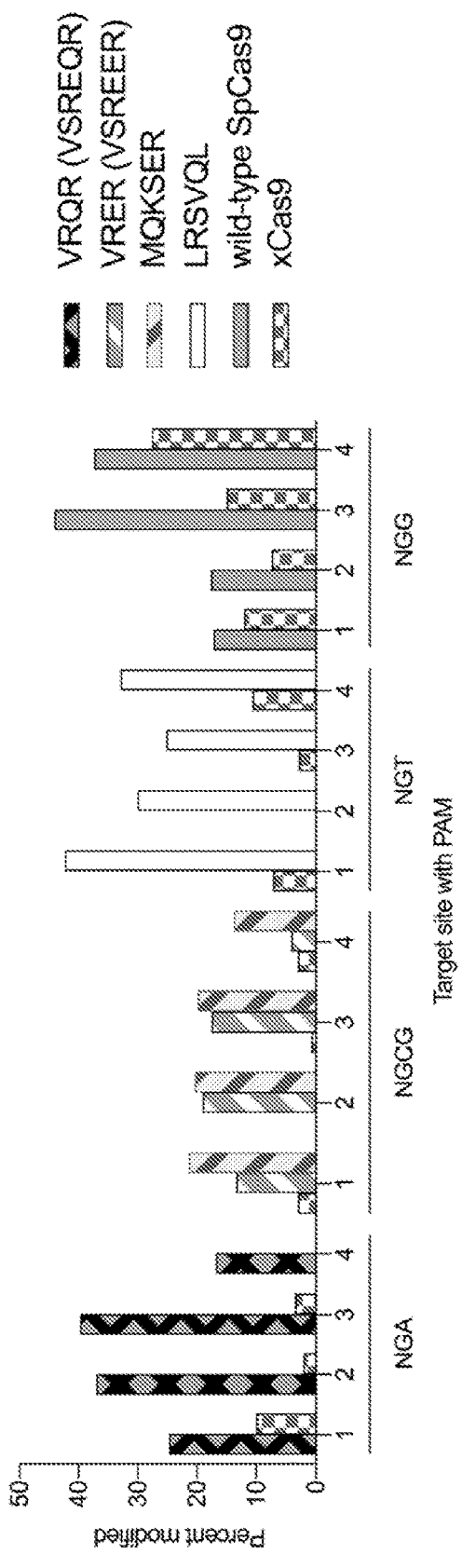
FIG. 8. Comparison of the nuclease activities of SpCas9 PAM variants to xCas9 in human cells. Endogenous gene disruption activities were assessed by T7E1 assay.

We then compared the activity of our SpCas9 variants to a recently described SpCas9 PAM variant called xCas9 that has a reported relaxed NG PAM preference (Hu et al., *Nature* volume 556, pages 57-63 (5 Apr. 2018)). Consistent with our previous results, we observed robust nuclease targeting (between 15-50% as assessed by T7E1 assay) of sites with NGA PAMs with the VRQR variant (also known as VSREQR), of sites with NGCG PAMs with the VRER (also known as VSREER) and MQKSER variants, and of sites with NGT PAMs with the LRSVQL variant (FIG. 8). However, with the xCas9 variant, no targeting of sites with NGA, NGCG, or NGT PAMs was observed at greater than 10% efficiency; furthermore, we observed that xCas9 was on average about 2-fold less effective at targeting sites with NGG PAMs as compared to wild-type SpCas9 (FIG. 8). These results demonstrate that our SpCas9 PAM variants are more effective nucleases against a variety of PAMs when compared to xCas9.

Example 2

The ability to perform precise single base editing events has recently been demonstrated using engineered SpCas9 base editor (BE) constructs (see, e.g., Komor et al., *Nature*. 2016 May 19; 533(7603):420-4; Nishida et al., *Science*. 2016 Sep. 16; 353(6305); Kim et al., *Nat Biotechnol*. 2017 April; 35(4):371-376; Komor et al., *Sci Adv*. 2017 August 30; 3(8):eaao4774; and Gaudelli et al., *Nature*. 2017 November 23; 551(7681):464-471), which exploit the formation of SpCas9-gRNA formed R-loops that cause ssDNA accessibility of the non-target DNA strand. The fusion of heterologous cytidine or adenine deaminase enzymatic domains to SpCas9 can therefore act on the exposed ssDNA strand, leading to the efficient introduction of C to T changes (so-called cytosine base editors, or CBEs), or A to G (so-called adenosine base editors, or ABEs), respectively. Because cellular base-excision repair (BER) employs uracil DNA glycosylase (UDG; also known as uracil N-glycosylase, or UNG) to excise uracil bases, this endogenous process can effectively reverse edits generated by cytidine BEs because the deamination of cytidine leads to a uracil intermediate. Therefore, to improve the efficiency of cytidine BEs, heterologous effector domains such as uracil glycosylase inhibitor (UGI) can also be fused to SpCas9 to inhibit UDG, subverting the initiation of BER and increasing the effectiveness of cytidine BEs.

Figure 9A:
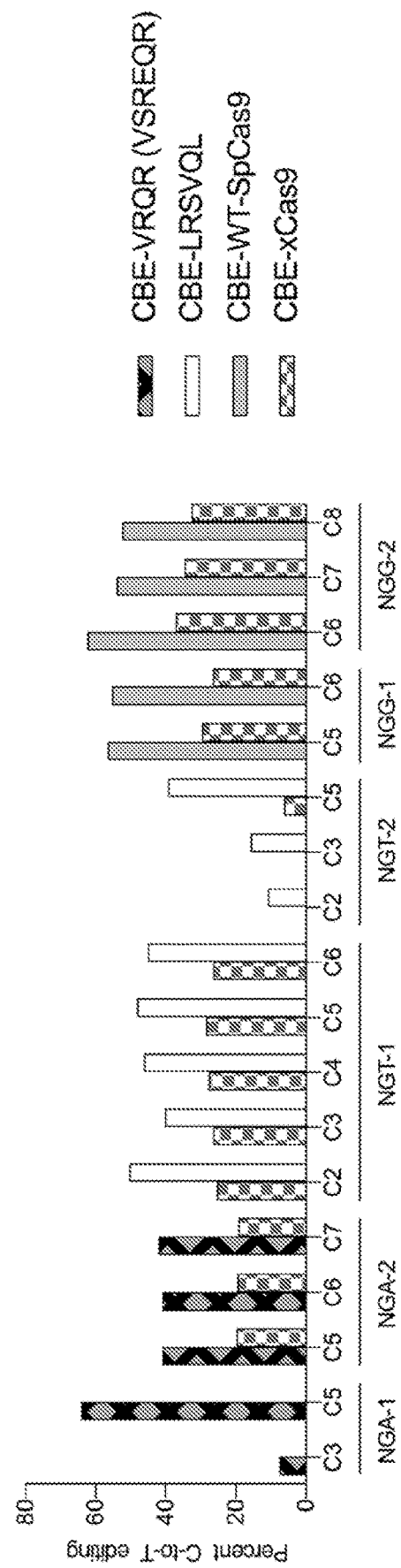
FIGS. 9A-B. Comparison of the base editing activities of SpCas9 PAM variants to xCas9 on endogenous sites in human cells. (A) BE3 versions (Komor et al., *Nature.* 2016 May 19; 533(7603):420-4) of SpCas9 PAM variants were tested for C-to-T base editing activity, as assessed by targeted deep sequencing and analysis performed with CRISPResso (Pinello et al., *Nat Biotechnol.* 2016 Jul. 12; 34(7): 695-697). *Nat Biotechnol.* 2016 Jul. 12; 34(7): 695-697). Edited cytosine nucleotides labeled on the x-axis are numbered starting at position 1 as the most PAM-distal position in the Cas9 target sequence. (B) ABE7.10 versions (Gaudelli et al., *Nature.* 2017 Nov. 23; 551(7681):464-471) of SpCas9 PAM variants were tested for A-to-G base editing activity, as assessed by targeted deep sequencing and analysis performed with CRISPResso. Edited adenosine nucleotides labeled on the x-axis are numbered starting at position 1 as the most PAM-distal position in the Cas9 target sequence.

We therefore sought to determine whether the expanded targeting range of our SpCas9 PAM variants could improve the utility of base editors by enabling editing of previously inaccessible sites. To do so, we constructed BE3 (Komor et al., Nature. 2016 May 19; 533(7603):420-4) PAM variants to generate CBEs capable of recognizing sites with NGA and NGT PAMs. We found that on sites with NGA PAMs the CBE-VRQR variant exhibited between 7.5% to 64.2% conversion of Cs to Ts in the editing window, whereas xCas9 exhibited 0%-19.9% C-to-T editing on the same sites (FIG. 9A). Similarly, on sites with NGT PAMs the CBE-LRSVQL variant exhibited between 10.8% to 50.3% conversion of Cs to Ts, whereas CBE-xCas9 exhibited 0%-28.5% C-to-T editing on the same sites (FIG. 9A). We also observed a marked decrease in C-to-T editing activity with CBE-xCas9 (26.7%-37.2%) compared to wild-type SpCas9 (52.5%-62.4%) on sites with NGG PAMs (FIG. 9A). These results demonstrate that the BE3 versions of VRQR and LRSVQL are effective CBEs on sites with NGA and NGT PAMs, respectively, at rates ~2-fold greater than with xCas9.

Figure 9B:
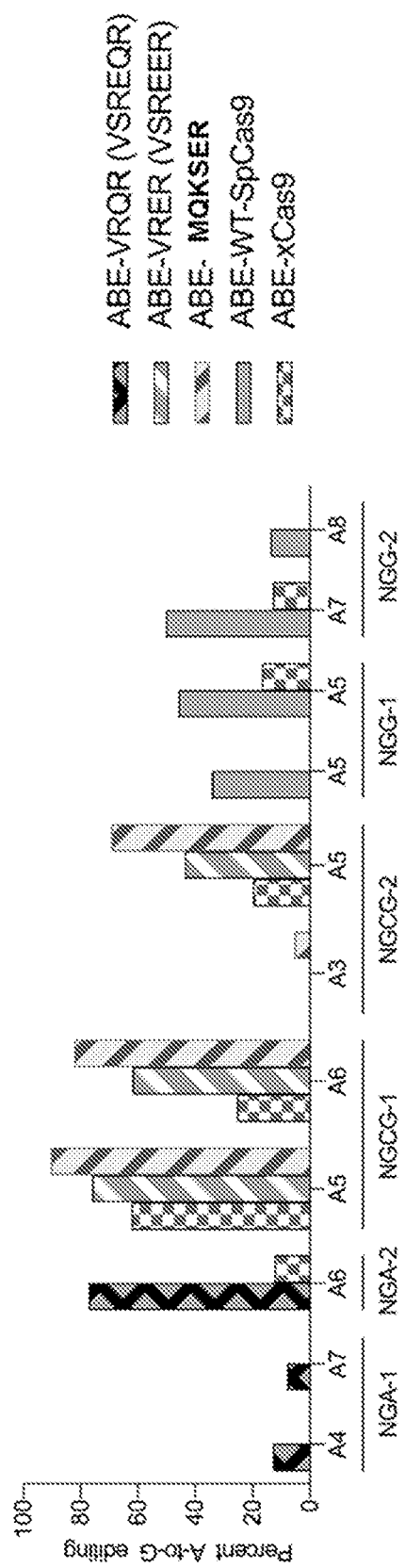

Next, we constructed ABE(7.10) (Gaudelli et al., Nature. 2017 Nov. 23; 551(7681):464-471) versions of our PAM variants to determine their effectiveness as ABEs that mediate A-to-G conversion in human cells. We observed strong A-to-G editing activity with ABE-VRQR (8.0%-77.3%) on sites with NGA PAMs, compared to 0%-12.5% editing observed with ABE-xCas9 (FIG. 9B). Similarly, on sites with NGCG PAMs, the ABE-VRER (0%-75.9%) and ABE-MQKSER (5.4%-90.4%) variants once again outperformed ABE-xCas9 (0%-62.3%) for A-to-G editing (FIG. 9B). We also observed decreased A-to-G editing with ABE-xCas9 (0%-16.9%) compared to wild-type SpCas9 (13.9%-50.4%) on sites with NGG PAMs (FIG. 9B). Our results reveal that the ABE(7.10) version of VRQR is effective at mediating A-to-G editing on sites with NGA PAMs, and that the ABE(7.10) versions of VRER and MQKSER are effective on sites with NGCG PAMs.

REFERENCES

1. Sander, J. D. & Joung, J. K. CRISPR-Cas systems for editing, regulating and targeting genomes. *Nat Biotechnol* 32, 347-355 (2014).
2. Hsu, P. D., Lander, E. S. & Zhang, F. Development and applications of CRISPR-Cas9 for genome engineering. *Cell* 157, 1262-1278 (2014).
3. Doudna, J. A. & Charpentier, E. Genome editing. The new frontier of genome engineering with CRISPR-Cas9. *Science* 346, 1258096 (2014).
4. Barrangou, R. & May, A. P. Unraveling the potential of CRISPR-Cas9 for gene therapy. *Expert Opin Biol Ther* 15, 311-314 (2015).
5. Jinek, M. et al. A programmable dual-RNA-guided DNA endonuclease in adaptive bacterial immunity. *Science* 337, 816-821 (2012).
6. Sternberg, S. H., Redding, S., Jinek, M., Greene, E. C. & Doudna, J. A. DNA interrogation by the CRISPR RNA-guided endonuclease Cas9. *Nature* 507, 62-67 (2014).
7. Hsu, P. D. et al. DNA targeting specificity of RNA-guided Cas9 nucleases. *Nat Biotechnol* 31, 827-832 (2013).
8. Tsai, S. Q. et al. GUIDE-seq enables genome-wide profiling of off-target cleavage by CRISPR-Cas nucleases. *Nat Biotechnol* 33, 187-197 (2015).
9. Hou, Z. et al. Efficient genome engineering in human pluripotent stem cells using Cas9 from Neisseria meningitidis. *Proc Natl Acad Sci USA* (2013).
10. Fonfara, I. et al. Phylogeny of Cas9 determines functional exchangeability of dual-RNA and Cas9 among orthologous type II CRISPR-Cas systems. *Nucleic Acids Res* 42, 2577-2590 (2014).
11. Esvelt, K. M. et al. Orthogonal Cas9 proteins for RNA-guided gene regulation and editing. *Nat Methods* 10, 1116-1121 (2013).
12. Cong, L. et al. Multiplex genome engineering using CRISPR/Cas systems. *Science* 339, 819-823 (2013).
13. Horvath, P. et al. Diversity, activity, and evolution of CRISPR loci in *Streptococcus thermophilus*. *J Bacteriol* 190, 1401-1412 (2008).
14. Anders, C., Niewoehner, O., Duerst, A. & Jinek, M. Structural basis of PAM-dependent target DNA recognition by the Cas9 endonuclease. *Nature* 513, 569-573 (2014).
15. Reyon, D. et al. FLASH assembly of TALENs for high-throughput genome editing. *Nat Biotechnol* 30, 460-465 (2012).
16. Fu, Y. et al. High-frequency off-target mutagenesis induced by CRISPR-Cas nucleases in human cells. *Nat Biotechnol* 31, 822-826 (2013).
17. Chen, Z. & Zhao, H. A highly sensitive selection method for directed evolution of homing endonucleases. *Nucleic Acids Res* 33, e154 (2005).
18. Doyon, J. B., Pattanayak, V., Meyer, C. B. & Liu, D. R. Directed evolution and substrate specificity profile of homing endonuclease I-SceI. *J Am Chem Soc* 128, 2477-2484 (2006).
19. Jiang, W., Bikard, D., Cox, D., Zhang, F. & Marraffini, L. A. RNA-guided editing of bacterial genomes using CRISPR-Cas systems. *Nat Biotechnol* 31, 233-239 (2013).
20. Mali, P. et al. RNA-guided human genome engineering via Cas9. *Science* 339, 823-826 (2013).
21. Hwang, W. Y. et al. Efficient genome editing in zebrafish using a CRISPR-Cas system. *Nat Biotechnol* 31, 227-229 (2013).
22. Chylinski, K., Le Rhun, A. & Charpentier, E. The tracrRNA and Cas9 families of type II CRISPR-Cas immunity systems. *RNA Biol* 10, 726-737 (2013).
23. Kleinstiver, B. P., Fernandes, A. D., Gloor, G. B. & Edgell, D. R. A unified genetic, computational and experimental framework identifies functionally relevant residues of the homing endonuclease I-BmoI. *Nucleic Acids Res* 38, 2411-2427 (2010).
24. Gagnon, J. A. et al. Efficient mutagenesis by Cas9 protein-mediated oligonucleotide insertion and large-scale assessment of single-guide RNAs. *PLoS One* 9, e98186 (2014).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

Selection results and activity in bacteria of variants against NGTN PAMs

| Sample # | Originally selected against (NGTN) | Approximate survival in bacterial assay against: | | | | Variant name | Amino acid substitutions in variant: | | | | | |
|---|---|---|---|---|---|---|---|---|---|---|---|---|
| | | NGTG | NGTT | NGTC | NGTA | | D1135 | S1136 | G1218 | E1219 | R1335 | T1337 |
| vNGTN-1 | G | 30% | 0% | 3% | 3% | SpCas9-DKVHVR | D | K | V | H | V | R |
| VNGTN-2 | G | 15% | 40% | 40% | 40% | SpCas9-NRMMRT | N | R | M | M | R | T |
| VNGTN-3 | G | 100% | 40% | 40% | 10% | SpCas9-ASQLMR | A | S | Q | L | M | R |
| VNGTN-4 | G | 100% | 40% | 10% | 40% | SpCas9-LRQYTR | L | R | Q | Y | T | R |
| vNGTN-5 | G | 100% | 15% | 10% | 20% | SpCas9-GCACMR | G | C | A | C | M | R |
| VNGTN-6 | G | 100% | 50% | 30% | 20% | SpCas9-SRSCMV | S | R | S | C | M | V |
| VNGTN-7 | T | 100% | n/a | n/a | n/a | SpCas9-LWKIQK | L | W | K | I | Q | K |
| VNGTN-8 | T | 50% | 50% | 20% | 30% | SpCas9-YSAFCC | Y | S | A | F | C | C |
| VNGTN-9 | T | 100% | 100% | 70% | 80% | SpCas9-IRAVQL | I | R | A | V | Q | L |
| VNGTN-10 | T | 100% | 80% | 70% | 60% | SpCas9-SWRVVV | S | W | R | V | V | V |
| VNGTN-11 | T | 100% | 80% | 70% | 60% | SpCas9-SWKVLK | S | W | K | V | L | K |
| VNGTN-12 | T | 3% | 80% | 3% | 3% | SpCas9-LWSVGG | L | W | S | V | G | G |
| VNGTN-13 | C | — | — | 10% | 20% | SpCas9-SRAAKW | S | R | A | A | K | W |
| VNGTN-14 | C | — | — | 10% | 10% | SpCas9-RNGWRI | R | N | G | W | R | I |
| VNGTN-15 | C | 0% | 3% | 90% | 90% | SpCas9-TAHFKV | T | A | H | F | K | V |
| VNGTN-16 | C | — | — | 80% | 80% | SpCas9-MSGVKC | M | S | G | V | K | C |
| VNGTN-17 | | — | — | 50% | 50% | SpCas9-VMRCKL | V | M | R | C | K | L |
| VNGTN-18 | C | — | — | 75% | 75% | SpCas9-LRSVRS | L | R | S | V | R | S |
| VNGTN-19 | A | — | — | n/a | 30% | SpCas9-RWNLRR | R | W | N | L | R | R |
| VNGTN-20 | A | 3% | 3% | 0% | 0% | SpCas9-VRCVRC | V | R | C | V | R | C |
| VNGTN-21 | A | — | — | 20% | 20% | SpCas9-GRTSRC | G | R | T | S | R | C |
| VNGTN-22 | A | — | — | 65% | 65% | SpCas9-LKLCKR | L | K | L | C | K | R |
| VNGTN-23 | A | — | — | 70% | 65% | SpCas9-AKLCRT | A | K | L | C | R | T |
| VNGTN-24 | A | — | — | 75% | 100% | SpCas9-SKTLRP | S | K | T | L | R | P |
| VNGTN-25 | G | 50% | 20% | 40% | 40% | SpCas9-SRRSQR | S | R | R | S | Q | R |
| VNGTN-26 | G | 50% | 20% | 40% | 50% | SpCas9-DKVHVR | D | K | V | H | V | R |
| VNGTN-27 | G | 50% | — | — | — | SpCas9-GAKLLR | G | A | K | L | L | R |
| VNGTN-28 | T | 20% | 100% | 40% | 40% | SpCas9-MWAFGC | M | W | A | F | G | C |
| VNGTN-29 | T | — | 35% | — | — | SpCas9-GWRVTW | G | W | R | V | T | W |
| VNGTN-30 | T | 85% | 100% | 100% | 80% | SpCas9-MWVHLN | M | W | V | H | L | N |
| VNGTN-31 | C | — | — | 100% | 85% | SpCas9-TWSMRG | T | W | S | M | R | G |
| VNGTN-32 | C | — | — | 80% | 35% | SpCas9-ISGTKN | I | S | G | T | K | N |
| VNGTN-33 | C | — | — | 50% | 45% | SpCas9-SRAAKW | S | R | A | A | K | W |
| vNGTN-34 | A | 75% | 75% | 50% | 40% | SpCas9-KCAFCC | K | C | A | F | C | C |
| VNGTN-35 | A | — | — | 100% | 100% | SpCas9-KRRCKV | K | R | R | C | K | V |
| VNGTN-36 | A | — | — | 90% | 100% | SpCas9-MWGGRC | M | W | G | G | R | C |

TABLE 1-continued

Selection results and activity in bacteria of variants against NGTN PAMs

| Sample # | Originally selected against (NGTN) | Approximate survival in bacterial assay against: | | | | Variant name | Amino acid substitutions in variant: | | | | | |
|---|---|---|---|---|---|---|---|---|---|---|---|---|
| | | NGTG | NGTT | NGTC | NGTA | | D1135 | S1136 | G1218 | E1219 | R1335 | T1337 |
| VNGTN-37 | created variant | 80% | — | 5% | 3% | SpCas9-VSKLLR | V | S | K | L | L | R |
| VNGTN-38 | created variant | 90% | 20% | 10% | 10% | SpCas9-VRKLLR | V | R | K | L | L | R |
| vNGTN-27* | G | 75% | — | — | — | SpCas9-GAKLLR | G | A | K | L | L | R |
| VNGTN-39 | created variant | 50% | 95% | 5% | 2% | SpCas9-VSAVQL | V | S | A | V | Q | L |
| VNGTN-40 | created variant | 90% | 95% | 95% | 50% | SpCas9-VRAVQL | V | R | A | V | Q | L |
| vNGTN-9* | T | 90% | 95% | 95% | 90% | SpCas9-IRAVQL | I | R | A | V | Q | L |
| VNGTN-41 | created variant | — | — | 95% | 90% | SpCas9-VSSVRS | V | S | S | V | R | S |
| VNGTN-42 | created variant | — | — | 95% | 90% | SpCas9-VRSVRS | V | R | S | V | R | S |
| vNGTN-18* | C | — | — | 100% | 95% | SpCas9-LRSVRS | L | R | S | V | R | S |
| VNGTN-43 | N/A | — | — | — | — | SpCas9-SRGERT | S | R | G | E | R | T |
| VNGTN-44 | N/A | 80% | 35% | 100% | 90% | SpCas9-SRMHCK | S | R | M | H | C | K |
| VNGTN-45 | created variant | | | | | SpCas9-GRKIQK | G | R | K | I | Q | K |
| VNGTN-46 | created variant | | | | | SpCas9-GWKLLR | G | W | K | L | L | R |
| VNGTN-47 | created variant | | | | | SpCas9-GWKQQK | G | W | K | Q | Q | K |
| VNGTN-48 | created variant | | | | | SpCas9-VAKLLR | V | A | K | L | L | R |
| VNGTN-49 | created variant | | | | | SpCas9-VAKIQK | V | A | K | I | Q | K |
| vNGTN-50 | created variant | | | | | SpCas9-VAKILR | V | A | K | I | L | R |
| VNGTN-51 | created variant | | | | | SpCas9-GRKILR | G | R | K | I | L | R |
| VNGTN-52 | created variant | — | — | 100% | 90% | SpCas9-VRKLRS | V | R | K | L | R | S |
| VNGTN-38 | created variant | 100% | 85% | 60% | 50% | SpCas9-VRKLLR | V | R | K | L | L | R |
| VNGTN-53 | created variant | 100% | 100% | 100% | 100% | SpCas9-LRSVQL | L | R | S | V | Q | L |
| vNGTN-18 | C | — | 1% | 100% | 100% | SpCas9-LRSVRS | L | R | S | V | R | S |
| VNGTN-54 | created variant | — | 5% | 100% | 100% | SpCas9-IRAVRS | I | R | A | V | R | S |
| VNGTN-55 | T | 100% | 100% | 95% | 95% | SpCas9-IRAVQL | I | R | A | V | Q | L |
| VNGTN-56 | created variant | — | — | 50% | 50% | SpCas9-VRKLKR | V | R | K | L | K | R |
| vNGTN-38 | created variant | 100% | 50% | 25% | 25% | SpCas9-VRKLLR | V | R | K | L | L | R |

TABLE 1-continued

Selection results and activity in bacteria of variants against NGTN PAMs

| Sample # | Originally selected against (NGTN) | Approximate survival in bacterial assay against: | | | | Variant name | Amino acid substitutions in variant: | | | | | |
|---|---|---|---|---|---|---|---|---|---|---|---|---|
| | | NGTG | NGTT | NGTC | NGTA | | D1135 | S1136 | G1218 | E1219 | R1335 | T1337 |
| VNGTN-57 | created variant | — | — | 100% | 100% | SpCas9-SRSVRS | S | R | S | V | R | S |
| vNGTN-18 | C | — | 95% | 90% | — | SpCas9-LRSVRS | L | R | S | V | R | S |
| VNGTN-58 | created variant | 100% | 85% | 100% | 100% | SpCas9-VRKIQK | V | R | K | I | Q | K |
| vNGTN-7* | T | 100% | 85% | 100% | 100% | SpCas9-LWKIQK | I | W | K | I | Q | K |
| VNGTN-59 | created variant | 100% | 85% | 100% | 100% | SpCas9-VRMHCK | V | R | M | H | C | K |
| vNGTN-44* | N/A | 100% | 60% | 100% | 95% | SpCas9-SRMHCK | S | R | M | H | C | K |
| VNGTN-61 | created variant | n/a | n/a | n/a | n/a | SpCas9-GRKLLR | G | R | K | L | L | R |
| VNGTN-62 | created variant | n/a | n/a | n/a | n/a | SpCas9-LRKIQK | L | R | K | I | Q | K |
| VNGTN-63 | created variant | n/a | n/a | n/a | n/a | SpCas9-LRSVQK | L | R | S | V | Q | K |
| VNGTN-64 | created variant | n/a | n/a | n/a | n/a | SpCas9-VRKIQK | V | R | K | I | Q | K |
| VNGTN-65 | created variant | n/a | n/a | n/a | n/a | SpCas9-GRSVQL | G | R | S | V | Q | L |
| VNGTN-66 | created variant | n/a | n/a | n/a | n/a | SpCas9-GRKIQL | G | R | K | I | Q | L |

*= that the variant has already been screened in other experiments
n/a = survival was not assessed in that experiment on that PAM

TABLE 2

Selection results and activity in bacteria of variants against NGCN PAMs

| Sample # | Originally selected against (NGCN) | Approximate survival in bacterial assay against: | | | | Variant name | Amino acid substitutions in variant: | | | | | |
|---|---|---|---|---|---|---|---|---|---|---|---|---|
| | | NGCG | NGCT | NGCC | NGCA | | D1135 | S1136 | G1218 | E1219 | R1335 | T1337 |
| VNGCN-1 | G | 100% | 100% | 100% | 100% | SpCas9-WMQAYG | W | M | Q | A | Y | G |
| VNGCN-2 | G | 100% | 100% | 100% | n/a | SpCas9-MQKSER | M | Q | K | S | E | R |
| VNGCN-3 | G | 100% | — | — | 40% | SpCas9-YSVCER | Y | S | V | C | E | R |
| VNGCN-4 | T | 90% | 85% | 90% | 95% | SpCas9-CWNWNS | C | W | N | W | N | S |
| VNGCN-5 | T | 100% | 100% | 100% | 100% | SpCas9-LWRSEY | L | W | R | S | E | Y |
| VNGCN-6 | T | — | 95% | 95% | 100% | SpCas9-QSTWNK | Q | S | T | W | N | K |
| VNGCN-7 | C | n/a | n/a | n/a | n/a | SpCas9-LFEWRA | L | F | E | W | R | A |
| VNGCN-8 | C | — | — | 100% | — | SpCas9-SQSWRS | S | Q | S | W | R | S |
| VNGCN-9 | C | — | — | 100% | — | SpCas9-LKAWRS | L | K | A | W | R | S |
| VNGCN-10 | A | — | 100% | 100% | 100% | SpCas9-LWGWQH | L | W | G | W | Q | H |
| VNGCN-11 | A | — | 15% | 15% | 95% | SpCas9-LSYWAK | L | S | Y | W | A | K |
| VNGCN-12 | A | 50% | 10% | 20% | 95% | SpCas9-RQMYQG | R | Q | M | Y | Q | G |

TABLE 2-continued

Selection results and activity in bacteria of variants against NGCN PAMs

| Sample # | Originally selected against (NGCN) | Approximate survival in bacterial assay against: | | | | Variant name | Amino acid substitutions in variant: | | | | | |
|---|---|---|---|---|---|---|---|---|---|---|---|---|
| | | NGCG | NGCT | NGCC | NGCA | | D1135 | S1136 | G1218 | E1219 | R1335 | T1337 |
| vNGCN-13 | created variant | — | — | — | — | SpCas9-LWREER | L | W | R | E | E | R |
| VNGCN-14 | created variant | 100% | 5% | 10% | 20% | SpCas9-VSSWER | V | S | S | W | E | R |
| VNGCN-15 | created variant | 100% | 3% | 5% | 15% | SpCas9-VSAWER | V | S | A | W | E | R |
| VNGCN-16 | created variant | — | — | — | — | SpCas9-DWREER | D | W | R | E | E | R |
| VNGCN-17 | created variant | 100% | — | — | — | SpCas9-VSGWER | V | S | G | W | E | R |
| VNGCN-18 | G | 100% | 100% | 100% | 100% | SpCas9-MCSFER | M | C | S | F | E | R |
| VNGCN-19 | G | 100% | — | — | 25% | SpCas9-VLMYER | V | L | M | Y | E | R |
| VNGCN-20 | G | 100% | n/a | n/a | n/a | SpCas9-QGANER | Q | G | A | N | E | R |
| VNGCN-21 | G | 100% | 50% | 15% | 50% | SpCas9-GCACER | G | C | A | C | E | R |
| VNGCN-22 | G | 100% | — | — | 5% | SpCas9-SRIAER | S | R | I | A | E | R |
| VNGCN-23 | G | 100% | — | — | 25% | SpCas9-SRRNER | S | R | R | N | E | R |
| vNGCN-10* | T | — | 100% | 90% | 100% | SpCas9-LWGWQH | L | W | G | W | Q | H |
| VNGCN-24 | T | — | 5% | — | — | SpCas9-WMQAVV | W | M | Q | A | V | V |
| vNGCN-25 | T | — | 100% | — | 75% | SpCas9-AYRWSK | A | Y | R | W | S | K |
| VNGCN-26 | T | 100% | 100% | 30% | 65% | SpCas9-LWMREQ | L | W | M | R | E | Q |
| vNGCN-27 | T | — | 100% | 5% | 50% | SpCas9-LWRVVA | L | W | R | V | V | A |
| VNGCN-28 | T | 100% | 100% | n/a | 75% | SpCas9-HSSWVR | H | S | S | W | V | R |
| VNGCN-29 | C | 100% | 100% | 100% | 85% | SpCas9-MWSEPT | M | W | S | E | P | T |
| VNGCN-30 | C | 100% | 100% | 50% | 80% | SpCas9-GWSMQR | G | W | S | M | Q | R |
| VNGCN-31 | C | — | n/a | 75% | — | SpCas9-NKAWRV | N | K | A | W | R | V |
| VNGCN-32 | | 75% | — | 95% | 50% | SpCas9-LCTYEY | L | C | T | Y | E | Y |
| vNGCN-33 | | 80% | 5% | 50% | 50% | SpCas9-GSNWCK | G | S | N | W | C | K |
| vNGCN-34 | C | 85% | 50% | 90% | 100% | SpCas9-GSNYQS | G | S | N | Y | Q | S |
| VNGCN-35 | A | n/a | 50% | 25% | 90% | SpCas9-FMQWVN | F | M | Q | W | V | N |
| vNGCN-36 | A | 40% | 50% | 75% | 100% | SpCas9-YCSWVG | Y | C | S | W | V | G |
| vNGCN-37 | A | 50% | — | 25% | 85% | SpCas9-LWKFEG | L | W | K | F | E | G |
| VNGCN-38 | A | 25% | 35% | 5% | 100% | SpCas9-MCAWCG | M | C | A | W | C | G |
| VNGCN-39 | A | 50% | — | 50% | 50% | SpCas9-GKNWNR | G | K | N | W | N | R |
| vNGCN-2* | A | 100% | 25% | 25% | 75% | SpCas9-MQKSER | M | Q | K | S | E | R |
| VNGCN-40 | created variant | n/a | n/a | n/a | n/a | SpCas9-VRREER | V | R | R | E | E | R |
| VNGCN-41 | A | n/a | n/a | n/a | n/a | SpCas9-AARWCQ | A | A | R | W | C | Q |
| vNGCN-42 | A | n/a | n/a | n/a | n/a | SpCas9-LWLETR | L | W | L | E | T | R |
| vNGCN-43 | A | n/a | n/a | n/a | 85% | SpCas9-FMQWVR | F | M | Q | W | V | R |

TABLE 2-continued

Selection results and activity in bacteria of variants against NGCN PAMs

| Sample # | Originally selected against (NGCN) | Approximate survival in bacterial assay against: | | | | Variant name | Amino acid substitutions in variant: | | | | | |
|---|---|---|---|---|---|---|---|---|---|---|---|---|
| | | NGCG | NGCT | NGCC | NGCA | | D1135 | S1136 | G1218 | E1219 | R1335 | T1337 |
| vNGCN-44 | A | n/a | n/a | n/a | 75% | SpCas9-SSKWPA | S | S | K | W | P | A |
| vNGCN-45 | C | n/a | n/a | 50% | n/a | SpCas9-MWASEG | M | W | A | S | E | G |
| vNGCN-46 | A | n/a | n/a | n/a | 100% | SpCas9-LSRWQR | L | S | R | W | Q | R |
| vNGCN-47 | G | 90% | n/a | n/a | n/a | SpCas9-YAIYER | Y | A | I | Y | E | R |
| vNGCN-48 | G | 75% | n/a | n/a | n/a | SpCas9-ICCCER | | C | C | C | E | R |
| vNGCN-49 | G | 95% | n/a | n/a | n/a | SpCas9-DWFYER | D | W | F | Y | E | R |
| vNGCN-50 | G | 80% | n/a | n/a | n/a | SpCas9-REATER | R | E | A | T | E | R |
| VNGCN-51 | G | 75% | n/a | n/a | n/a | SpCas9-GWAYER | G | W | A | Y | E | R |
| vNGCN-52 | G | 75% | n/a | n/a | n/a | SpCas9-YAIYER | Y | A | I | Y | E | R |
| vNGCN-53 | G | 85% | n/a | n/a | n/a | SpCas9-LSVSER | L | S | V | S | E | R |
| VNGCN-54 | A | n/a | n/a | n/a | 75% | SpCas9-VRAWCR | V | R | A | W | C | R |
| VNGCN-55 | G | 75% | n/a | n/a | n/a | SpCas9-KWREQR | K | W | R | E | Q | R |
| VNGCN-56 | G | 75% | n/a | n/a | n/a | SpCas9-ARGAER | A | R | G | A | E | R |
| VNGCN-57 | C | n/a | n/a | 75% | n/a | SpCas9-HASWCK | H | A | S | W | C | K |
| vNGCN-58 | G | 100% | n/a | n/a | n/a | SpCas9-YVRSER | Y | V | R | S | E | R |
| vNGCN-59 | G | 80% | n/a | n/a | n/a | SpCas9-QRLAER | Q | R | L | A | E | R |
| VNGCN-60 | A | n/a | n/a | n/a | n/a | SpCas9-AARWER | A | A | R | W | E | R |
| vNGCN-61 | G | 75% | n/a | n/a | n/a | SpCas9-LILSER | L | I | L | S | E | R |
| vNGCN-62 | A | n/a | n/a | n/a | n/a | SpCas9-LWPSRG | L | W | P | S | R | G |
| VNGCN-63 | A | n/a | n/a | n/a | n/a | SpCas9-LWTWIK | L | W | T | W | - | K |
| VNGCN-64 | created variant | n/a | n/a | n/a | n/a | SpCas9-VRKSER | V | R | K | S | E | R |
| vNGCN-65 | created variant | n/a | n/a | n/a | n/a | SpCas9-ICKSER | | C | K | S | E | R |
| vNGCN-66 | C/T | n/a | n/a | n/a | n/a | SpCas9-MQSVQL | M | Q | S | V | Q | L |
| VNGCN-67 | created variant | n/a | n/a | n/a | n/a | SpCas9-LRSVER | L | R | S | V | E | R |
| vNGCN-68 | created variant | n/a | n/a | n/a | n/a | SpCas9-LSRWER | L | S | R | W | E | R |

*= that the variant has already been screened in other experiments n/a = survival was not assessed in that experiment on that PAM

TABLE 3

Selection results and activity in bacteria of variants against NGAN PAMs

| Sample # | Originally selected against (NGAN) | Approximate survival in bacterial assay against: | | | | Variant name | Amino acid substitutions in variant: | | | | | |
|---|---|---|---|---|---|---|---|---|---|---|---|---|
| | | NGAG | NGAT | NGAC | NGAA | | D1135 | S1136 | G1218 | E1219 | R1335 | T1337 |
| vNGAN-1 | G | 100% | 10% | 5% | 1% | SpCas9-LRLSAR | L | R | L | S | A | R |
| VNGAN-2 | G | 100% | — | 1% | — | SpCas9-ASEVTR | A | S | E | V | T | R |
| VNGAN-3 | T | 100% | 100% | 95% | 90% | SpCas9-KWMMCG | K | W | M | M | C | G |
| VNGAN-4 | C | — | — | 100% | — | SpCas9-VRGAKE | V | R | G | A | K | E |
| VNGAN-5 | C | — | — | 100% | - | SpCas9-MRARKE | M | R | A | R | K | E |
| VNGAN-6 | G | 75% | — | — | — | SpCas9-AEEQQR | A | E | E | Q | Q | R |
| VNGAN-7 | A | 95% | 5% | — | 80% | SpCas9-TRGSFR | T | R | G | S | F | R |
| VNGAN-8 | A | 95% | 10% | 90% | 90% | SpCas9-VRNYTK | V | R | N | Y | T | K |
| VNGAN-9 | T | 100% | 100% | 95% | 95% | SpCas9-AWNFQV | A | W | N | F | Q | V |
| vNGAN-10 | A | 100% | 35% | — | 20% | SpCas9-WMRKVA | W | M | R | K | V | A |
| vNGAN-11 | A | 40% | 100% | — | 75% | SpCas9-CWTCLQ | C | W | T | C | L | Q |
| vNGAN-12 | A | 100% | 100% | 5% | 75% | SpCas9-LWTTLN | L | W | T | T | L | N |
| VNGAN-13 | G | 100% | 95% | 95% | 95% | SpCas9-SRMHCK | S | R | M | H | C | K |
| vNGAN-14 | T | 100% | 100% | 95% | 95% | SpCas9-CWCQCV | C | W | C | Q | C | V |
| VNGAN-15 | T | 100% | 5% | — | 10% | SpCas9-GCLCVR | G | C | L | C | V | R |
| vNGAN-16 | C | 100% | 50% | — | — | SpCas9-GGCQLR | G | G | C | Q | L | R |
| vNGAN-17 | G | 100% | — | — | — | SpCas9-AEEQQR | A | E | E | Q | Q | R |
| vNGAN-18 | G | 90% | 100% | 10% | 25% | SpCas9-QNNQVF | Q | N | N | Q | V | F |
| vNGAN-19 | T | 100% | 100% | | 100% | SpCas9-GWEKVR | G | W | E | K | V | R |
| VNGAN-20 | T | 1% | 100% | 50% | — | SpCas9-NRAVNG | N | R | A | V | N | G |
| VNGAN-21 | ? | 1% | 100% | 50% | — | SpCas9-NRAVNG | N | R | A | V | N | G |
| VNGAN-22 | C | 100% | 1% | 100% | — | SpCas9-SRQMRG | S | R | Q | M | R | G |
| VNGAN-23 | C | — | — | — | — | SpCas9-RAQPNL | R | A | Q | P | N | L |
| VNGAN-24 | A | 50% | 5% | — | 100% | SpCas9-LRSYLH | L | R | S | Y | L | H |
| vNGAN-25 | G | 100% | 95% | 100% | 90% | SpCas9-SRMHCK | S | R | M | H | C | K |
| vNGAN-26 | G | 100% | — | — | — | SpCas9-ACTSVR | A | C | T | S | V | R |
| VNGAN-27 | G | 100% | — | — | — | SpCas9-MVVHIR | M | V | V | H | I | R |
| VNGAN-28 | G | 100% | — | — | — | SpCas9-VRGNNR | V | R | G | N | N | R |
| VNGAN-29 | G | 100% | — | — | — | SpCas9-RGFCLR | R | G | F | C | L | R |
| vNGAN-30 | G | 100% | — | — | — | SpCas9-VQDAQR | V | Q | D | A | Q | R |
| vNGAN-31 | T | 100% | 100% | 95% | 95% | SpCas9-GWRQSK | G | W | R | Q | S | K |
| VNGAN-32 | T | 5% | 100% | — | — | SpCas9-AWLCLS | A | W | L | C | L | S |
| vNGAN-33 | T | 100% | 100% | — | 100% | SpCas9-KWARVV | K | W | A | R | V | V |
| VNGAN-34 | T | 80% | 100% | 20% | 15% | SpCas9-LAAQTP | L | A | A | Q | T | P |
| vNGAN-35 | T | 95% | 100% | 10% | 90% | SpCas9-GWNHLQ | G | W | N | H | L | Q |
| vNGAN-36 | T | 100% | 100% | 100% | 5% | SpCas9-MWAARP | M | W | A | A | R | P |

TABLE 3-continued

Selection results and activity in bacteria of variants against NGAN PAMs

| Sample # | Originally selected against (NGA_N_) | Approximate survival in bacterial assay against: | | | | Variant name | Amino acid substitutions in variant: | | | | | |
|---|---|---|---|---|---|---|---|---|---|---|---|---|
| | | NGAG | NGAT | NGAC | NGAA | | D1135 | S1136 | G1218 | E1219 | R1335 | T1337 |
| vNGAN-37 | C | 95% | 100% | 50% | 30% | SpCas9-KWRCTG | K | W | R | C | T | G |
| vNGAN-38 | C | 50% | — | 100% | — | SpCas9-LAKARP | L | A | K | A | R | P |
| VNGAN-39 | C | 100% | 100% | 100% | 30% | SpCas9-SRMHCK | S | R | M | H | C | K |
| vNGAN-40 | C | — | — | 100% | — | SpCas9-VKMAKG | V | K | M | A | K | G |
| vNGAN-41 | C | — | — | 100% | — | SpCas9-QRKTRE | Q | R | K | T | R | E |
| vNGAN-42 | C | — | — | 50% | — | SpCas9-NTAVKQ | N | T | A | V | K | Q |
| vNGAN-43 | A | 100% | 100% | 50% | 100% | SpCas9-LCRQQR | L | C | R | Q | Q | R |
| VNGAN-44 | A | 100% | 90% | 100% | 100% | SpCas9-CWSHQR | C | W | S | H | Q | R |
| vNGAN-45 | A | 30% | 90% | 25% | 100% | SpCas9-MWVHLN | M | W | V | H | L | N |
| VNGAN-46 | A | 100% | 100% | 25% | 100% | SpCas9-SRTHTQ | S | R | T | H | T | Q |
| vNGAN-47 | A | 100% | 50% | — | 100% | SpCas9-LQKSMR | L | Q | K | S | M | R |
| vNGAN-48 | A | 100% | 100% | — | 90% | SpCas9-LWEVIR | L | W | E | V | I | R |
| VNGTN-37 | created variant | 20% | — | — | — | SpCas9-VSKLLR | V | S | K | L | L | R |
| VNGTN-38 | created variant | 50% | — | — | — | SpCas9-VRKLLR | V | R | K | L | L | R |
| vNGTN-27* | NGTG | 10% | — | — | — | SpCas9-GAKLLR | G | A | K | L | L | R |
| VNGTN-39 | created variant | — | — | — | — | SpCas9-VSAVQL | V | S | A | V | Q | L |
| VNGTN-40 | created variant | 1% | — | — | — | SpCas9-VRAVQL | V | R | A | V | Q | L |
| vNGTN-9* | NGTT | 5% | — | 1% | — | SpCas9-IRAVQL | I | R | A | V | Q | L |
| vNGTN-41 | created variant | 1% | — | 100% | — | SpCas9-VSSVRS | V | S | S | V | R | S |
| vNGTN-42 | created variant | 25% | — | 100% | — | SpCas9-VRSVRS | V | R | S | V | R | S |
| vNGTN-18* | NGTC | 25% | — | 100% | — | SpCas9-LRSVRS | L | R | S | V | R | S |
| VNGTN-43 | N/A | 50% | — | | 1% | SpCas9-SRGERT | S | R | G | E | R | T |
| VNGTN-44 | N/A | 90% | 80% | n/a | 50% | SpCas9-SRMHCK | S | R | M | H | C | K |
| VNGTN-52 | created variant | 60% | - | 75% | - | SpCas9-VRKLRS | V | R | K | L | R | S |
| vNGTN-38* | created variant | 60% | - | | - | SpCas9-VRKLLR | V | R | K | L | L | R |
| VNGTN-53 | created variant | 15% | 5% | 10% | 1% | SpCas9-LRSVQL | L | R | S | V | Q | L |
| vNGTN-18* | NGTC | 50% | 5% | 100% | — | SpCas9-LRSVRS | L | R | S | V | R | S |
| VNGTN-54 | created variant | 50% | 5% | 100% | — | SpCas9-IRAVRS | I | R | A | V | R | S |
| VNGTN-55 | NGTT | 5% | 1% | 1% | — | SpCas9-IRAVQL | I | R | A | V | Q | L |
| VNGTN-56 | created variant | 5% | — | 35% | — | SpCas9-VRKLKR | V | R | K | L | K | R |

TABLE 3-continued

Selection results and activity in bacteria of variants against NGAN PAMs

| Sample # | Originally selected against (NGAN) | Approximate survival in bacterial assay against: | | | | Variant name | Amino acid substitutions in variant: | | | | | |
|---|---|---|---|---|---|---|---|---|---|---|---|---|
| | | NGAG | NGAT | NGAC | NGAA | | D1135 | S1136 | G1218 | E1219 | R1335 | T1337 |
| vNGTN-38* | created variant | 35% | — | — | — | SpCas9-VRKLLR | V | R | K | L | L | R |
| VNGTN-57 | created variant | 20% | — | 100% | — | SpCas9-SRSVRS | S | R | S | V | R | S |
| vNGTN-18* | NGTC | 25% | — | 100% | — | SpCas9-LRSVRS | L | R | S | V | R | S |
| VNGTN-58 | created variant | 85% | 5% | 95% | 25% | SpCas9-VRKIQK | V | R | K | I | Q | K |
| VNGTN-7* | NGTT | 85% | 100% | 100% | 95% | SpCas9-LWKIQK | L | W | K | I | Q | K |
| VNGTN-59 | created variant | 95% | 100% | 100% | 90% | SpCas9-VRMHCK | V | R | M | H | C | K |
| vNGTN-44* | N/A | 85% | 90% | 100% | 75% | SpCas9-SRMHCK | S | R | M | H | C | K |

*= that the variant has already been screened in other experiments
n/a = survival was not assessed in that experiment on that PAM

What is claimed is:

1. A base editor protein comprising a spCas9 protein, wherein the spCas9 protein comprises a PAM interacting domain of SEQ ID NO: 1 that has mutations at positions corresponding to D1135, S1136, and G1218 of SEQ ID NO: 1, wherein the mutation at D1135 is M, the mutation at S1136 is Q, and the mutation at G1218 is K.

2. The base editor protein of claim 1, further comprising a mutation at position corresponding to E1219 of SEQ ID NO:1.

3. The base editor protein of claim 2, wherein the mutation at position corresponding to E1219 is S or F.

4. The base editor protein of claim 1, further comprising:
   (i) a mutation at a position corresponding to positions selected from the group consisting of D10, E762, D839, H983, and D986 of SEQ ID NO:1; and/or
   (ii) a mutation at position corresponding to H840 or N863 of SEQ ID NO:1.

5. The base editor of claim 4, wherein the mutations are:
   (i) D10A or D10N, and/or
   (ii) H840A, H840N, or H840Y.

6. The base editor protein of claim 1, further comprising a mutation at position corresponding to R1335 of SEQ ID NO:1.

7. The base editor protein of claim 1, further comprising a mutation at position corresponding to T1337 of SEQ ID NO:1.

8. The base editor protein of claim 1, further comprising a mutation at position corresponding to E1219 of SEQ ID NO:1, a mutation at position corresponding to R1335 of SEQ ID NO:1, and a mutation at position corresponding to T1337 of SEQ ID NO:1.

9. The base editor protein of claim 8, wherein the mutation at position corresponding to E1219 is S or F, the mutation at position corresponding to R1335 is E, and the mutation at position corresponding to T1337 is R.

10. The base editor protein of claim 9, further comprising:
    (i) a mutation at a position corresponding to positions selected from the group consisting of D10, E762, D839, H983, and D986 of SEQ ID NO: 1; and/or
    (ii) a mutation at position corresponding to H840 or N863 of SEQ ID NO:1.

11. The base editor of claim 10, wherein the mutations are:
    (i) D10A or D10N, and/or
    (ii) H840A, H840N, or H840Y.

12. The base editor of claim 11, wherein the mutation is D10A or D10N.

13. A method of altering the genome of a cell, the method comprising expressing in the cell, or contacting the cell with, the base editor of claim 12, and a guide RNA having a region complementary to a selected portion of the genome of the cell.

14. A method of altering a double stranded DNA (dsDNA) molecule, the method comprising contacting the dsDNA molecule with the base editor of claim 12, and a guide RNA having a region complementary to a selected portion of the dsDNA molecule.

15. A method of editing a nucleotide base in a double stranded DNA (dsDNA) molecule, the method comprising contacting the dsDNA molecule with the base editor protein of claim 12, and a guide RNA having a region complementary to a selected portion of the dsDNA molecule.

16. The base editor protein of claim 1, wherein the protein comprises one or more of a nuclear localization sequence, cell penetrating peptide sequence, and/or affinity tag.

17. The base editor protein of claim 1, wherein the base editor comprises (i) a cytidine deaminase domain or (ii) an adenosine deaminase domain.

18. The base editor protein of claim 17, wherein the cytidine deaminase domain is selected from the group consisting of apolipoprotein B mRNA-editing enzyme, catalytic polypeptide-like (APOBEC) deaminase; activation-induced cytidine deaminase (AID); and cytosine deaminase acting on tRNA (CDAT).

19. The base editor protein of claim 17, wherein the adenosine deaminase domain is selected from the group consisting of adenosine deaminase 1 (ADA1), ADA2; adenosine deaminase acting on RNA 1 (ADAR1), ADAR2, ADAR3; adenosine deaminase acting on tRNA 1 (ADAT1), ADAT2, ADAT3; and naturally occurring or engineered tRNA-specific adenosine deaminase (TadA).

20. The base editor protein of claim 1, wherein the SpCas9 has at least 80% sequence identity to the amino acid sequence of SEQ ID NO: 1.

21. The base editor protein of claim 20, wherein the SpCas9 has at least 85% sequence identity to the amino acid sequence of SEQ ID NO: 1.

22. The base editor protein of claim 21, wherein the SpCas9 has at least 90% sequence identity to the amino acid sequence of SEQ ID NO: 1.

23. A method of altering the genome of a cell, the method comprising expressing in the cell, or contacting the cell with, the base editor of claim 1, and a guide RNA having a region complementary to a selected portion of the genome of the cell.

24. A method of altering a double stranded DNA (dsDNA) molecule, the method comprising contacting the dsDNA molecule with the base editor of claim 1, and a guide RNA having a region complementary to a selected portion of the dsDNA molecule.

25. A method of editing a nucleotide base in a double stranded DNA (dsDNA) molecule, the method comprising contacting the dsDNA molecule with the base editor protein of claim 1, and a guide RNA having a region complementary to a selected portion of the dsDNA molecule.

* * * * *